(12) United States Patent
Alpegiani et al.

(10) Patent No.: US 6,482,827 B1
(45) Date of Patent: Nov. 19, 2002

(54) MATRIX METALLOPROTEINASE INHIBITORS

(75) Inventors: Marco Alpegiani, Milan; Pierluigi Bissolino, Pavia; Francesca Abrate, Milan; Ettore Perrone, Milan; Riccardo Corigli, Milan; Daniela Jabes, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/147,798

(22) PCT Filed: Jul. 7, 1998

(86) PCT No.: PCT/EP98/04220

§ 371 (c)(1),
(2), (4) Date: Mar. 10, 1999

(87) PCT Pub. No.: WO99/02510

PCT Pub. Date: Jan. 21, 1999

(30) Foreign Application Priority Data

Jul. 10, 1997 (GB) .............................................. 9714548
Nov. 18, 1997 (GB) .............................................. 9742395

(51) Int. Cl.[7] ...................... A61K 31/16; A61K 31/395; A61K 31/495; A61K 31/535

(52) U.S. Cl. ............................. 514/254.11; 514/210.01; 514/238.2; 514/252.11; 514/255.01; 514/255.05; 514/320; 514/616; 544/336; 544/357; 544/360; 544/376; 544/164; 546/207; 546/224; 548/953; 564/155; 564/156; 564/157; 564/159

(58) Field of Search ................................ 544/376, 336, 544/357, 360, 405, 164; 514/254.11, 210.01, 238.2, 252.11, 255.01, 255.05, 320, 616; 546/207, 224; 548/953; 564/155, 156, 157, 159

(56) References Cited

U.S. PATENT DOCUMENTS

5,710,149 A  *  1/1998  Cliffe ........................... 514/212
6,071,916 A  *  6/2000  Askin et al. ................. 514/253

FOREIGN PATENT DOCUMENTS

WO  95/33731  * 12/1995
WO  96/33166  * 10/1996

OTHER PUBLICATIONS

Chem. Abst. vol 108(13), the abstract No. 112899e (Mar. 1988).*

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A compound, which is an amine derivative of formula (I) wherein W is —CNHOH or —COOH: $R_1$ and $R_2$ are each hydrogen or an organic residue, $R_3$ is an organic group, Q is a secondary or tertiary acyclic or cyclic amido group, and the pharmaceutically acceptable salts, solvates and hydrates thereof, are inhibitors of matrix metalloproteinases (MMPs) and of the release of tumor necrosis factor-alpha (TNF) from cells. They are therefore useful in the prevention, control and treatment of diseases in which MMPs or TNF are involved, especially tumoral and inflammatory diseases. Processes for their preparation and pharmaceutical compositions containing them are also described.

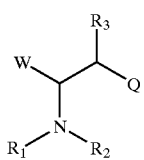

(I)

18 Claims, No Drawings

MATRIX METALLOPROTEINASE INHIBITORS

This application is a 371 of PCT/EP98/04220 filed Jul. 7, 1998.

The present invention relates to new inhibitors of matrix metalloproteinases (hereinafter MMPs), to a process for their preparation, to pharmaceutical compositions containing them, and to the use of such compounds in the prevention, control and treatment of diseases in which the proteolytic action of MMPs is involved.

Certain disease states are characterised by an imbalance of active MMPs and their natural inhibitors, the tissue inhibitors of metalloproteinases (hereinafter TIMPs). When TIMP levels are insufficient, a progressive slow degradation of the extracellular matrix occurs, for example cartilage matrix loss in rheumatoid arthritis (L. A. Walakovits et al., Arthritis Rheum, 35:35–42, 1992) and osteoarthritis (D. D. Dean et al., J. Clin. Invest., 84:678–685, 1989), and bone matrix degradation in osteoporosis (p. A. Hill et al., Biochem. J., 308:167–175, 1995). In other situations, such as congestive heart failure, rapid degradation of the heart's extracellular matrix occurs (P. W. Armstrong et al., Canadian J. Cardiol. 10:214–220, 1994). Cancer cells use MMPs, either expressed by themselves or by the surrounding tissues, to achieve rapid remodelling of the extracellular matrix. There is considerable evidence that MMPs are involved in at least 3 aspects of the growth and spread of tumors (e.g., see A. H. Davidson et al., Chemistry & Industry, 258–261, 1997, and references therein). In the process of tumor metastasis, MMPs are used to break down the extracellular matrix, allowing primary tumor cancer cells to invade neighbouring blood vessels where they are transported to different organs and establish secondary tumors. The invasive growth at these secondary sites also needs MMPs to help break down tissue. In addition, MMP activity contributes to the invasive in-growth of new blood vessels (angiogenesis) which is required for tumors to grow above a certain size.

Low molecular weight compounds able to inhibit one or more of the matrix metalloproteinases, in particular stromelysin-1 (M-3; EC 3.4.24.17), gelatinase A (MMP-2; EC 3.4.24.24), gelatinase B (MM-9; EC 3.4.24.35), neutrophil collagenase or collagenase-2 (MMP-8; EC 3.4.24.34), interstitial collagenase or collagenase-1 (MMP-1; EC 3.4.27.7), matrilysin (MMP-7; EC 3.4.24.23), collagenase-3 (MMP-13), and the membrane-type metalloproteinase (MT-MMPs: MMP-14, MNP-15, MMP-16, MMP-17) are currently considered as promising therapeutic agents in degenerative, tumoral and autoimmune pathologies (e.g., P. D. Brown: "Matrix metalloproteinase inhibitors: A new class of anticancer agent", Curr. Opin. Invest. Drugs, 2:617–626, 1993; A. Krantz: "Proteinases in Inflammation", Annu. Rep. Med. Chem. 28:187–195, 1993). Many of such compounds described hitherto are peptide derivatives or pseudopeptides, bearing analogies to recognized peptide substrates of these enzymes, and characterized in addition by a functional group capable of binding the Zn (II) atom present in the catalytic site of said enzymes. Known classes of MMP inhibitors include those in which the Zn binding group is a hydroxamic acid, and the skeleton, as represented in the general formula (A), mimicks the amino acid sequence of collagen at the site cleaved by collagenase:

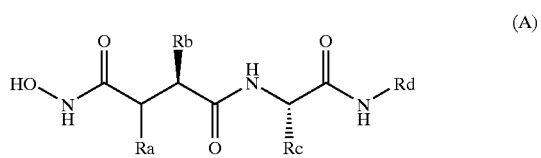

(A)

wherein $R_a$, $R_b$, $R_c$, and $R_d$ are hydrogen atoms or appropriate substituents (e.g., N. R. A. Beeley et al., "Inhibitors of matrix metalloproteinases (MMP's)", Curr. Opin. Ther. Patents 4:7–16, 1994; J. R. Porter et al., "Recent developments in matrix metalloproteinase inhibitors", Exp. Opin. Ther. Patents 5:1287–1296, 1995; J. R. Morphy et al., "Matrix metalloproteinase inhibitors: Current status", Curr. Med. Chem. 2:743–762, 1995; R. P. Beckett et al., "Recent advances in matrix metalloproteinase research", DDT 1:16–26, 1996). Said MMP inhibitors of the prior art can be described as "peptide-based hydroxamates" or "substrate-based" inhibitors (e.g., A. H. Davidson et al., "The inhibition of matrix metalloproteinase enzymes", Chemistry & Industry, 258–261, 1997).

Although MMPs have been recognized as drug targets for at least 20 years, and potent MMP inhibitors described by formula (A) have been disclosed since 1986 or before (e.g., see J. P. Dickens et al., U.S. Pat. No. 4,599,361), no drug of this type has arrived at the market yet. This is not because of questions about the therapeutic potential of MMP inhibitors, but because of problems of "peptide-based hydroxamates", such as aqueous solubility, metabolic stability, and other desirable properties, oral bioavailability in particular (e.g., J. R. Porter, reference above; J. Hodgson, "Remodelling MMPIs", Biotechnology 13:554–557, 1995). For example, it is well known that most "peptide-based hydroxamates" of general formula (A) are rapidly glucuronidated, oxidized to the carboxylic acid, and excreted in the bile (e.g., see J. Singh et al., Bioorg. Med. Chem. Lett. 5:337–342, 1995, and other references above). Finally, another type of problem of the known inhibitors described by general formula (A) may be one of tolerability. This problem is emerging for the most advanced MMP inhibitor in the clinic, marimastat (formula A; $R_a$=OH, $R_b$=CH$_2$CHMe$_2$, $R_c$=CMe$_3$, $R_d$=Me), which was reported to give muscoloskeletal problems in humans. We have extended these observations by developing an animal model of tolerability with MMP inhibitors (S. Castellino et al., unpublished), involving intraperitoneal administration of the latter in rats for 10 consecutive days, and histological evaluation of stifle joints at the end of treatment. In this model, peptide-based MMP inhibitors of the prior art, e.g. Roche Ro31-9790 (formula A; $R_a$=H, $R_b$=CH$_2$CHMe$_2$, $R_c$=CMe$_3$, $R_d$=Me), at daily doses of 150 mg/kg or less, elicited hypertrophic fibrosis of stifle ligaments, interstitial hypertrophic fibrosis of skeletal muscles, hypertrophic fibroplasia of the periostium and synovium, and chondrosysplasia and decreased endochondrial ossification of the ephyseal plate. Although the precise reasons for these side-effects are not known at present, they support a strong need for better and diversified molecules, especially as far as the properties referred to above are concerned.

The present invention is concerned with novel MMP inhibitors, specifically characterized by the presence of a nitrogen atom as a substituent at the carbon atom next to the zinc-binding group, and with less or no peptidic character, as compared to substrate-based inhibitors of the prior art.

The present invention provides a compound which is an amine derivative of formula (I)

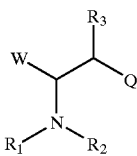

(I)

wherein

W is —CONHOH or —COOH;

$R_1$ and $R_2$, which are the same or different, are each hydrogen or a group G, which is methyl, $C_2$–$C_{10}$ alkyl, $C_2$–$C_{10}$ alkenyl, $C_3$–$C_7$ cycloalkyl, cycloalkyl-$C_1$–$C_{10}$-alkyl, aryl, aryl-$C_1$–$C_{10}$-alkyl, aryl-$C_2$–$C_{10}$-alkenyl, heterocyclyl, heterocyclyl-$C_1$–$C_{10}$-alkyl or heterocyclyl-$C_2$–$C_{10}$-alkenyl, the said methyl, alkyl, alkenyl, cycloalkyl, aryl and heterocyclyl groups being unsubstituted or substituted by one to three substituents; or —$SO_2$—G, wherein G is as defined above; or —SO—G, wherein G is as defined above; or —CO—G, wherein G is as defined above; or —COO—G, wherein G is as defined above; or —$SO_2$—$NH_2$, —$SO_2$—NHG or —$SO_2$—NGG', wherein G is as defined above and G', which is the same or different, is as defined above for G, or G and G', together with the nitrogen atom to which they are attached, form a saturated or unsaturated 3- to 7-membered azaheterocyclic ring, which may be fused to a carbocyclic, heterocyclic, or aromatic ring, and may be substituted at any carbon or additional nitrogen atom, or a group —$CONH_2$, —CONHG or —CO—NGG' wherein G and G' are as defined above, or G and G', together with the nitrogen atom to which they are attached, constitute a saturated or unsaturated 3- to 7-membered azaheterocyclic ring, which may be fused to a carbocyclic, heterocyclic, or aromatic ring, and may be substituted at any carbon or additional nitrogen atom, or $R_1$ and $R_2$, taken together with the nitrogen atom to which they are attached, form a saturated or unsaturated 3- to 7-membered azaheterocyclic ring, which may be fused to a carbocyclic, heterocyclic, or aromatic ring, and may be substituted at any carbon or additional nitrogen atom;

$R_3$ is $C_1$–$C_{15}$ alkyl, either unsubstituted or substituted by a $C_3$–$C_7$ cycloalkyl group, the alkyl and/or the cycloalkyl group being either unsubstituted, or substituted by one to three substituents selected from methyl, ethyl, $C_3$–$C_4$ linear or branched alkyl, fluoro, chloro, $C_1$–$C_4$ alkoxy, nitro, amino, dimethylamino, carboxy and carboxymethyl; or $R_3$ is a group —R—X—$R^1$ wherein R is a chemical bond, —$CH_2$—, —$(CH_2)_m$— wherein m is an integer from 2 to 5, —CH=CH—, —$CH_2$CH=CH—, phenylene (i.e., —$C_6H_4$—), —$CH_2$CH=CH—$C_6H_4$—, —$CH_2CH_2$CH=CH—, —$CH_2$—CC—, —$CH_2CH_2$—CC—, —$CH_2CH_2$CH=CH—$C_6H_4$—, —$CH_2$—CC—$C_6H_4$—, or —$CH_2CH_2$—CC—$C_6H_4$—; X is a direct bond, an oxygen atom, a sulfur atom, or a sulfinyl —S(O)—, sulfonyl —S(O)$_2$ or carbamoyl group —CONH— or —NHCO—; and $R^1$ is $C_1$–$C_6$ alkyl, $C_2$–$C_6$ alkenyl, phenyl, phenyl-($C_1$–$C_6$)-alkyl, phenyl-($C_2$–$C_6$)-alkenyl, heterocyclyl, or heterocyclyl-($C_1$–$C_6$)-alkyl, either unsubstituted or substituted by a group selected from F, Cl, Br, $C_1$–$C_4$ alkyl, $C_1$–$C_4$ alkoxy, alkylthio, arylthio, alkylsulfonyl, and arylsulfonyl;

Q, being a secondary or tertiary carboxyamide, is:

a group —CONHG or —CONGG', wherein G and G' are as defined above; or a group —CONH—CHGG', wherein G and G' are as defined above; or a group —CONG"—CHGG', wherein G", being the same or different, is defined as G above; or a group —CONH—$CH_2$—CHGG' or a group —CONG"—$CH_2$—CHGG', wherein G, G' and G" are as defined above; or a group —CO-azaheterocyclyl, wherein azaheterocyclyl, which is either unsubstituted or substituted, is as defined below; with the proviso that when Q is —CONHG, and G is methyl, alkylmethyl, cycloalkyl-methyl, aryl-methyl or hetherocyclyl-methyl, then such methyl or substituted methyl cannot be further substituted by a group —$(CH_2)_t$—$CO_2H$, wherein t is 0, or esters and amides thereof, and a pharmaceutically acceptable salt, solvate or hydrate thereof.

As used herein the term "alkyl" refers to a straight or branched chain alkyl moiety having from 1 to 10 carbon atoms, including for example, methyl, ethyl, propyl, isopropyl, n-butyl, i-butyl, sec-butyl, tert-butyl, n-pentyl, isopentyl, n-hexyl, n-heptyl, n-octyl and so on. The term "alkenyl" as used herein refers to a straight or branched chain alkenyl moiety having from 2 to 10 carbon atoms and having in addition one double bond of either E or Z stereochemistry where applicable. Examples of alkenyl groups are: vinyl, allyl, metallyl, butenyl, crotyl and so on.

The term "cycloalkyl" as used herein refers to a saturated carbocyclic group of 3 to 7 carbon atoms, such as cyclopropyl, cyclobutyl, cyclopentyl, cyclohexyl, cycloheptyl.

The term "aryl" as used herein refers to a monocyclic or bicyclic aromatic hydrocarbon group of 6 to 10 carbon atoms, such as phenyl, naphthyl, indanyl; furthermore, "aryl" as used herein may refer to a diphenyl group (—$C_6H_4$—$C_6H_5$), a 4-pyridyl-phenyl group, and a methylenedioxyphenyl group.

The term "heterocyclyl" as used herein refers to a 3- to 7-membered, saturated or unsaturated heterocyclyl ring, containing at least one heteroatom selected from O, S and N, wherein any ring nitrogen may be oxidized as an N-oxide, any ring carbon may be oxidized as a carbonyl, and any ring sulfur may be oxidized as a sulfoxide or sulfone; and wherein said heterocyclyl ring may be optionally fused to a second 5- or 6-membered, saturated or unsaturated heterocyclyl ring, or to a $C_3$–$C_7$ cycloalkyl ring, or to a benzene or naphthalene ring. Examples of heterocyclyl groups are pyrrolyl, pyrrolidinyl, pyrazolyl, imidazolyl, triazolyl, tetrazolyl, oxazolyl, isoxazolyl, thiazolyl, isothiazolyl, thiadiazolyl thienyl, tetrahydrothienyl, furyl, tetrahydrofuryl, aziridinyl, oxiranyl, azetidinyl, succinimido, pyridyl, piperidinyl, pyrazinyl, piperazinyl, pyridazinyl, hexahydropyridazinyl, pyrimidinyl, pyranyl, tetrahydropyranyl, benzothienyl, benzothiazolyl, benzoxazolyl isobenzofuranyl, benzofuranyl, benzimidazolyl, indazolyl, chromenyl, indolyl, oxindolyl, phthalimido, 1-oxo-2-isoindolyl, quinolyl, isoquinolyl, tetrahydroisoquinolyl, indolizinyl, isoindolyl, 2-oxoisoindolyl, quinuclidinyl, hydantoinyl, saccarinyl, cinnolinyl, purinyl, morpholinyl, thiomorpholinyl, dioxanyl, dithianyl, azepinyl and so on.

The term "azaheterocyclyl" as used herein includes any of the heterocyclyl groups, as defined above, containing at least one nitrogen atom, said heterocyclyl group being linked to the rest of the molecule by a nitrogen atom.

Substituents which may be present in the methyl, alkyl, alkenyl, aryl, cycloalkyl, heterocyclyl and azaheterocyclyl groups in any of the above specifications include the following ones:

a group —$(CH_2)_t$—Hal, wherein Hal is halo (i.e., fluoro, bromo, chloro or iodo), and t is an integer from 0 to 3;

a group —$(CH_2)_t$—$CF_3$, or a group —$(CH_2)_t$—$CHF_2$, wherein t is as defined above, a group —$CH_2)_t$—OH, wherein t is as defined above;

a group —$(CH_2)_t$—$OR^{II}$, wherein t is as defined above, and $R^{II}$ is straight or branched $C_1$–$C_6$ alkyl, aryl, arylmethyl, heterocyclyl, or heterocyclylmethyl, optionally substituted by hydroxy, methoxy, methyl amino, methylamino, dimethylamino, chloro and fluoro;

a group —$(CH_2)_t$—$OC(O)R^{II}$, wherein t and $R^{II}$ are as defined above;

a group —$(CH_2)_t$—$OC(O)OR^{II}$, wherein t and $R^{II}$ are as defined above;

a group —$(CH_2)_t$—$OC(O)NH_2$, or —$(CH_2)_t$—$OC(O)NHR^{II}$, or —$(CH_2)_t$—$OC(O)NR^{II}R^{III}$, wherein t is as defined above, $R^{II}$ is as defined above, and $R^{III}$, being the same or different, is defined as $R^{II}$ above; or $R^{II}$ and $R^{III}$ taken together with the nitrogen atom form an azaheterocycl ring;

oxo;

a group —$(CH_2)_t$—$NO_2$, wherein t is as defined above;

a group —$(CH_2)_t$—$N_3$, wherein t is as defined above;

a group —$(CH_2)_t$—CN, wherein t is as defined above;

a group —$(CH_2)_t$—SH, wherein t is as defined above, and acetyl or phenylacetyl esters thereof (i.e., —$(CH_2)_t$—$SCOCH_3$ and —$(CH_2)_t$—$SCOCH_2C_6H_5$);

a group —$(CH_2)_t$—$NH_2$, or —$(CH_2)_t$—$NHR^{II}$, or —$(CH_2)_t$—$NR^{II}R^{III}$, wherein t, $R^{II}$ and $R^{III}$ are as defined above, or $R^{II}$ and $R^{III}$ taken together with the nitrogen atom form an azaheterocyclyl ring;

a group —$(CH_2)_t$—$NHC(O)R^{II}$, or —$(CH_2)_t$—$NR^{II}C(O)R^{III}$, or —$(CH_2)_t$—$NHC(O)OR^{II}$, wherein t, $R^{II}$ and R III are as defined above;

a group —$(CH_2)_t$—$NH(CO)NH_2$, or —$(CH_2)_t$—$NH(CO)NHR^{II}$, or —$(CH_2)_t$—$NH(CO)NR^{II}R^{III}$, wherein t, $R^{II}$ and $R^{III}$ are as defined above, including the special case wherein $R_{II}$ and $R^{III}$ taken together with the nitrogen atom form an azaheterocyclyl ring;

a group —$(CH_2)_t$—$NHSO_2R^{II}$, wherein t and $R^{II}$ are as defined above;

a group —$(CH_2)_t$—$NH(SO_2)NH_2$, or —$(CH_2)_t$—$NH(SO_2)NHR^{II}$, or —$(CH_2)_t$—$NH(SO_2)NR^{II}R^{III}$, wherein t, $R^{II}$ and $R^{III}$ are as defined above, including the special case wherein $R^{II}$ and $R^{III}$ taken together with the nitrogen atom form an azaheterocyclyl ring;

a group —$(CH_2)_t$—NHC(=NH)$NH_2$, wherein t is as defined above;

a group —$(CH_2)_t$—CHO, wherein t is as defined above;

a group —$(CH_2)_t$—$C(O)R^{II}$, wherein t and $R^{II}$ are as defined above;

a group —$(CH2)_t$—$CO_2H$, wherein t is as defined above, or esters or amides thereof, i.e., —$(CH_2)_t$—$CO_2R^{II}$, —$(CH_2)_t$—$CONH_2$, —$(CH_2)_t$—$CONHR^{II}$, —$(CH_2)_t$—$CONR^{II}R^{III}$, wherein $R^{II}$ and $R^{III}$ are as defined above, including the special case wherein $R^{II}$ and $R^{III}$, taken together with the nitrogen atom form an azaheterocyclyl ring;

a group —$(CH_2)_t$—$SO_3H$, wherein t is as defined above;

a group —$(CH_2)_t$—$S(O)R^{II}$, wherein t and $R^{II}$ are as defined above;

a group —$(CH_2)_t$—$SO_2R^{II}$, wherein t and $R^{II}$ are as defined above;

a group —$(CH_2)_t$—$SO_2NH_2$, or —$(CH_2)_t$—$SO_2NHR^{II}$, or —$(CH_2)_t$—$SO_2NR^{II}R^{III}$, wherein t, $R^{II}$ and $R^{III}$ are as defined above;

$C_1$–$C_6$ alkyl or $C_2$–$C_6$ alkenyl;

$C_3$–$C_7$ cycloalkyl;

phenyl, biphenyl (i.e., —$C_6H_4$—$C_6H_5$), methylenedioxyphenyl, methylenedioxyphenylmethyl (hereinafter piperonyl), benzyl, phenethyl, phenpropyl, naphthyl, naphthylmethyl, naphthylethyl, naphthylpropyl, either unsubstituted or substituted by one to three substituents selected from by $C_1$–$C_4$ alkyl, hydroxy, $C_1$–$C_4$ alkoxy, amino, methylamino, dimethylamino, chloro and fluoro.

When present carboxy, hydroxy, mercapto and amino groups may be either free or in a protected form. Protected forms of said groups are any of those generally known in the art, as described, for example, by T. W. Greene in "Protective Groups in Organic Chemistry", Wiley Interscience. Preferably, carboxy groups are protected as esters thereof, in particular methyl, ethyl, tert-butyl, benzyl, and 4-nitrobenzyl esters. Preferably, hydroxy groups are protected as ethers or esters thereof, in particular methoxymethyl ethers, tetrahydropyranyl ethers, benzyl ethers, acetates, benzoates, pivalates. Preferably, mercapto groups are protected as thioethers or thioesters, in particular tert-butyl thioethers, thioacetates, thiobenzoates. Preferably, amino groups are protected as carbamates, e.g. tert-butoxycarbonyl and benzyloxycarbonyl derivatives, or as amides, e.g. acetamides and benzamides.

The present invention provides the salts of those compounds of formula (I) that have salt-forming groups, especially the salts of the compounds having an acid group, especially a carboxylic group, a N-hydroxycarbamoyl group, and a sulfo group, or the salts of the compounds having a basic group, especially an amino or guanidino group. The salts are especially physiologically tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable inorganic acids (e.g. hydrochlorides, hydrobromides, sulfates, phosphates) or carboxylic and sulfonic organic acids (e.g. acetates, trifluoroacetates, citrates, succinates, malonates, lactates, tartrates, fumarates, maleates, methanesulfonates, p-toluenesulfonates). Some compounds of formula (I) which contain a carboxylate and an ammonium group may exist as zwitterions; such salts are also part of the present invention.

Furthermore, hydrates, solvates of compounds of formula (I), and physiologically hydrolyzable derivatives (i.e., prodrugs) of compounds of formula (I) are included within the scope of the present invention. Particularly preferred prodrugs of the compounds of formula (I) are ester derivatives. They include esters of compounds of formula (I)

wherein W is —COOH, or wherein a carboxy group is present in any of the substituents $R_1$, $R_2$, $R_3$ and Q, which may be obtained by condensation of such carboxy group with a pharmaceutically acceptable alcohol, e.g. ethanol, or esters of compounds of formula (I) wherein a hydroxy group is present in any of the substituents $R_1$, $R_2$, $R_3$ and Q, which may be obtained by condensation of such hydroxy group with a pharmaceutically acceptable carboxylic acid, e.g. acetic acid, pivalic acid, benzoic acid and the like. Other particularly preferred prodrugs within the present invention are the cyclic condensation products between compounds of formula (I), wherein W is —CONHOH and $R_1$ is hydrogen, and formaldehyde, or an aldehyde of formula T—CHO, or a ketone of formula TT'CO, wherein T and T' are carbon radicals, such as tower alkyl, phenyl, benzyl, optionally substituted by one to three substituents selected from by $C_1$–$C_4$ alkyl, hydroxy, $C_1$–$C_4$ alkoxy, amino, methylamino, dimethylamino, chloro and fluoro. Such condensation products, which are represented herebelow, are obtained by mixing the two components, optionally in the presence of acid catalysts, as those employed for the formation of ketals from alcohols and ketones, and removing water by evaporation, azeotropically or by molecular sieves.

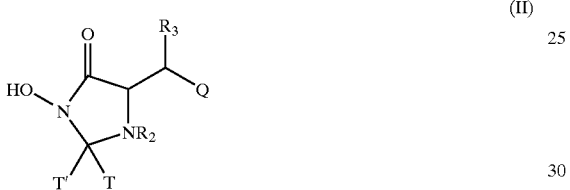

(II)

The present invention encompasses all the possible stereoisomers (e.g. diastereoisomers, epimers, geometrical isomers) of the compounds of formula (I), as well as their racemic or optically active mixtures.

The present invention also includes, within its scope, pharmaceutical compositions comprising one or more of the compounds (I) as active ingredients, in association with pharmaceutically acceptable carriers, excipients or other additives, if desirable.

Preferred compounds within the present invention have the structure (I'):

(I')

wherein:
W is —CONHOH or —COOH;
$R_1$ and $R_2$ are:
 both hydrogen; or
 both $C_1$–$C_4$ alkyl, still preferably methyl; or
$R_1$ is hydrogen or methyl, and $R_2$ is a group G which is:
 $C_1$–$C_{10}$ alkyl or $C_2$–$C_{10}$ alkenyl, either unsubstituted or substituted by $C_3$–$C_7$ cycloalkyl, or by one to three substituents selected from chloro, fluoro, hydroxy, $C_1$–$C_4$ alkoxy, $C_1$–$C_4$ alkyl, amino, methylamino, dimethylamino, —$CONH_2$, —$CONHCH_3$ or —$CONHC(CH_3)_3$, $C_1$–$C_4$ alkylthio, $C_1$–$C_4$ alkylsulfonyl, phenoxy, phenylthio and phenylsulfonyl, wherein the phenyl group may in turn be substituted by chloro, fluoro, methoxy or methyl; or
$C_3$–$C_7$ cycloalkyl; or
an aryl group, more preferably phenyl, methylenedioxyphenyl naphthyl or indanyl, each of which is optionally substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, phenyl, benzyl, phenethyl, phenpropyl, naphthyl and pyridyl, and wherein any phenyl, naphthyl and pyridyl ring may in turn be substituted by one to three substituents selected from chloro, fluoro, methyl, hydroxy, methoxy, amino, methylamino and dimethylamino, or
an unsaturated heterocyclyl group selected from pyrrolyl, pyrazolyl, imidazolyl, triazolyl, tetrazolyl, oxazolyl, isoxazolyl, thiazolyl, isothiazolyl, thiadiazolyl, thienyl, furyl, pyridyl, pyrazinyl, pyridazinyl, pyrimidinyl, benzothienyl, benzothiazolyl, benzoxazolyl, isobenzofuranyl, benzofuranyl, benzimidazolyl, indazolyl, chromenyl, indolyl, oxindolyl, quinolyl, isoquinolyl, isoindolyl, cinnolinyl and purinyl, each of which is optionally substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, wherein the phenyl ring may be substitued by chloro, fluoro, methoxy or methyl; or
a saturated or partially saturated heterocyclyl group selected from pyrrolidinyl, tetrahydrothienyl, tetrahydrofuryl, aziridinyl, oxiranyl, azetidinyl, piperidinyl, piperazinyl, hexahydropyridazinyl, tetrahydropyranyl, 1-oxo-2-isoindolyl, tetrahydroisoquinolyl, hydantoinyl, morpholinyl, thiomorpholinyl, dioxanyl, dithianyl, azepinyl and thiazolidinyl, wherein any ring nitrogen may be oxidized as an N-oxide, any ring carbon may be oxidized as a carbonyl, and any ring sulfur may be oxidized as a sulfoxide or sulfone; and the derivates thereof substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, wherein the phenyl ring may be substitued by chloro, fluoro, methoxy or methyl; or
$C_1$–$C_{10}$ alkyl, substituted by any of the unsaturated or saturated heterocyclyl groups as defined above, wherein any ring nitrogen may be oxidized as an N-oxide, any ring carbon may be oxidized as a carbonyl, and any ring sulfur may be oxidized as a sulfoxide or sulfone; or a derivative thereof substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, —$CONH_2$, —$CONHCH_3$ and —$CONHC(CH_3)_3$, $C_1$–$C_4$ alkylthio, $C_1$–$C_4$ alkylsulfonyl, phenoxy, phenylthio and phenylsulfonyl, wherein the phenyl ring may be substitued by chloro, fluoro, methoxy or methyl; or
$C_1$–$C_{10}$ alkyl, substituted by any of the aryl group as defined above, and the derivates thereof substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, wherein the phenyl ring may be substitued by chloro, fluoro, methoxy or methyl; or $R_1$ is hydrogen or methyl, and $R_2$ is —$SO_2$—G, wherein G is as defined above; or $R_1$ is hydrogen or methyl, and $R_2$ is —CO—G, wherein G is as defined above; or $R_1$ is hydrogen or methyl, and $R_2$ is —CO—O—G, wherein G is as defined above; or $R_1$ is hydrogen or methyl, and $R_2$ is —$SO_2$—$NH_2$, —$SO_2$—NHG or —$SO_2$—NGG', wherein G is as defined above and G', which is the same or different, is as defined above for G; or $R_1$ is hydrogen or methyl, and $R_2$ is —SO—NH—G, wherein 6 is as defined above; or $R_1$ is hydrogen or methyl, and $R_2$ is —CONHG or —CONGG', wherein G is as defined above and G', which is the same or different, is as defined above for G; or $R_1$ and $R_2$, taken together with the nitrogen atom to which they are attached, form a 3- to 7-membered azaheterocyclyl ring, optionally containing N, O, S or $SO_2$ as an additional ring member, which may be substituted by oxo on one or two carbon ring atoms adjacent to the linking nitrogen atom, and which is optionally fused with a benzene ring, the azaheterocyclyl group being either unsubstituted or substituted at one or more carbon and/or nitrogen atoms by chloro, fluoro, hydroxy, $C_1$–$C_4$ alkoxy, amino, methylamino, dimethylamino, $C_1$–$C_4$ alkyl, phenyl, 4-fluorophenyl, benzyl, 4-fluorobenzyl, alpha-methylbenzyl, methylenedioxyphenyl, 2-phenethyl, 2-(4-fluorophenyl)ethyl, piperonyl, carbamoyl, —$CONHCH_3$, —$CONHC(CH_3)_3$, —CONH-(4-fluorophenyl), —CONH-pyridyl, —CONH-(methylenedioxy)phenyl —CONH-piperonyl; or $R_1$ is hydrogen or methyl and $R_2$ is —$SO_2$-azaheterocyclyl, wherein azaheterocyclyl is as defined above; or $R_1$ is hydrogen or methyl, and $R_2$ is —CO-azaheterocyclyl, wherein azaheterocyclyl is as defined above;

$R_3$ is —$CH_2$-alkyl, —$(CH_2)_n$-cycloalkyl, —$(CH_2)_n$—O—alkyl, —$(CH_2)_n$—O—$(CH_2)_m$-cycloalkyl, —$(CH_2)_n$—O—$(CH_2)_m$-aryl, —$(CH_2)_n$—O—$(CH_2)_m$-heterocyclyl, —$(CH_2)_n$—S-alkyl, —$(CH_2)_n$—S—$(CH_2)_m$-cycloalkyl, —$(CH_2)_n$—S—$(CH_2)_m$-aryl, —$(CH_2)_n$—S—$(CH_2)_m$-heterocyclyl, —$(CH_2)_n$—SO-alkyl, —$(CH_2)_n$—SO—$(CH_2)_m$-cycloalkyl, —$(CH_2)_n$—SO—$(CH_2)_m$-aryl, —$(CH_2)_n$—SO—$(CH_2)_m$-heterocyclyl, —$(CH_2)_n$—$SO_2$-alkyl, —$(CH_2)_n$—$SO_2$—$(CH_2)_m$-cycloalkyl, —$(CH_2)_n$—$SO_2$—$(CH_2)_m$-aryl, —$(CH_2)_n$—$SO_2$—$(CH_2)_m$-heterocyclyl, —$(CH_2)_n$—CO-alkyl, —$(CH_2)_n$—CO—$(CH_2)_m$-cycloalkyl, —$(CH_2)_n$—CO—$(CH_2)_m$-aryl or —$(CH_2)_n$—CO—$(CH_2)_m$-heterocyclyl, wherein alkyl, cycloalkyl, aryl and heterocyclyl are as defined above, and n and m, being the same or different, are zero or an integer of 1 to 5, and wherein the alkyl, cycloalkyl, aryl and heterocyclyl groups are optionally substituted by one to three substituents selected from chloro, fluoro, cyano, cyanomethyl, hydroxy, $C_1$–$C_4$ alkoxy, $C_1$–$C_4$ alkyl, $C_1$–$C_4$ alkylthio, $C_1$–$C_4$ alkylsulfonyl, phenyl, tolyl, 4-chlorophenyl, 4-fluorophenyl, 4-methoxyphenyl, 4-phenoxyphenyl, 4-(4-pyridyl)oxyphenyl, pyridyl, or $R_3$ is selected from isobutyl, n-hexyl, n-heptyl, n-octyl, n-nonyl and cyclopentylmethyl; or $R_3$ is selected from 2-phenylethyl, 3-phenylpropyl, 4-phenylbutyl, 5-phenylpentyl, wherein the phenyl group is either unsubstituted or substituted by chloro, fluoro, cyano, cyanomethyl, methyl, ethyl, propyl, butyl, mesyl, methoxy, ethoxy, propoxy, butoxy, phenoxy, 4-chlorophenoxy, 4-fluorophenoxy, benzyloxy, phenyl, 4-fluorophenyl, 4-chlorophenyl, 4-methoxyphenyl, 4-cyanophenyl, 4-cyanomethylphenyl, 4-pyridyl, 4-pyridyloxy; or $R_3$ is selected from phenylsulfonylmethyl or phenylsulphonylethyl, wherein the phenyl group is either unsubstituted or substituted by chloro, fluoro, cyano, cyanomethyl, methyl, ethyl, propyl, butyl, methoxy, ethoxy, propoxy, butoxy, phenoxy, 4-chlorophenoxy, 4-fluorophenoxy, benzyloxy, phenyl, 4-fluorophenyl, 4-chlorophenyl, 4-methoxyphenyl, 4-cyanophenyl, 4-cyanomethylphenyl, 4-pyridyl, 4-pyridyloxy;

Q is:

a group —CONHG, —CONGG', —CONH—CHGG', —CON($CH_3$)—CHGG', —CONH—$CH_2$—CHGG', or —CON($CH_3$)—$CH_2$—CHGG', wherein G and G', being as defined above, are preferably selected from $C_1$–$C_6$ straight or branched alkyl, $C_5$–$C_6$ cycloalkyl, phenyl, tolyl, methylenedioxyphenyl, piperonyl and pyridyl, either unsubstituted or substituted by one to three substituents selected from chloro, fluoro, hydroxy, hydroxymethyl, $C_1$–$C_4$ alkoxy, amino, methylamino, dimethylamino, $C_1$–$C_4$ alkyl, $C_3$–$C_7$ cycloalkyl, —$CONH_2$, —$CONHCH_3$, —CONHC($CH_3$)$_3$, —CONH(4-fluorophenyl), —CONH-pyridyl, —CONH-(methylenedioxy)phenyl, —CONH-piperonyl, carbomethoxy, carbethoxy, or a keto group —CO—$R''$, wherein $R''$, being as defined above, is selected from $C_1$–$C_4$ alkyl, phenyl, fluorophenyl, chlorophenyl, methylenedioxyphenyl, naphthyl, piperonyl, or a sulfone —$(CH_2)_n$—$SO_2$—$R''$, wherein n and $R''$ are as defined above, or a sulfonamide —$(CH_2)_n$—$SO_2$—$NH_2$, —$(CH_2)_n$—$SO_2NHR''$, —$(CH_2)_n$—$SO_2$—$NR''$ $R'''$, wherein n, $R''$ and $R'''$ are as defined above, including the special case wherein $R''$ and $R'''$, taken together with the nitrogen atom to which they are attached, constitute an azaheterocyclyl ring, as defined above; or a group —CO-azaheterocyclyl, wherein azaheterocyclyl, being as defined above, is, either unsubstituted or substituted by one to three substituents selected from hydroxy, hydroxymethyl, $C_1$–$C_4$ alkoxy, carbamoyl, carbomethoxy, carbethoxy, mesyl, $C_1$–$C_6$ linear or branched alkyl, trifluoromethyl, $C_3$–$C_7$ cycloalkyl, aryl, heterocyclyl and aryl-($C_1$–$C_3$)alkyl or heterocyclyl-($C_1$–$C_3$)alkyl; or said azaheterocyclyl group is substituted by a group —CONH—$R''$, wherein $R''$, being as defined above, is selected from methyl, isopropyl, tert-butyl, cyclopropyl, cyclopentyl, cyclohexyl, phenyl, 4-fluorophenyl, 4-chlorophenyl, 4-methoxyphenyl, 3,4-difluorophenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, methylenedioxyphenyl, piperonyl, 2-benzimidazolyl and 5-tetrazolyl; or said azaheterocyclyl group is substituted by a keto group —CO—$R''$, or by a carbinol group of formula —CH(OH)—R″, wherein R″, being as defined above, is selected from $C_1$–$C_4$ alkyl, phenyl, fluorophenyl, chlorophenyl, methylenedioxyphenyl, naphthyl, piperonyl, or by a sulfone —$(CH_2)_n$—$SO_2$—R″, wherein n and R″ are as defined above, or by a sulfonamide —$(CH_2)_n$—$SO_2$—$NH_2$, —$(CH_2)_n$—$SO_2$—NHR″, —$(CH_2)_n$—$SO_2$—NR″ R‴, wherein n, R″ and R‴ are as defined above, including the special case wherein R″ and R‴, taken together with the nitrogen atom to which they are attached, constitute an azaheterocyclyl ring, as defined above;
and the salts and solvates thereof.

When, in the above embodiment $R_1$ and $R_2$ form an azaheterocyclyl ring, the azaheterocyclyl ring is preferably selected from aziridine, azetidine, morpholine, thiomorpholine, piperidine, pyrrolidine, piperazine, thiazolidine, tetrahydroisoquinoline, hexahydropyridazine, succinimido, phthalimido, saccharinyl, hydantoinyl, and oxoisoindolinyl. When $R_2$ is —CO-azaheterocyclyl or —$SO_2$-azaheterocyclyl, the azaheterocyclyl moiety is preferably morpholino or piperidino. When Q is a group —CO-azaheterocyclyl, the azaheterocyclyl moiety is preferably selected from azetidine, morpholine, thiomorpholine, pyrrolidine, piperidine. piperazine, pyridazine, thiazolidine, tetrahydroisoquinoline, hexahydropyridazine and hexamethylenimine. The aryl group or moiety in the definitions of Q is preferably selected from phenyl, 4-fluorophenyl, 4-methoxyphenyl, 4-methylphenyl, methylenedioxyphenyl, naphthyl, and heterocyclyl is preferably pyridyl.

A further preferred group of compounds are cyclic acetonide prodrugs of formula (II'):

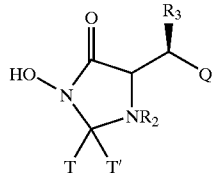

(II')

wherein $R_2$, $R_3$ and Q are as defined above and T is methyl or a hydrogen atom, and T' is methyl, $C_2$–$C_4$ lower alkyl, phenyl, benzyl, optionally substituted by one to three substituents selected from by $C_1$–$C_4$ alkyl, hydroxy, $C_1$–$C_4$ alkoxy, amino, methylamino, dimethylamino, chloro and fluoro. More preferably, T and T' are methyl.

The present invention also provides a pharmaceutical composition comprising a pharmaceutically acceptable diluent or carrier and, as an active ingredient, a compound of the invention as defined above.

Compounds of the general formula (I) may be prepared by any suitable method known in the art, and/or by the following processes, which form another aspect of the invention. In the description and formulae below, the groups W, $R_1$, $R_2$, $R_3$ and Q are as defined above. It is understood that in the processes below any functional group (e.g. carboxyl, hydroxyl or amino), if needed or desired, can be masked by conventional methods and unmasked at the end or when convenient. Suitable protecting groups for such functionalities will be apparent to those skilled on the art and are well described in the chemical literature (see. for example: "Protective Groups in Organic Synthesis" by T. W. Greene, Wiley Interscience). It is also understood that any of the groups W, $R_1$, $R_2$, $R_3$ and Q can be converted by conventional methods into different groups W, $R_1$, $R_2$, $R_3$ and Q having any of the meaning previously defined, if desired, at the end or at any stage of the processes below. These conversions are known or will be apparent to those skilled in the art and are well described in the chemical literature (see, for example: "Comprehensive Organic Transformation" by R. C. Larock, VCH Publishers).

A preferred process for preparing a compound of formula (I) comprises:

(a) reacting a beta-lactam compound of formula (III):

(III)

wherein $R_2$ and $R_3$ are as defined above, and W' is COOH, CONHOH or a protected derivative thereof, with:

a primary or secondary acyclic amine of formula G—$NH_2$, GG'NH, GG'CH—$NH_2$, GG'CH—$NHCH_3$, GG'CH—$CH_2$—$NH_2$, or GG'CH—$CH_2$—$NHCH_3$, wherein G and G' are as defined above; or a cyclic saturated or unsaturated secondary amine, represented as azaheterocyclyl-H, wherein azaheterocyclyl is as defined above; to obtain a compound of formula (IV):

(IV)

wherein W', $R_2$, $R_3$ and Q are as defined above; and then:

(b) converting said compound of formula (IV) into a compound of formula (I), wherein W, $R_1$, $R_2$, $R_3$ and Q are as defined above; and then:

(c) if desired, removing the protecting groups and/or, if desired, converting any of the groups W, $R_1$, $R_2$ $R_3$ and Q into different groups W, $R_1$, $R_2$, $R_3$ and Q at the end or at any stage of the process.

It is evident that compounds with a desired configuration may be prepared starting from compounds (III) and (IV) with the appropriate configurations. Thus, a process for preparing preferred compounds of formula (I') comprises:

(a') reacting a beta-lactam compound of general formula (m'):

(III')

wherein $R_2$ and $R_3$ are as defined above, and W' is either COOH, CONHOH, or a protected derivative thereof, with an amine as defined above, to obtain a compound of formula (IV'):

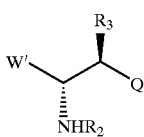

wherein W', R$_2$, R$_3$ and Q are as defined above; and (b') converting this compound of formula (IV') into a compound of formula (I'):

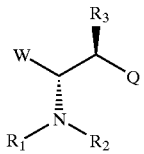

wherein W, R$_1$, R$_2$, R$_3$ and Q are as defined above.

The reaction between the beta-lactam of formula (III) or (III') and an amine among those hereabove detailed in step (a) or (a') above can be carried out in organic solvents, especially dimethylformamide (hereinafter DMF), tetrahydrofuran (hereinafter THF), acetonitrile, dimethylsulfoxide (hereinafter DMSO) and toluene, or in aqueous organic solvents, especially aqueous THF, aqueous DMF, and aqueous acetonitrile, at temperatures ranging from 0 to 120° C., either in the absence or in the presence of external bases. When the amine is a poor nucleophile, in order to accelerate the reaction, and achieving higher yields of the product of formula (IV) or (IV'), the reaction can be run in the presence of nucleophiles (NuH or salts thereof, wherein Nu is herebelow defined), which cleave the beta-lactam of formula (III) or (III') more readily. In this case, an intermediate of formula (IIIa) or (III'a) is formed:

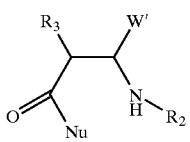

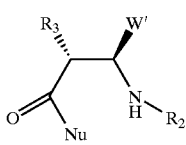

wherein W', R$_2$ and R$_3$ are as defined above, and Nu is selected from the group consisting of azido, imidazole, cyano, lower alkylthio, pyridylthio, phenylthio, and benzylthio. Said intermediate of formula (IIIa) or (IIIa'), being an activated carboxylic acid derivative, reacts in the same milieu or in a separate step, and under the same reaction conditions, with the amine selected among those detailed above, giving rise to the product of formula (IV) or (IV'). Particularly preferred external nucleophiles are sodium azide, imidazole, and sodium and potassium cyanide; particularly preferred solvents are DMF and acetonitrile.

When in compounds of formula (III), (III'), (IV), (IV') above W' is a protected carboxy derivative, it is preferably benzyloxycarbonyl, p-nitrobenzyloxycarbonyl, p-methoxybenzyloxycarbonyl, tert-butoxycarbonyl, benzhydryloxycarbonyl, trityloxycarbonyl, trimethylsilyloxycarbonyl, tert-butyldimethylsilyloxycarbonyl, phenyl-dimethyl-silyloxycarbonyl, allyloxycarbonyl, methoxycarbonyl, ethoxycarbonyl and n-butoxycarbonyl. When in compounds of formula (III), (III'), (IV), (IV') above W' is a protected derivative of CONHOH, it is preferably a group of formula CONHOR$_{10}$ or CON(R$_{11}$)OR$_{10}$, wherein R$_{10}$ and R$_{11}$ are, respectively, hydroxy- and amino-protecting groups, known per se and removable by hydrogenolysis or by hydrolysis. Preferred R$_{10}$ and R$_{11}$ groups, which may be the same or different, include benzyl, p-methoxybenzyl, p-nitrobenzyl, trimethylsilyl, tert-butyl, tert-butoxycarbonyl, tetrahydropyranyl, and trityl.

The conversion of a compound of formula (IV) or (IV') into a compound of formula (I) or (I') in step (b) above may include any or all of the following steps in any order:

(b$^i$): the conversion of the group W', which is a protected carboxy or hydroxamate derivative, into a group W, which is the unmasked carboxy or hydroxamic acid. This conversion is carried out by methodologies for unmasking of protective groups, which are well known in the art, as generally referred to above. A preferred conversion of this type is hydrogenolysis, especially in the presence of a palladium catalyst, in an inert organic solvent such as ethanol or DMF or the like, especially at room temperature and under atmospheric pressure or moderate pressure, which is suitable for the conversion, e.g., of benzyl and p-nitrobenzyl esters into the parent carboxylic acids, or of O-benzyl and O,N-bis-benzyl hydroxamates into the parent hydroxamic acids. Another preferred conversion of this type is acid hydrolysis, especially by trifluoroacetic acid, hydrochloric acid, or by aluminium trichloride, in the presence or absence of anisole, in inert organic solvents such as THF, acetonitrile and the like, especially between −20 and +30° C., which is suitable for the conversion, e.g., of tert-butyl esters and p-methoxybenzyl esters into the parent carboxylic acids, or of O-tert-butylhydroxamates, O-(p-methoxybenzyl)-hydroxamates, and O,N-bis(p-methoxybenzyl)hydroxamates into the parent hydroxamic acids. A further preferred conversion of this type is alkalyne hydrolysis, especially by NaOH, KOH, LiOH, KOSi(CH$_3$)$_3$, in an inert organic solvent or in water or in admixtures thereof, which is particularly suitable for the conversion of lower alkyl esters, e.g. the methyl, ethyl and n-butyl esters, into the parent carboxylic acids.

(b$^{ii}$): the conversion of the group W', which is carboxy or an activated derivative thereof, into a group W, which is —CONHOH. This conversion entails the condensation of such compounds of formula. (IV) with hydroxylamine or a salt thereof, or with an O-protected hydroxylamine of formula R$_{10}$O—NH$_2$, or an N,O-diprotected hydroxylamine of formula R$_{10}$O—NHR$_{11}$, wherein R$_{10}$ and R$_{11}$ are as defined above, or a salt thereof, and then removal of said protecting groups R$_{10}$ and R$_{11}$, if present, according to (b$^i$) above. Such condensation is carried out according to general methodologies for the conversion of carboxylic acids or activated derivatives thereof into hydroxamic acids, which are well known in the art. In particular, activated derivatives of the carboxy group are the acid chloride, mixed anhydrides, and esters. In particular, the acid chloride is obtained by reacting the acid or a salt thereof with reagents such as oxalyl chloride or thionyl chloride; mixed anhydrides are obtained by reacting the acid or a salt thereof with chlorocarbonates, such as ethyl chlorocarbonate, or with acid halides, such as pivaloyl chloride; esters, which are, preferably, the methyl, ethyl, n-butyl, pentafluorophenyl, hydroxysuccinyl, or hydroxybenzotriazolyl esters, are obtained by reaction of the acid with the corresponding alcohols in the presence of a dehydrating agent, for example dicyclohexyl carbodiimide (hereinafter DCC), N,N-dimethylaminopropyl-N'-ethyl carbodiimide (EDC), and 2-ethoxy-1-ethoxycarbonyl-1,2-dihydroquinoline (EEDQ). Esters, in particular the methyl, ethyl, and n-butyl esters, may be present from the beginning in the azetidinone intermediates of formula (III) and (III') above. An O-protected hydroxylamine is, preferably, O-benzylhydroxylamine, O-tert-butylhydroxylamine, O-tert-butyldiphenylsilyl hydroxyamine, O-(4-methoxybenzyl)-hydroxylamine, O-(4-nitrobenzyl)hydroxylamine, O-trimethylsilyl-hydroxylamine, and O-(tert-butoxycarbonyl) hydroxylamine. An N,O-diprotected hydroxylamine is, preferably, N,O-bis(benzyl)hydroxylamine, N,O-bis(4-methoxybenzyl)hydroxylamine, N,O-bis(tert-butoxycarbonyl)hydroxylamine, N-(tert-butoxycarbonyl)-O-(tert-butyldimethylsilyl) hydroxylamine, and N-(tert-butoxycarbonyl)-O-(tetrahydropyranyl)hydroxylamine. Preferably, the condensation reaction with hydroxylamine, O-protected hydroxylamines, N,O-diprotected hydroxylamines, and the salts thereof, is carried out in an inert organic solvent, such as DME, THF, acetonitrile, dichloromethane, toluene and the like, at temperatures ranging from −20 to +60° C., optionally in the presence of a tertiary organic base, such as triethylamine and N-methylmorpholine. When protected hydroxylamines are employed, the protecting groups are removed after the condensation reaction, under the conditions described in ($b^i$) above;

($b^{iii}$): the conversion of the group $NHR_2$, being $R_2$ different from hydrogen, into a group $NH_2$. This reaction can be carried out on compounds of formula (I), (I'), or on intermediates of formula (IV), (IV'), wherein $R_2$ is an amino protecting group, according to methods well known per se, for example by the methods of removal of amino protecting groups which are part of the techniques of peptide chemistry. Particularly preferred $R_2$ groups for such conversion are electron-withdrawing groups, in particular alkoxy- or benzyloxy-carbonyl groups such as tert-butoxycarbonyl, benzyloxycarbonyl and 4-nitro or 4-methoxy derivatives thereof, since the same particular $R_1$ groups efficiently assist the beta-lactam cleavage reaction detailed in step (a) above. In a preferred embodiment of the present invention, $R_2$ is tert-butoxycarbonyl, which can be removed by treatment with trifluoroacetic acid (TFA), optionally in the presence of anisole, in an inert organic solvent; in another preferred embodiment, $R_2$ is benzyloxycarbonyl or 4-nitrobenzyloxycarbonyl, which can be removed by catalytic hydrogenation;

($b^{iv}$): the conversion of the group $NHR_2$, including the special case wherein $R_2$ is hydrogen, into a group $NR_1R_2$, to be selected within the specifications stated above. Preferred $R_1$ and $R_2$ groups are the same groups detailed for the preferred compounds of formula (I). Such conversion encompasses functionalizations of amino groups well known in the art, such as alkylation, acylation, sulfonylation, and the like, and is performed according to methods well known per se. In a preferred embodiment of the present invention, such conversion is performed on compounds of formula (IV) or (IV') wherein W' is protected carboxy, thereafter removing the protecting group to obtain a compound of formula (I) or (I') wherein W is carboxy, by the general methodology described under ($b^i$) above and, optionally, by converting the so-obtained compound of formula (I) or (I') wherein W is carboxy into the corresponding compound wherein W is —CONHOH, by the general methodology described under ($b^{ii}$) above, ($b^v$): the conversion of any group W, $R_1$, $R_2$, $R_3$ and Q into any different group $R_1$, $R_2$, $R_3$ and Q, to be selected within the specifications stated above, by methodologies known per se. The resultant compounds of formula (I) or (I') may be converted into the desired salts, prodrugs, hydrates or solvates thereof by means of well known reactions, which include salt preparation by reaction with a pharmaceutically acceptable acid, or conversion of any hydroxy or carboxy group into an ester thereof if desired, by condensation with a pharmaceutically acceptable alcohol or with a pharmaceutically acceptable carboxylic acid. In the particular case of the cyclic prodrugs described by formula (II) or (II'), said compounds are obtained from the corresponding compounds of formula (I) or (I') wherein W is —NHOH and $R_1$ is hydrogen, by reaction with an aldehyde of general formula T—CHO or a ketone of general formula TT'CO, wherein T and T' are as defined above, and removing water by evaporation.

The amines used in step (a) above are known compounds or are prepared from known compounds by known methods.

The beta-lactams of formula (III) or (III') above are known compounds or can be prepared from known compounds by methodologies known per se or by analogy with the specific preparative examples herein. In particular, a preferred preparation of compounds of formula (III) or (III') includes:

($d^i$): cyclization of an aspartic acid derivative to obtain a compound of formula (III) or (III') wherein $R_3$ is hydrogen, by reaction with a suitable condensing agent;

($d^{ii}$): conversion of a compound of formula (III) or (III') wherein $R_3$ is hydrogen into a compound of formula (III) or (III') wherein $R_3$ is as described above, by deprotonation with a strong base and alkylation of the resulting beta-lactam enolate with an agent of formula $R_3$—X, wherein X is halo, e.g. chloro, bromo or iodo, or sulfonyloxy, e.g. triflate, mesylate or the like.

General conditions for step ($d^i$) above are described in the literature, the preferred aspartic acid derivative being usually dibenzyl aspartate or di(4-nitro)benzyl aspartate. Some of the resultant azetidinones (III) or (III') wherein $R_3$ is hydrogen, W' is carboxy or an ester thereof, and $R_2$ is hydrogen or tert-butyldimethylsyl are also commercially available. A preferred compound in step ($d^{ii}$) is a compound of formula (III) or (III') wherein $R_3$ is hydrogen, $R_2$ is tert-butyldimethylsilyl, and W' is free carboxy, since the carboxylate anion helps at avoiding racemization at the azetidinone 4-C, and increases regioselectivity of alkylation by the $R_3$—X reagent at the azetidinone 3-C.

The conditions described in steps (a), (b), (c) and (d) do not usually promote epimerization or racemization at pre-existing chiral centers. Thus, when the aspartic acid derivative used as a reagent in step ($d^i$) above is an L-aspartic acid derivative, the reaction affords a chiral azetidinone of formula (III'), wherein $R_3$ is hydrogen and $R_2$, W' are as described above. In such chiral azetidinone of formula (III')

wherein $R_3$ is hydrogen, the configuration at the C-4 atom addresses stereoselective alkylation, by the $R_3$—X reagent, in a transoid relationship with the W' substituent. Therefore, starting from such intermediates of formula (III'), step (d$^{ii}$) above stereoselectively affords the corresponding azetidinones of formula (III') wherein $R_3$, being as described above, is different from hydrogen, with the depicted configurations at the two chiral centers. Said configurations of the two chiral centers are the same as found in compounds of formula (I') herein specifically preferred. Accordingly, it can be appreciated that steps (d$^i$) and (d$^{ii}$) above are essential part of an original, fully stereocontrolled route to the compounds of formula (I').

Another process for the preparation of compounds of formula (I) comprises:

(e) alkylation of an aspartic acid derivative of formula (V):

(V)

wherein W' is either carboxy or a protected derivative thereof, Q' is either Q as described above, or carboxy or protected carboxy, and $R_1$, $R_2$ are as described above, with a reagent of formula $R_3$—X, wherein $R_3$ and X are as described above, to obtain a compound of formula (VI):

(VI)

wherein W', $R_1$, $R_2$, $R_3$ and Q' are as described above; and:

(f) conversion of such compound of formula (VI) into the desired compound of formula (I), wherein W, $R_1$, $R_2$, $R_3$ and Q are as described above.

We have observed that the configuration at the chiral carbon atom in compounds of formula (V) addresses the configuration at the new chiral center in the product of formula (VI) in an anti-fashion, exclusively or predominantly. Thus, starting from an L-aspartic derivative of formula (V'):

(V')

wherein W', $R_1$, $R_2$, $R_3$ and Q' are as described above, step (e) predominantly or exclusively affords a compound of formula (VI'):

(VI')

wherein W', $R_1$, $R_2$, $R_3$ and Q' are as described above, from which the preferred compounds of formula (I') are obtained by step (f) above.

The reaction of step (e) above is carried out according to conventional carbanion chemistry, i.e. with 2–4 equivalents of a strong base, such as LDA and the like, in aprotic organic solvents, such as THF, DMF, N-methylpyrrolidone, HMPA and the like, at temperatures ranging from −70° C. to room temperature. A preferred W' group is free carboxy. A preferred $R_1$ group is hydrogen. A preferred $R_2$ group is tert-butoxycarbonyl. Preferred Q' groups are either the acyclic or cyclic tertiary carboxamides described within Q above, or a carboxy ester, which in step (f) can be converted into the group Q above as generally known for the preparation of carboxamides.

The compounds of formula (I) and (I') provided by the present invention are characterized by high inhibitory activity on matrix metalloproteinases (MMPs), especially collagenases, gelatinases and stromelysins. For example, the following protocol was used to assess the biochemical activity of compounds of formula (I') against MMP-1, MMP-2, and MMP-3 (respectively, human interstitial collagenase, gelatinase A, and stromelysin-1).

Biochemical Assay (Protocol A)

Human collagenase (MMP-1) was obtained as truncated recombinant enzyme encompassing residues 101–269 and did not require activation. Human gelatinase-A (MMP-2) was obtained as pro-enzyme (72 kDa) and was activated with 1 mM 4-aminophenylmercuric acetate for 30 min at 37° C. immediately prior to use. Human stromelysin-1-255 (MMP-3) was obtained as a recombinant pro-enzyme isolated from *E. coli* and activated by heat (1 h, 55° C.).

The substrate was the commercial quenched-fluorescence peptide Mca-Pro-Leu-Gly-Leu-Dpa-Ala-Arg-NH$_2$, that is (7-methoxycoumarin4-yl)Acetyl-Pro-Leu-Glv-Leu-(3-[2,4-dinitrophenyl]-L-2,3-diamino-propionyl)-Ala-Arg-NH$_2$ (C. G. Knight et al., FEBS Lett.296:263, 1992). The enzymes cleave at the Gly-Leu bond, removing the internally quenching Dpa group. Release of the highly fluorescent peptide Mca-Pro-Leu was followed fluorimetrically at 37° C. using a Perkin Elmer LS-50 Fluorescence Spectrophotometer fitted with a thermostatted four position stirring cell changer. The excitation wavelength was set at 326 nm (bandwidth 5 nm) and the emission at 392 nm (bandwidth 20 nm). Km values of this substrate for the three MMP's is 70 μM or more (Knight et al., reference above). Substrate concentration was 2 μM in the tests, so that we could approximate to unit the term (1+[substrate]/K$_M$) in calculations. The substrate was stable for over 60 minutes in the assay conditions, giving no appreciable increment of fluorescence. Full response was adjusted against 200 nM Mca-Pro-Leu-OH (the released fluorescent peptide) and the instrument was calibrated in the range 0–100 nM Mca-Pro-Leu-OH, corresponding to 0–5% extent of hydrolysis of the 2 μM substrate. The aqueous assay buffer was 50 mM Tris/HCl pH=7.4 containing 0.15 M NaCl, 10 mM CaCl$_2$, 0.01 mM ZnCl$_2$ and 0.05% Brij 35. The concentration of the activated enzyme was determined by titration against representative inhibitors described in the literature and synthesized in house: Roche Ro31-9790 (N. G. Knebel et al., J. Chromatogr. B 673:213, 1995) for MMP-1, and Celltech CT-1418 (compound 1 in S. K. Chander, J. Pharm. Sci. 84:404, 1995) for MMP-2 and MMP-3. Enzyme concentrations in the tests were set at 1.0 nM for MMP-1, 0.04 nM for MMP-2, and 3.0 nM for M-3. Under our assay conditions, we measured $k_{cat}/K_M$ values of 26900, 669000 and 9740 1/(M×s) for MMP-1, MMP-2 and MMP-3, respectively. All the three enzymes were found stable for over three hours in the assay conditions.

The inhibition constant for compounds of the present invention was measured at steady state (Ki*; see J. F. Morrison and C. T. Walsh, Adv. Enzymol. Relat. Areas Mol. Biol. 61:201, 1988), upon preincubation experiment, by measuring $V_0$, the initial rate in the absence of inhibitor, and $V_s$, the steady-state velocity, at different concentrations of inhibitors in the region of their enzyme-inhibitor dissociation constants.

On a routine basis, 1.94 mL of assay buffer was pre-heated at 37° C. in a vial, 0.02 mL of inhibitor in DMSO (or DMSO only), and 0.02 ml of 100 nM MMP-1 or 4 nM MMP-2 or 300 nM MMP-3 were added, mixed, and the vial was held at 37° C. for 5–180 minutes. Then 0.02 ml of 0.2 mM substrate was added, mixed and transferred into a pre-heated cell. The sample was allowed to equilibrate in the cuvette for 3–5 min at 37° C. against small changes in temperature and changes in the enzyme-inhibitor equilibria related to addition of substrate. After that, the linear increase of fluorescence was monitored over 3–5 min, and the slope (Vo or Vs) was obtained. Inhibitor concentrations were varied to collect data over Vs/Vo ratio ranging from 0.05 to 0.95. The values of Ki* were calculated by nonlinear weighted regression to the tight-binding equation according to Morrison and Walsh above:

$$Vs/Vo=[1/(2 \times Et)] \times SQR[(Ki^*+It-Et)^2+4 \times Ki^* \times Et]-(Ki^*+It-Et)$$

wherein Et is the total enzyme concentration, and It is the total inhibitor concentration. The following Table I lists Ki* obtained for some representative examples:

TABLE 1

Ki at steady state (Ki*) for inhibition of MMP-1, MMP-2 and MMP-3 (all micromolar)

| Example compound | MMP-1 | MMP-2 | MMP-3 |
|---|---|---|---|
| Example 2 | 1.1 | 2.8 | 13 |
| Example 3 | 0.088 | 0.29 | 2.5 |
| Example 5 | 0.061 | 0.31 | 0.94 |
| Example 7 | 0.070 | 0.25 | 0.72 |
| Example 10 | 0.18 | 0.34 | 2.2 |
| Example 12 | 0.041 | 0.19 | 0.38 |
| Example 15 | 17 | 0.63 | 6.5 |
| Example 16 | 6.4 | 0.094 | 2.4 |
| Example 17 | 9.4 | 0.61 | 4.3 |
| Example 18 | 0.85 | 0.079 | 0.86 |
| Example 19 | 4.5 | 0.23 | 1.1 |
| Example 20 | 2.0 | 0.04 | 0.39 |
| Example 22 | 0.015 | 0.067 | 0.73 |
| Example 23 | 0.003 | 0.016 | 0.145 |
| Example 24 | 0.17 | 0.40 | 11 |
| Example 25 | 0.076 | 0.19 | 2.3 |
| Example 26 | 0.071 | 0.10 | 0.60 |
| Example 27 | 0.0065 | 0.02 | 0.24 |
| Example 28 | 7.5 | 0.60 | 10 |
| Example 30 | 0.0036 | 0.025 | 0.27 |
| Example 32 | 2.6 | 0.037 | 0.50 |
| Example 33 | >10 | 0.46 | 6.6 |
| Example 34 | 2.4 | 0.021 | 1.4 |
| Example 35 | 0.0029 | 0.008 | 0.031 |
| Example 37 | 0.0018 | 0.0026 | 0.035 |
| Example 39 | 0.76 | 0.09 | 0.806 |
| Example 42 | 1.4 | 0.016 | 0.76 |
| Example 44 | 0.0089 | 0.0023 | 0.21 |
| Example 47 | 0.0046 | 0.028 | 0.14 |
| Example 50 | 0.026 | 0.058 | 0.49 |
| Example 61 | 0.0078 | 0.066 | not determined |

Some of the compounds of formula (I) were also shown to possess high activity at inhibiting the release of TNF of several different cell lines, under different stimulation conditions. For example, the following cell-based assay was used to assess such activity:

Cellular Assay (Protocol B)

THP-1 cells, cultured in RPMI 1640 supplemented with 10% FCS, were distributed into 24-well plates, 1 mL of a suspension of $1 \times 10^6$ cells/mL in each well. Compounds to be tested, dissolved in DMSO and diluted with the culture medium (1% final DMSO concentration) were added. Plates were incubated for 30 min at 37° C. in 5% $CO_2$, and lipopolisaccharide (LPS 0111:B4, 5 µg/ml) was added as a stimulant. After a further 4 h incubation, cells were harvested, centrifuged (2,000 rpm, 7 min), and the surnatant was collected and freezed (−20° C.) until analysis. Analysis was run by classical ELISA methodology (monoclonal anti-TNF-a antibody, rabbit capture policlonal antibody, and peroxidated anti-rabbit antibody). Dichloroisocoumarin was used as a standard. As anticipated above, low aqueous solubility, metabolic instability (high clearance) and poor oral bioavailability is a common problem for the "peptide-based" hydroxamates of the prior art. In these respects, the compounds of the present invention are usually characterised by a superior profile. As an example, Table 2 reports the solubility in water for some representative compounds, detailed in the Examples.

TABLE 2

Aqueous solubility (mg/mL, 25° C.) of some representative compounds

| Example compound | Conditions[1] | Solubility |
|---|---|---|
| Example 2 | A | >4.5 |
| Example 3 | A | >9.5 |
| Example 5 | B | >6.0 |
| Example 7 | A | 4.0 |
| Example 13 | A | 6.71 |
| Example 14 | B | >14 |
| Example 16 | B | >9.6 |
| Example 18 | B | >9.6 |
| Example 19 | A | 7.5 |
| Example 22 | B | >8.2 |
| Example 27 | B | 7.1 |

As a further example, Table 3 reports clearance and AUC values measured after intravenous administration to rats of a 10–15 mg bolus dose of some representative compounds of the present invention.

TABLE 3

PK parameters in rats (iv route, 10–15 mg/kg) of some representative compounds

| Example compound | Clearance (mL/min/kg) | AUC (µg.min/mL)[1] |
|---|---|---|
| Example 10 | 24 | 666 |
| Example 12 | 39 | 395 |
| Example 19 | 27 | 563 |
| Example 27 | 23 | 679 |

As an additional example, Table 4 reports the maximum plasma concentration ($C_{max}$) and oral bioavailability (% F; calculated from dose-normalised ratio of oral to i.v. mean AUC values) after oral administration to rats or cynomolgus monkeys of a 10–15 mg single dose of some representative compounds of the present invention.

TABLE 4

PK parameters (oral route, 10–15 mg/kg) of some representative compounds

| Example compound | Animal species | $C_{max}$ (ng/mL)[1] | % F |
|---|---|---|---|
| Example 10 | rat | 2120 | 28 |
| Example 12 | rat | 2440 | 21 |
| Example 22 | rat | 5487 | 62 |
| Example 27 | rat | 7908 | 58 |
| Example 27 | cynomolgus monkey | 3132 | 34 |
| Example 50 | rat | 3146 | 50 |
| Example 50 | cynomolgus monkey | 49516 | 70 |

Compounds of formula (I) can be used in human or veterinary medicine in the form of pharmaceutical preparations which contain them in association with a compatible pharmaceutical carrier material. Thus, a distinct aspect of the present invention is the preparation of pharmaceutical compositions carrying a compound of formula (I) as active ingredient, and a method of management (i.e. treatment or prophylaxis) of diseases or conditions mediated in humans and warm blood animals by MMPs and/or TACE, which method comprises administering an effective amount of a compound of formula (I) above, or a pharmaceutically acceptable salt thereof.

In particular, the compounds of formula (I) can be administered:

A) Orally, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid, binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil liquid paraffin, or olive oil. Aqueous suspensions contain the active materials in admixture with excipients suitable for the manufacture of aqueous suspensions. Such excipients are suspending agents, for example, sodium carboxymethylcellulose, methylcellulose, hydroxy propylmethylcellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavoring agents, or one or more sweetening agents, such as sucrose or saccharin. Oily suspension may be formulated by suspending the active ingredient in a vegetable oil, for example arachis oil, olive oil, sesame oil or coconut oil or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables, C) By inhalation, in the form of aerosols or solutions for nebulizers, D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams ointments, jellies, solutions or suspensions.

Daily doses are in the range of about 0.1 to about 50 mg per kg of body weight, according to the activity of the specific compound, the age, weight and conditions of the subject to be treated, the type and severity of the disease, and the frequency and route of administration; preferably, daily dosage levels for humans are in the range of 10 mg to 2 g. The amount of active ingredient that may be combined with the carrier materials to produce a single dosage form will vary depending upon the host treated and the particular mode of administration. For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 5 mg to about 1 g of active ingredient.

Pharmaceutical compositions containing a compound of formula (I) can be used in medicine for the treatment of disease states characterised by a systemic or local imbalance of active MMPs and their natural inhibitors. The rationale for the use of MMP inhibitors in medicine has been illustrated above, and is well described in the recent literature, see, for example, D. E. Levy & A. M. Ezrin, "Matrix Metalloproteinase Inhibitor Drugs", in: Emerging Drugs: The Prospect for Improved Medicines, Chapter Ten (pp 205–230), Ashley Publications Ltd., 1997. According to this rationale, and proofs of concept already established with other MMP inhibitors, the compounds of the present invention can be used, in particular, for the treatment of:

inflammatory and autoimmune diseases, especially rheumatoid arthritis, osteoarthritis, bone resorption, periodontal disease, multiple sclerosis, inflammatory bowel diseases;

cancer, including both tumor growth and tumor invasion by secondary metastases, with particular reference to breast cancer, small cell lung cancer, non-small cell lung cancer, glioblastoma, prostate cancer, ovarian cancer, gastric and esophageal cancers, pancreatic cancer, colorectal tumors, and bony metastases;

angiogenic disorders, especially diabetic retinopathies and macular diseases, cardiovascular diseases, especially congestive hearth failure and vascular restenosis;

soft and osseous tissue diseases, including ocular inflammation, corneal or tissue ulceration, wound healing;

other disorders in which either MMs or abnormal release of TNF-alfa is implicated, in particular shock syndromes, transplant rejection, cachexia, anorexia. The present invention also includes the use of compounds of formula (I), for the treatment of any of the diseases above, as adjuncts to other conventional treatments; for example, together with anti-inflammatory or immunosuppressive drugs for the treatment of rheumatoid arthritis and multiple sclerosis, and together with cytotoxic or cytostatic drugs for the treatment of tumoral diseases.

The following examples are meant to illustrate the present invention, without limiting it.

EXAMPLE 1

(3S-tert-Butoxycarbonylamino-4-hydroxy-2R-isobutyl)succinyl-piperidinamide

Azetidinone Route

Step A

Piperidine (1.6 mL) was added to a solution of 4S-benzyloxycarbonyl-1-tert-butoxycarbonyl-3R-isobutylazetidin-2-one (3.8 g; see Preparation A) in acetonitrile (15 mL). After three hours stirring at room temperature, the solvent was removed in vacuo and the residue, dissolved in EtOAc, was sequentially washed with saturated aqueous $NH_4Cl$ and brine. Drying over $Na_2SO_4$, evaporation and flash chromatography over silica gel (n-hexane/EtOAc) afforded (4-benzyloxy-3S-tert-butoxycarbonylamino-2R-isobutyl)succinyl-piperidinamide as a yellow oil (3.6 g). FT-IR ($CHCl_3$) 3433 br (NH), 1753 (ester CO), 1714 (carbamate CO), 1626 (amide CO) $cm^{-1}$. $H^1$-NMR (200 MHz, $CDCl_3$) 0.89 and 0.91 (two d, 6 H, J=6.6 Hz); 1.42 (s, 9 H); 1.2–1.8 (m, 9 H); 3.1–3.5 (m, 5 H); 4.48 (dd, 1 H, J=4.1 and 10.0 Hz); 5.06 and 5.19 (two d, 2 H, J=12.4 Hz); 6.45 (d, 1 H, J=10.0 Hz); 7.32 (m, 5 H) ppm.

Step B

A mixture of (4-benzyloxy-3S-tert-butoxycarbonylamino-2R-isobutyl)succinyl-piperidin-amide (500 mg) and 10% Pd/C (100 mg) in EtOH (20 mL) was exposed to a hydrogen atmosphere for 3 hours. The catalyst was removed by filtration (Celite filter aid), washed with additional ethanol, and the solvent was removed in vacuo to leave the title compound (390 mg) as a colourless oil. $H^1$-NMR (200 MHz, $CDCl_3$) 0.89 and 0.90 (two d, 6 H J=6.1 Hz) 1.44 (s, 9 H); 1.4–1.8 (m, 9 H); 3.60 (m, 5 H); 4.29 (dd, 1 H, J=1.9 and 4.9 Hz); 5.92 (d, 1 H, J=4.9 Hz) ppm. FAB-MS 379 $(MNa)^+$, 357 $(MH)^+$, 301, 257, 211, 112, 86, 84, 57 m/z.

Aspartic Route

Starting from N-tert-butoxycarbonyl-3R-isobutyl-L-aspartic acid 1-benzyl ester4-piperidin-amide, obtained as described in Preparation H, which is (4-benzyloxy-3S-tert-butoxycarbonylamino-2R-isobutyl)succinyl-piperidin-amide, identical with the compound obtained as in step A bove, and following the same procedure described in step B above, the title product was obtained, identical with the one described above.

EXAMPLE 2

(3S-tert-Butoxycarbonylamino-4-hydroxyamino-2R-isobutyl)succinyl-piperidinamide

Step A (3S-tert-Butoxycarbonylamino-4-hydroxy-2R-isobutyl)succinyl-piperidinamide (390 mg), obtained as indicated in Example 1, was dissolved in $CH_3CN$ (20 mL) and treated with O-benzylhydroxylamine hydrochloride (230 mg) and N-methylmorpholine (0.33 ml). After 10 min, TBTU (O-1H-benzotriazol-1-yl-N,N,N',N'-tetramethyluronium tetrafluoroborate; 465 mg) was added to the solution, and the mixture was let stir overnight at room temperature. The solvent was removed in vacuo and the residue, dissolved in $CH_2Cl_2$, was washed with 4% aqueous $NaHCO_3$, 2% HCl and brine. The organic layer was dried over $Na_2SO_4$ and evaporated. The crude product was purified by flash cromatography on silica gel (n-hexane/EtOAc) to afford (4-benzyloxyamino-3S-tert-butoxycarbonylamino-2R-isobutyl)succinyl-piperidinamide as an oil (500 mg). $H^1$-NMR (200 MHz. $CDCl_3$) 0.90 and 0.92 (two d, 6 H, J=6.4 Hz); 1.57 (s, 9 H); 1.3–1.7 (m, 9 H); 4.32 (dd, 1H, J=3.4 and 8.2 Hz); 4.85 (s, 2 H); 6.73 (d, 1 H, J=8.5 Hz); 7.37 (m, 5 H); 9.13 (s, 1 H) ppm. ESI-MS 500 $(MK)^+$, 484 $(Mna)^+$, 462 $(MH)^+$, 384, 362, 283, 239, 211, 112 m/z.

Step B

A mixture of (4-benzyloxyamino-3S-tert-butoxycarbonylamino-2R-isobutyl)succinyl-piperidinamide (500 mg) and 10% Pd/C (100 mg) in EtOH (50 mL) was exposed to a hydrogen atmosphere for 1 hour. The catalyst was removed by filtration (Celite filter aid) and the solvent was evaporated to leave the title compound (300 mg) as a white solid. $H^1$-NMR (200 MHz, $CDCl_3$) 0.90 and 0.93 (two d, 6 H, J=6.1 Hz); 1.45 (s, 9 H); 1.2–1.8 (m, 9 H); 3.3–3.7 (m, 5 H); 4.43 (dd, 1 H, J=3.4 and 8.3 Hz); 6.72 (d, 1 H, J=8.3 Hz); 6.93 (br signal, 1 H); 9.31 (br signal, 1 H) ppm. FAB-MS 372 $(MH)^+$, 316, 283, 272, 211, 112, 86, 84, 57 m/z.

EXAMPLE 3

(3S-Amino-4-hydroxyamino-2R-isobutyl)succinyl-piperidinamide (3S-tert-Butoxycarbonylamino-4-hydroxyamino-2R-isobutylsuccinyl-piperidinamide (170 mg; prepared as described in Example 2) was dissolved in 95% aqueous trifluoroacetic acid (3 mL), and the solution was stirred 2 hours at room temperature. Toluene was added and evaporated in vacuo (several times), thereby obtaining the title compound, trifluoroacetate salt, as a white solid (115 mg). In DMSO solution, the compound is present as a mixture of two rotamers (M, major; m, minor). $H^1$-NMR (400 MHz, DMSO-$d_6$) 0.80 and 0.81 (two d, 6 H, J=6.4 Hz); 1.1–1.6 (m, 9 H); 3.21 (m, 1 H); 3.40 (m, 4 H); 3.64 (d, 1 H, J=7.3 Hz); 8.02 (br signal, 3 H); 9.32 (s, 1 H, M); 9.80 (br signal, 1 H, m); 10.69 (s, 1 H, m); 11.12 (br signal, 1 H, M) ppm. ESI-MS 294 $(MNa)^{30}$, 272 $(MH)^+$, 239, 112 m/z.

EXAMPLE 4

(3S-N,N-Dimethylamino-4-hydroxy-2R-isobutyl)succinyl-piperidinamide

Step A (4-Benzyloxy-3S-tert-butoxycarbonylamino-2R-isobutyl)succinyl-piperidinamide (prepared as described Example 1, step A; 1 g) was dissolved in 95% aqueous trifluoroacetic acid (5 mL), and the solution was stirred 2 hr at room temperature. Toluene was added and evaporated in vacuo, repeating the process several times, thereby obtaining (3S-amino-4-benzyloxy-R-isobutyl)succinyl-piperidinamide (triflluoroacetate salt) as a yellow oil (1 g).

Step B

Sodium cyanoborohydride (230 mg) was added to a solution of (3S-amino-4-benzyloxy-2R-isobutyl)succinyl-piperidinamide trifluoroacetate salt (700 mg) in MeOH (10 mL). After 10 min, 37% aqueous formaldehyde was added dropwise, and the solution was stirred for 1 hour at room temperature. The solvent was removed in vacuo and the residue was dissolved in EtOAc; the organic layer was washed with water and dried over $Na_2SO_4$. Evaporation of the solvent left crude (4-benzyloxy-3S-N,N-dimethylamino-2R-isobutyl)succinyl-piperidinamide (552 mg). $H^1$-NMR (200 MHz, $CDCl_3$) 0.80 and 0.82 (two d, 6 H, J=6.6 Hz); 0.92 and 1.70 (two m, 2 H); 1.40 (m, 1 H); 1.6 (m, 6 H); 2.25 (s, 6 H); 3.30 (m, 1 H); 3.50 (m, 4 H); 3.56 (d, 1 H, J=10.8 Hz); 5.15 and 5.20 (two d, 2 H, J=12.2 Hz); 7.36 (m, 5 H) ppm.

Step C (4-Benzyloxy-3S-N,N-dimethylamino-2R-isobutyl)succinyl-piperidinamide (550 mg), as the crude product from step B above, was dissolved in EtOH (15 mL). The resulting solution was treated with 10% Pd/C (100 mg) and exposed to a hydrogen atmosphere for 4 hours. The catalyst was removed by filtration (Celite filter aid), washing with additional EtOH. The solvent was removed in vacuo to leave the title compound (400 mg) as a yellow oil. FT-IR (KBr) 3385 br (NH), 1622 br (CO) $cm^{-1}$. ESI/CID-MS 307 $(MNa)^+$, 285 $(MH)^+$, 239 $(M—COOH)^+$, 184, 102 m/z.

EXAMPLE 5

(3SN,N-Dimethylamino-4-hydroxyamino-2R-isobutyl)succinyl-piperidinamide

Step A (3S-N,N-Dimetylamino-4-hydroxy-2R-isobutyl)succinyl-piperidinamide (460 mg), prepared as described in Example 4 (step B), was dissolved in $CH_3CN$ (10 mL) and treated with O-benzylhydroxylamine hydrochloride (310 mg) and N-methylmorpholine (0.44 mL). After 10 min, TBTU (663 mg) was added to the solution, and the mixture was let stir overnight at room temperature. The solvent was removed in vacuo and the residue, dissolved in EtOAc, was washed with aqueous $NaHCO_3$ and brine. The organic layer was dried over $Na_2SO_4$ and evaporated to afford the crude product. Purification by flash chromatography on silica gel (n-hexane/EtOAc) afforded a white solid (230 mg), consisting of (4-benzyloxyamino-3S-N,N-dimethylamino-2R-isobutyl)succinyl-piperidinamide. FT-IR (KBr) 3191 br (NH), 1683 br (CO) $cm^{-1}$. $H^1$-NMR (400 MHz, DMSO-$d_6$) 0.75 and 0.80 (two d, 6 H, J=6.4 Hz); 0.9–1.6 (m, 9 H); 2.09 (s, 6 H); 2.97 (d, 1 H, J=10.7 Hz) 3.30 (m, 1 H); 3.3–3.6 (m, 4 H); 4.79 and 4.82 (two d, 2 H, J=12.0 Hz); 7.36 (m, 5 H); 11.13 (s, 1 H) ppm. ESI-MS 412 $(MNa)^+$, 390 $(MH)^+$, 305, 239, 207 m/z.

Step B

The material from step A above (230 mg) and 10% Pd/C (50 mg) in EtOH (10 mL) was exposed to a hydrogen atmosphere for 1 hour. The catalyst was removed by filtration (Celite filter aid) and the solvent was evaporated to leave the title compound as a white solid (170 mg). $H^1$-NMR (400 MHz, DMSO-$d_6$) 0.77 and 0.81 (two d, 6 H, J=6.7 Hz); 0.9–1.6 (m, 9 H); 2.13 (s, 6 H); 3.00 (d, 1 H, J=10.8 Hz); 3.30 (m, 1 H); 3.3–3.7 (m, 4 H); 8.83 (s, 1 H); 10.51 (s, 1 H) ppm. ESI-MS 322 (MNa)$^+$, 300 (MH)$^+$, 239 (M—HONHCO), 117 m/z.

EXAMPLE 6

(4-Hydroxy-3S-(4-methoxyphenylsulfonyl)amino-2R-isobutyl)succinyl-piperidinamide Step A (3S-Amino-4-benzyloxy-2R-isobutyl)succinyl-piperidinamide trifluoroacetate salt (prepared as described in Example 4, step B; 660 mg) was dissolved in $CH_2Cl_2$ (100 mL). To this solution, (4-methoxybenzenesulfonyl)chloride (350 mg) and triethylamine (0.5 mL) were added. After 24 hours, the solution was washed with saturated aqueous $NH_4Cl$, saturated aqueous $NaHCO_3$ and brine. The organic layer was dried over $Na_2SO_4$ and evaporated to afford a crude product, which was purified by flash cromatography over silica gel (n-hexane/EtOAc) to give (4-benzyloxy-3S-(4-methoxyphenylsulfonyl)amino-2R-isobutyl)succinyl-piperidinamide (340 mg) as a white solid. $H^1$-NMR (200 MHz, $CDCl_3$) 0.86 and 0.90 (two d, 6 H, J=6.1 Hz) 1.2–1.8 (m, 9 H); 3.0–3.5 (m, 5 H); 3.81 (s, 3 H); 4.20 (dd, 1 H, J=3.9 and 9.8 Hz); 4.90 (s, 2 H); 6.72 (d, 1 H, J=9.8 Hz); 6.82 (d, 2 H, J=9.0 Hz); 7.30 (m, 5 H); 7.75 (d, 2 H, J=9.0 Hz) ppm. ESI-MS 555 (MH)$^+$, 539 (MNa)$^+$, 454, 112, 91 m/z.

Step B

The material from step A above (340 mg) and 10% Pd/C (70 mg) were suspended in a mixture of EtOH and THF (1:1; 30 mL) and stirred under a hydrogen atmosphere for 2 hours. The catalyst was removed by filtration (Celite filter aid) and the solvent was evaporated, to leave the title compound as a white solid (245 mg). $H^1$-NMR (400 MHz, $CDCl_3$) 0.91 and 0.94 (two d, 6 H, J=6.4 Hz) 1.2–1.8 (m, 9 H); 3.5–3.8 (m, 6 H); 3.84 (s, 3 H); 6.00 (br signal, 1 H); 6.95 (d, 2 H, J=9.0 Hz); 7.71 (d, 2 H, J=9.0 Hz) ppm. ESI-MS 465 (MK)$^+$, 449 (MNa)$^+$, 427 (MH)$^+$, 364, 196 m/z.

EXAMPLE 7

(4-Hydroxyamino-3S-(4-methoxyphenylsulfonyl)amino-2R-isobutyl)succinyl-piperidin-amide Step A (4-Hydroxy-3S-(4-methoxyphenylsulfonyl)amino-2R-isobutyl)succinyl-piperidlnamide (245 mg; Example 6) was dissolved in $CH_3CN$ (20 mL) and treated with O-benzylhydroxylamine hydrochloride (110 mg) and N-methylmorpholine (0.16 mL). After 10 min, TBTU (220 mg) was added, and the mixture was stirred overnight at room temperature. The solvent was removed in vacuo and the residue was dissolved in EtOAc and washed with saturated aqueous $NaHCO_3$, 2% aqueous HCl and brine. The organic layer was dried over $Na_2SO_4$ and evaporated to afford a crude product which was purified by flash cromatography on silica gel (n-hexane/EtOAc) to obtain a white solid (300 mg), consisting of (4-benzyloxyamino-3S-(4-methoxyphenylsulfonyl)amino-2R-isobutyl)succinyl-piperidinamide. $H^1$-NMR (200 MHz, $CDCl_3$) 0.71 and 0.72 (two d, 6 H, J=6.3 Hz); 0.8–1.7 (m, 9 H); 3.3–3.6 (m, 5 H); 3.81 (dd, 1 H, J=6.6 Hz); 4.80 and 4.83 (two d, 2 H, J=9.0 Hz); 6.94 (d, 2 H, J=9.0 Hz); 7.14 (d, 1 H, J=6.4 Hz); 7.39 (m, 5 H), 7.76 (d, 2 H, J=9.0 Hz); 9.65 (br signal, 1 H) ppm. ESI/CID-MS 570 (MK)$^+$, 554 (MNa)$^+$, 469 (MH)$^+$, 403, 381, 171, 112, 91 m/z.

Step B

The material from step A above (300 mg) and 10% Pd/C (100 mg) were suspended in EtOH (20 mL) and stirred under a hydrogen atmosphere for 3 hr at room temperature. The catalyst was removed by filtration (Celite filter aid), washing with additional EtOH. The solvent was removed in vacuo to give the title compound (210 mg) as white solid. $H^1$-NMR (400 MHz, $CDCl_3$) 0.70 and 0.71 (two d, 6 H, J=6.4 Hz); 0.9–1.7 (m, 9 H); 3.3–3.7 (m, 5 H); 3.86 (s, 3 H); 3.89 (dd, 1 H, J=3.0 and 6.6 Hz); 6.98 (d, 2 H, J=9.0 Hz); 7.23 (d, 1 H, J=6.6 Hz); 7.82 (d, 2 H, J=9.0 Hz); 9.79 (br signal, 1 H) ppm. ESI-MS 480 (MK)$^+$, 464 (MNa)$^+$, 442 (MH)$^+$, 409, 381, 171 m/z.

EXAMPLE 8

(3S-tert-Butoxycarbonylamino-4-hydroxy-2R-isobutyl)succinyl-morpholinamide

Step A

In a manner analogous to that described in Example 1 (step A), (3S-tert-butoxycarbonylamino-2R-isobutyl4-(4-nitrobenzyloxycarbonyl))succinyl-morpholinylamide (190 mg) was obtained as a yellow oil starting from 1-tert-butoxycarbonyl-3R-isobutyl-4S-p-nitrobenzyloxycarbonylazetidin-2-one (200 mg) and morpholine (0.08 mL). FT-IR ($CHCl_3$) 3432 br (NH), 1750–1713 br (ester and carbamate CO), 1630 (amide CO) cm$^{-1}$. $H^1$-NMR (400 MHz, $CDCl_3$) 0.92 and 0.98 (two d, 6 H); 1.2–1.7 (m, 3 H); 1.44 (s, 9 H); 6.4–3.7 (m, 9 H); 4.58 (dd, 1 H, J=4.1 and 10.0 Hz); 5.21 and 5.26 (two d, 2 H, J=13.7 Hz); 6.36 (d, 1 H, J=10.0 Hz); 7.50 (d, 2 H, J=9.5 Hz); 8.20 (d, 2 H, J=9.5 Hz) ppm.

Step B

In a manner analogous to that described in Example 1 (step B), from the material of step A above (500 mg), with 10% Pd/C (50 mg) and under a hydrogen atmosphere, the title compound was obtained (290 mg) as a white solid. FT-IR (KBr) 3411 br (NH,OH), 1750–1714 br (acid and carbamate CO), 1630 (amide CO) cm$^{-1}$. $H^1$-NMR (200 MHz, DMSO-$d_6$) 0.82 and 0.83 (two d, 6 H, J=6.0 Hz); 1.2–1.6 (m, 3 H); 1.36 (s, 9 H); 3.2–3.6 (m, 9 H); 4.11 (dd, 1 H, J=9.4 Hz); 6.41 (d, 1 H, J=9.4 Hz); 12.80 (br signal, 1 H) ppm. FD-MS 358 (MH)$^+$, 313 (MH—COOH)$^+$, 259 m/z.

EXAMPLE 9

(3S-tert-Butoxycarbonylamino-4-hydroxyamino-2R-isobutyl)succinyl-morpholinamide

Step A

In a manner analogous to that described in Example 2 (step A), reaction of (3S-tert-butoxycarbonylamino-4-hydroxy-2R-isobutyl)succinyl-morpholinamide (290 mg) with O-benzylhydroxylamine hydrochloride (154 mg), N-methylmorpholine (0.22 mL) and TBTU (0.97 mg) afforded (4-benzyloxyamino-3S-tert-butoxycarbonylamino-2R-isobutyl)succinyl-morpholinamide (300 mg) as a white solid. $H^1$-NMR (400 MHz, $CDCl_3$) 0.91 and 1.11 (two d, 6 H, J=6.2 Hz); 1.3–1.6 (m, 3 H); 1.4 (s, 9 H); 3.4–3.8 (m, 9 H); 4.32 (dd, 1 H, J=3.2 and 8.2 Hz); 4.86 (s, 2 H); 6.64 (d, 1 H, J=8.2 Hz); 7.37 (m, 5 H); 9.12 (s, 1 H) ppm.

Step B

In a manner analogous to that described in Example 2 (step B), from the material of step A above (300 mg) and 10% Pd/C (60 mg), under a hydrogen atmosphere, the title compound was obtained as white solid (240 mg). $H^1$-NMR (400 MHz, $CDCl_3$) 0.90 and 0.92 (two d, 6 H, J=6.7 Hz); 1.2–1.7 (m, 3 H); 1.45 (s, 9 H); 3.3–3.8 (m, 8 H); 3.55 (m, 1 H); 4.43 (m, 1 H); 6.63 (d, 1 H, J=8.2 Hz); 7.20 (br signal, 1 H); 9.34 (br signal, 1 H) ppm. FAB-MS 374 (MH)$^+$, 318, 285, 274, 213, 114, 88, 57 m/z.

EXAMPLE 10

(3S-Amino-4-hydroxyamino-2R-isobutyl)succinyl-morpholinamide

In a manner analogous to that described in Example 3, reaction of (3 S-tert-butoxycarbonylamino-4-hydroxyamino-2R-isobutyl)succinyl-morpholinamide (100 mg) with 95% aqueous trifluoroacetic acid afforded the title compound, trifluoroacetate salt, as a white solid (100 mg). In DMSO solution. the compound is present as a mixture of two rotamers (M, major; m, minor). H$^1$-NMR (400 MHz, DMSO-d$_6$) 0.78 and 0.79 (two d, 6 H, J=6.4 Hz); 1.15–1.5 (two m, 2 H); 1.35 (m, 1 H); 3.1–3.7 (m, 10 H); 8.10 (br signal, 3 H); 9.35 (s, 1 H, M); 9.80 (s, 1 H, m); 10.72 (s, 1 H, m); 11.13 (br signal, 1 H, M) ppm. FAB-MS 274 (MH)$^+$, 213 (M—HONHCO)$^+$, 114, 89, 88 m/z.

EXAMPLE 11

(4-Hydroxy-2R-isobutyl-3S-(4-toluenesulfonyl)amino)succinyl-morpholinamide

Step A

3R-Isobutyl-4S-p-nitrobenzyloxycarbonyl-1-(4-toluenesulfonyl)-azetidin-2-one (300 mg; see Preparation B) was dissolved in dry DMF (15 mL). To this solution, morpholine (0.11 mL) and sodium azide (30 mg) were sequentially added. After overnight stirring at room temperature, the solvent was partially removed in vacuo and the residue, taken up in EtOAc, was sequentially washed with saturated aqueous NH$_4$Cl and brine. Drying over Na$_2$SO$_4$, evaporation, and flash cromatography over silica gel (n-hexane/EtOAc) afforded (2R-isobutyl-4-p-nitrobenzyloxycarbonyl-3S-(4-toluenesulfonyl)amino)succinyl-morpholinamide (290 mg) as a white solid. FT-IR (CHCl$_3$) 3410 br (NH), 1736 (ester CO), 1674 (amide CO) cm$^{-1}$. H$^1$-NMR (400 MHz, CDCl$_3$) 0.80 and 0.88 (two d, 6 H, J=6.4 Hz); 1.2–1.6 (m, 3 H); 2.36 (s, 3 H); 3.3–3.7 (m, 9 H); 4.27 (dd, 1 H, J=4.1 and 9.7Hz); 4.98 and 5.08 (two d, 2 H, J=13.5 Hz); 6.67 (d, 1 H, J=9.7 Hz); 7.19 (d, 2 H, J=8.2 Hz), 7.36 (d, 2 H, J=8.8 Hz); 7.71 (d, 2 H, J=8.2 Hz); 8.18 (d, 2 H, J=8.8 Hz) ppm.

Step B

In a manner analogous to that described in Example 1 (step B), from the material of step A above (290 mg), with 10% Pd/C (50 mg) under a hydrogen atmosphere, the title compound was obtained as an amorphous solid (200 mg). H$^1$-NMR (400 MHz, CDCl$_3$) 0.90 and 0.93 (two d, 6 H), 1.5 (m, 3 H); 2.40 (s, 3 H); 3.5–3.9 (m, 10 H); 6.36 (d, 1 H, J=3 Hz); 7.29 (d, 2 H, J=8.1 Hz); 7.66 (d, 2 H, J=8.1 Hz) ppm. FAB-MS 413 (MH)$^+$, 367 (MH—COOH)$^+$, 259, 213, 155, 114, 88 m/z.

EXAMPLE 12

(4-Hydroxyamino-2R-isobutyl-3S-(4-toluenesulfonyl)amino)succinyl-morpholinamide

Step A

In a manner analogous to that described in Example 7 (step A), reaction of (4-hydroxy-2R-isobutyl-3S-(4-toluenesulfonyl)amino)succinyl-morpholinamide (200 mg) with O-benzylhydroxylamine hydrochloride (93 mg), N-methylmorpholine (0.13 mL) and TBTU (186 mg) afforded (4-benzyloxyamino-2R-isobutyl-3S-(4-toluenesulfonyl)amino)succinyl-morpholinamide (176 mg) as a white solid. H$^1$-NMR (400 MHz, CDCl$_3$) 0.67 and 0.68 (two d, 6 H, J=6.4 Hz); 0.8–1.2 (m, 3 H); 2.42 (s, 3 H); 3.3–3.8 (m, 10 H); 4.80 and 4.86 (two d, 2 H, J=10.8 Hz); 7.04 (d, 1 H, J=6.4 Hz); 7.30 (d, 2 H, J=8.6 Hz); 7.39 (m, 5 H); 7.72 (d, 2 H, J=8.6 Hz); 9.53 (s, 1 H) ppm.

Step B

In a manner analogous to that described in Example 7 (step B), from the material of step A above (170 mg) with 10% Pd/C (50 mg) under hydrogen atmosphere, the title compound was obtained as a white solid. H$^1$-NMR (400 MHz, DMSO-d$_6$) 0.67 and 0.70 (two d, 6 H, J=6.8 Hz); 1.1–1.5 (m, 3 H); 2.30 (s, 3 H); 3.0–3.6 (m, 9 H); 3.72 (m, 1 H); 10.74 (s, 1 H) 8.1 Hz); 7.53 (d, 2 H, J=8.1 Hz); 7.89 (d, 1 H, J=9.4 Hz); 8.82 (s, 1 H), 10.74 (s, 1 H) ppm. FAB-MS 428 (MH)$^+$, 371,367 (M—HONHCO)$^+$, 241, 129, 114, 57 m/z.

EXAMPLE 13

(3S-tert-Butoxycarbonylamino-4-hydroxy-2R-(4-methoxy)phenpropyl)succinyl-morpholinamide Step A In a manner analogous to that described in Example 1 (step A), reaction of 4S-benzyloxycarbonyl-1-tert-butoxycarbonyl-3R-(4-methoxy)phenpropyl)azetidin-2-one (600 mg; see Preparation C) with morpholine (0.23 mL) afforded (4-benzyloxy-3S-tert-butoxycarbonylamino-2R-(4-methoxy)phenpropyl)succinyl-morpholinamide as a yellow oil (700 mg). H$^1$-NMR (400 MHz, DMSO-d$_6$) 1.41 (s, 9 H); 1.4–1.8 (m, 4 H); 2.54 (m, 2 H); 3.1–3.5 (m, 8 H); 3.25 (m, 1 H), 3.76 (s, 3 H); 4.53 (dd, 1 H, J=3.8 and 9.8 Hz); 5.02 and 5.19 (two d, 2 H, J=12.4 Hz); 6.28 (d, 1 H, J=9.8 Hz); 6.78 (d, 2 H, J=8.6 Hz); 7.03 (d, 2 H, J=8.6 Hz); 7.31 (s, 5 H) ppm.

Step B

In a manner analogous to that described in Example 1 (step B), from the material of step A above (700 mg) with 10% Pd/C (100 mg), under a hydrogen atmosphere, the title compound was obtained as a white solid (600 mg). FT-IR (KBr) 3400 br (OH,NH), 1710 (acid CO), 1700 (carbamate CO), 1650 (amide CO) cm$^{-1}$. H$^1$-NMR (400 MHz, CDCl$_3$) 1.43 (s, 9 H); 1.6 (m, 4 H); 2.52 (m, 2 H); 3.3–3.8 (m, 9 H); 3.76 (s, 3 H); 4.32 (dd, 1 H, J=1.7 and 5.0 Hz); 6.04 (d, 1 H, J=5.0 Hz); 6.80 (d, 2 H, J=8.5 Hz); 7.02 (d, 2 H, J=8.5 Hz) ppm. ESI-MS 473 (MNa)$^+$, 451 (MH)$^+$, 395, 351 (M-BOC)$^+$ m/z.

EXAMPLE 14

(3S-Amino-4-hydroxy-2R-(4-methoxy)phenpropyl)succinyl-morpholinamide (33S-tert-Butoxycarbonylamino-4-hydroxy-2R-(4-methoxy)phenpropyl)succinyl-morpholinamide (obtained as described in Example 13; 50 mg) was dissolved in 95% aqueous trifluoroacetic acid (2 mL), and the solution was stirred 2 hours at room temperature. Toluene was added and evaporated in vacuo to afford the title compound as a white solid (58 mg). H$^1$-NMR (400 MHz, DMSO-d$_6$) 1.4–1.6 (m, 4 H); 2.48 (m, 2 H); 3.2–3.6 (m, 9 H); 3.70 (s, 3 H); 3.91 (d, 1 H, J=4.1 Hz); 6.82 (d, 2 H, J=8.5 Hz); 7.09 (d, 2 H, J=8.5 Hz); 8.1 (br signal, 2 H) ppm. ESI-MS 373 (MNa)$^+$, 351 (MH)$^+$, 305 (M—COOH)$^+$, 236, 191 m/z.

EXAMPLE 15

(3S-tert-Butoxycarbonylamino-4-hydroxyamino-2R-(4-methoxy)phenpropyl)succinyl-morpholinamide Step A In a manner analogous to that described in Example 2 (step A), reaction of (3S-tert-butoxycarbonylamino-4-hydroxy-2R-(4-methoxy)phenpropyl)succinyl(-morpholinamide (310 mg; obtained as described in Example 13) with O-benzylhydroxylamine hydrochloride (132 mg), N-methylmorpholine (0.2 mL) and TBTU (263 mg) afforded (4-benzyloxyamino-3S-tert-butoxycarbonylamino-2R-(4-methoxy)phenpropyl)succinyl-morpholinamide as a white solid (300 mg). FT-IR (KBr) 3208 br (NH), 1710–1667 br (CO), 1632 (amide CO) cm$^+$. H$^1$-NMR (400 MHz, CDCl$_3$) 1.38 (s, 9 H); 1.5–1.8 (m, 4 H); 2.52 (m, 2 H); 3.3–3.8 (m, 9 H); 3.76 (s, 3 H); 4.33 (dd, 1 H, J=3.0 and 8.0 Hz); 4.83 (s, 2 H); 6.63 (d, 1 H, J=8.0 Hz); 6.79 (d, 2 H, J=8.5 Hz); 7.03 (d, 2 H, J=8.5 Hz); 7.35 (m, 5 H); 9.14 (s, 1 H) ppm. ESI-MS 578 (MNa)$^+$, 555 (MH)$^+$, 500, 456, 377, 305 m/z.

Step B

In a manner analogous to that described in Example 2 (step B), from the material of step A above (300 mg), with 10% Pd/C (50 mg) under a hydrogen atmosphere, the title compound was obtained as pinkish solid (250 mg). FT-IR (CHCl$_3$) 3254 br (NH,OH), 1712–1614 br (CO) cm$^{-1}$. H$^1$-NMR (400 MHz, CDCl$_3$) 1.44 (s, 9 H); 1.4–1.8 (m, 4 H); 2.54 (m, 2 H); 3.3–3.8 (m, 9 H); 3.78 (s, 3 H); 4.46 (dd, 1 H, J=3.0 and 8.1 Hz);6.63 (d, 1 H, J=8.1 Hz); 6.81 (d, 2 H, J=8.5 Hz); 7.05 (d, 2 H, J=8.5 Hz); 7.6 (br signal, 1 H); 8.43 (br signal, 1 H) ppm. ESI-MS 488 (MNa)$^+$, 466 (MH)$^+$, 410, 377, 366, 305 m/z.

EXAMPLE 16

(3S-Amino-4-hydroxyamino-2R-(4-methoxy)phenpropyl)succinyl-morpholinamide

In a manner analogous to that described in Example 3, reaction of (3S-tert-butoxycarbonylamino-4-hydroxyamino-2R-(4-methoxy)phenpropyl)succinyl-morpholinylamide (200 mg; obtained as described in Example 15) with 95% aqueous trifluoroacetic acid (2 mL) afforded the title compound, trifluoroacetate salt, as a white solid (154 mg). The compound is present in DMSO solution as a mixture of two rotamers (M, major; m, minor). H$^1$-NMR (400 MHz, DMSO-d$_6$) 1.42 (m, 4 H); 2.41 (m, 2 H); 3.14 (m, 1 H); 3.2–3.6 (m, 8 H); 3.66 (s, 3 H); 3.72 (m, 1 H); 6.79 (d, 2 H, J=8.5 Hz); 7.03 (d, 2 H, J=8.5 Hz); 8.0 (br signal, 3 H, m); 8.15 (br signal, 3 H, M); 9.39 (br signal, 1 H, M); 9.79 (br signal, 1 H, m), 10.72 (s, 1 H, m); 11.15 (s, 1 H, M) ppm. ES/CID-MS 366 (MH)$^+$, 305 (M—HONHCO), 218, 121, 114, 88 m/z.

EXAMPLE 17

(3S-tert-Butoxycarbonylamino-4-hydroxyamino-2R-(4-methoxy)phenpropyl)succinyl-piperidinamide Step A In a manner analogous to that described in Example 1 (step A), reaction of 4S-benzyloxycarbonyl-1-tert-butoxycarbonyl-3-(4-methoxy)phenpropyl)azetidin-2-one (350 mg; see Preparation D) with piperidine (0.15 mL) afforded (4-benzyloxycarbonyl-3S-tert-butoxycarbonylamino-2R-(4-methoxy)phenpropyl)succinyl-piperidinamide as a yellow oil (400 mg). FT-IR (CHCl$_3$) 3400 br (NH), 1730 (ester CO), and 1641 br (carbamate and amide CO) cm$^{-1}$. H$^1$-NMR (200 MHz, CDCl$_3$) 1.2–1.8 (m, 10 H); 1.55 (s, 9 H); 2.55 (m, 2 H); 3.1–3.4 (m, 5 H); 3.78 (s, 3 H); 4.52 (dd, 1 H, J=4.1 Hz); 5.06 and 5.18 (two d, 2 H, J=12.4 Hz ); 6.43 (d, 1 H, J=9.8 Hz); 6.81 (d, 2 H, J=8.5 Hz); 7.06 (d, 2 H, J=8.5 Hz); 7.32 (s, 5 H) ppm. ESI-MS 561 (MNa)$^+$, 539 (MH)$^+$, 483, 439 m/z.

Step B

In a manner analogous to that described in Example 1 (step B), from the material of step A above (250 mg), with 10% Pd/C (50 mg) under a hydrogen atmosphere, (3S-tert-butoxycarbonylamino-4-hydroxy-2R-(4-methoxy)phenpropyl)succinyl-piperidinamide was obtained as a colourless oil (200 mg).

Step C

In a manner analogous to that described in Example 2 (step A), reaction of (3S-tert-butoxycarbonylamino-4-hydroxy-2R-(4-methoxy)phenpropyl)succinyl-piperidinamide (200 mg) with O-benzylhydroxylamine hydrochloride (85 mg), N-methylmorpholine (0.12 mL) and TBTU (172 mg) afforded (4-benzyloxyamino-3S-tert-butoxycarbonylamino-2R-(4-methoxy)phenpropyl)succinyl-piperidinamide (240 mg) as a white solid. FT-IR (CHCl$_3$) 3236 br (NH), 1705 (benzylhydroxamate CO), 1678 (carbamate CO), 1614 (amide CO) cm$^-$. H$^1$-NMR (400 MWz, CDCl$_3$) 1.39 (s, 9 H);1.4–1.8 (m, 10 H); 2.54 (m, 2 H); 3.3–3.6 (m, 5 H); 3.78 (s, 3 H); 4.35 (dd, 1 H, J=3.5 and 8.5 Hz); 4.85 (s, 2 H); 6.73 (d, 1 H, J=8.5 Hz); 6.81 (d, 2 H, J=8.5 Hz); 7.05 (d, 2 H, J=8.5 Hz); 7.38 (m, 5 H); 9.18 (s, 1 H) ppm. ES-MS 576 (MNa)$^+$, 554 (MH)$^+$, 498, 454, 375, 303 m/z.

Step D

In a manner analogous to that described in Example 2 (step B), from the material from step C above (240 mg), with 10% Pd/C (50 mg), under a hydrogen atmosphere, the title compound was obtained as a pinkish solid (175 mg). FT-IR (CHCl$_3$) 3255 br (OH,NH), 1710 (hydroxamic CO), 1665 (carbamate CO), 1612 (amide CO) cm$^{-1}$. H$^1$-NMR (400 MHz, DMSO-d$_6$) 1.35 (s, 9 H); 1.3–1.6 (m, 10 H); 2.42 (m, 2 H); 3.2–3.4 (m, 5 H); 3.69 (s, 3 H); 4.02 (dd, 1 H, J=6.2 and 9.1 Hz); 6.58 (d, 1 H, J=9.1 Hz); 6.80 (d, 2 H, J=8.5 Hz); 7.04 (d, 2 H, J=8.5 Hz); 8.78 (br signal, 1 H); 10.67 (br signal, 1 H) ppm. ESI-MS 486 (MNa)$^+$, 64 (MH)$^+$, 408, 375, 364, 303 m/z.

EXAMPLE 18

(3S-Amino-4-hydroxyamino-2R-(4-methoxy)phenpropyl)succinyl-piperidinamide

In a manner analogous to that described in Example 3, reaction of (3S-tert-butoxycarbonylamino-4-hydroxyamino-2R-(4-methoxy)phenpropyl)succinyl-piperidinamide (125 mg; from Example 17) with 95% aqueous trifluoroacetic acid (2 mL) and work-up afforded the title compound, trifluoroacetate salt, as a white solid (90 mg). FT-IR (KBr) 3250 br (OH,NH), 1668 (hydroxamic CO), 1603 (amide CO) cm$^{-1}$. In DMSO solution, the compound is present as a mixture of two rotamers (M, major; m, minor). H$^1$-NMR (400 MHz, DMSO-d$_6$) 1.2–1.6 (m, 10 H); 2.44 (m, 2 H); 3.17 (m, 1 H); 3.2–3.8 (m, 5 H); 3.70 (s, 3 H); 6.82 (d, 2 H, J=8.5 Hz) 7.06 (d, 2 H, J=8.5 Hz); 7.9 (br signal, 3 H); 9.32 (br signal, 1 H, M); 9.7 (br signal, 1 H, m); 10.7 (br signal, 1 H, m); 11.1 (br signal, 1 H, M) ppm. ESI/CID-MS 386 (MNa)$^+$, 364 (MH)$^+$, 303 (M—HONHCO)$^+$, 112 m/z.

EXAMPLE 19

(3S-N,N-Dimethylamino-4-hydroxyamino-2R-(4-methoxy)phenpropyl)succinyl-morpholinamide Step A In a manner analogous to that described in Example 4 (step A), reaction of the compound described in Example 13, step A (600 mg), with 95% aqueous trifluoroacetic acid (5 mL) and work-up afforded (3S-amino-4-benzyloxy-2R-(4-methoxy)phenpropyl)succinyl-morpholinamide (500 mg), trifluoroacetate salt, as a yellow oil.

Step B

In a manner analogous to that described in Example 4 (step B), reaction of the material from step A above (350 mg) with 37% aqueous HCHO (10 mL) and NaCNBH$_3$ (100 mg) afforded (4-benzyloxy-3S-N,N-dimethylamino-2R-(4-methoxy)phenpropyl)succinyl-morpholinamide as a colourless oil (250 mg).

Step C

In a manner analogous to that described in Example 4 (step C), reaction of the material from step B above (250 mg) with 10% Pd/C (50 mg) under a hydrogen atmosphere afforded (3S-N,N-dimethylaminohydroxy-2R-(4-methoxy)phenpropyl)succinyl-morpholinamide as a colourless oil (190 mg).

Step D

In a manner analogous to that described in Example 5 (step A), reaction of the material from step C above (190 mg) with O-benzylhydroxylamine hydrochloride (95 mg), N-methylmorpholine (0.15 mL) and TBTU (193 mg) afforded (4-benzyloxyamino-3S-N,N-dimethylamino-2R-(4-methoxy)phenpropyl)succinyl-morpholinamide (160 mg) as a colourless oil.

Step E

In a manner analogous to that described in Example 5 (step B), reaction of the material from step D above (160 mg) with 10% Pd/C (30 mg) under a hydrogen atmosphere afforded the title compound (130 mg) as a white solid. FT-IR (CHCl$_3$) 3229 br (OH, NH); 1659 (hydroxamic CO); 1614 (amide CO) cm$^{-1}$. H$^1$-NMR (200 MHz, DMSO-d$_6$) 1.0–1.5 (m, 4 H); 2.13 (s, 4 H); 2.40 (m, 2 H); 3.05 (d, 1 H, J=10.7 Hz); 3.2–3.7 (m, 9 H); 3.69 (s, 3 H); 6.80 (d, 2 H, J=8.8 Hz), 7.04 (d, 2 H, J=8.8 Hz); 8.85 (br signal, 1 H); 10.50 (br signal, 1 H) ppm. ESI-MS 416 (MNa)$^+$, 394 (MH)$^+$, 333 (M—HONHCO)$^+$ m/z.

EXAMPLE 20

(4-Hydroxyamino-3S-(4-methoxyphenylsulfonyl) amino-2R-(4-methoxy)phenpropyl)succinyl-morpholinamide ps Step A In a manner analogous to that described in Example 6 (step A), reaction of the material from Example 19, step A (270 mg), with (4-methoxybenzenesulfonyl)chloride (185 mg) and triethylamine (0.17 mL) afforded (4-benzyloxy-3S-(4-methoxyphenylsulfonyl)amino-2R-(4-methoxy) phenpropyl)succinyl-morpholinamide as a white solid (100 mg). H$^1$-NMR (200 MHz, CDCl$_3$) 1.5–1.9 (m, 4 H); 2.54 (m, 2 H); 3.12 (m, 1 H); 3.0–3.5 (m, 8 H); 3.78 and 3.82 (two s, 6 H); 4.25 (dd, 1 H, J=3.9 and 9.8 Hz); 4.89 (s, 2 H); 6.52 (d, 1 H, J=9.8 Hz); 6.80 (m, 4 H); 7.06 (d, 2 H, J=8.8 Hz); 7.1–7.3 (m, 5 H); 7.76 (d, 2 H, J=8.8 Hz) ppm. ESI/CID-MS 633 (MNa)$^+$, 611 (MH)$^+$, 546, 171, 88 m/z.

Step B

In a manner analogous to that described in Example 6 (step B), reaction of the material from step A above (100 mg) with 10% Pd/C (20 mg) under a hydrogen atmosphere afforded 90 mg of (4-hydroxy-3S-(4-methoxyphenylsulfonyl)amino-2R-(4-methoxy)phenpropyl)succinyl-morpholinamide was obtained as a colourless oil.

Step C

In a manner analogous to that described in Example 7 (step A), reaction of the material from step B above (90 mg) with O-benzylhydroxylamine (33 mg), N-methylmorpholine (0.05 mL) and TBTU (65 mg) afforded (4-benzyloxyamino-3S-(4-methoxyphenylsulfonyl)amino-2R-(4-methoxy) phenpropyl)succinyl-morpholinamide (88 mg ) as a white solid. H$^1$-NMR (200 MHz, CDCl$_3$) 1.0–1.5 (m, 4 H); 2.32 (m, 2 H); 3.2–4.0 (m, 10 H); 3.78 and 3.84 (two s, 6 H); 4.79 and 4.83 (two d, 2 H, J=11.0 Hz); 6.81 (d, 2 H, J=8.7 Hz); 6.92 (m, 4 H); 7.39 (m, 5 H); 7.75 (d, 2 H, J=8.8 Hz); 9.64 (s, 1 H) ppm. ESI-MS 648 (MNa)$^+$, 626 (MH)$^+$, 503, 475, 361 m/z.

Step D

In a manner analogous to that described in Example 7 (step B), reaction of the material from step C above (88 mg) with 10% Pd/C (20 mg) under a hydrogen atmosphere afforded the title compound as a white solid (70 mg). FT-IR (CHCl$_3$) 3266 br (OH,NH), 1678 br (hydroxamic CO), 1612 (amide CO) cm$^{-1}$. H$^1$-NMR (400 MHz, DMSO-d$_6$) 1.0–1.5 (m, 4 H), 2.33 (m, 2 H); 2.97 (ddd, 1 H, J=3.8, 9.8 and 10.7 Hz); 3.1–3.6 (m, 8 H); 3.68 and 3.78 (two s, 6 H); 3.78 (d, 1 H, J=10.7 Hz); 6.79 (d, 2 H, J=8.5 Hz); 7.00 (m, 4 H); 7.60 (d, 2 H, J=9.0 Hz); 7.80 (br signal, 1 H); 8.84 (s, 1 H); 10.76 (br signal, 1 H) ppm. FAB-MS 536 (MH)$^+$, 475 (M—HONHCO)$^+$, 364, 305, 171, 121, 114, 88 m/z.

EXAMPLE 21

(3S-tert-Butoxycarbonylamino-2R-cyclopentylmethyl-4-hydroxyamino)succinyl-piperidinamide Step A In a manner analogous to that described in Example 1 (step A), reaction of 4S-benzyloxycarbonyl-1-tert-butoxycarbonyl-3R-cyclopentylmethylazetidin-2-one (1.25 g, obtained as described in Preparation D) with piperidine (0.65 mL) afforded (4-benzyloxy-3S-tert-butoxycarbonylamino-2R-cyclopentylmethyl)succinyl-piperidinamide (1.3 g) as a yellow oil. H$^1$-NMR (400 MHz, DMSO-d$_6$) 0.9–1.7 (m, 17 H); 1.32 (s, 9 H); 3.2–3.4 (m, 5 H); 4.30 (dd, 1 H, J=5.3 and 9.4 Hz); 5.07 and 5.13 (two d, 2 H, J=12.6 Hz); 6.68 (d, 1 H, J=9.4 Hz); 7.36 (m, 5 H) ppm. ESI-MS 495 (MNa)$^+$, 473 (MH)$^+$, 417, 373 m/z.

Step B

In a manner analogous to that described in Example 1 (step B), reaction of the material from step A above (500 mg) with 10% Pd/C (100 mg) under a hydrogen atmosphere afforded (3S-tert-butoxycarbonylamino-2R-cyclopentylmethyl-4-hydroxy)succinyl-piperidinamide as a colourless oil (410 mg).

Step C

In a manner analogous to that described in Example 2 (step A), reaction of (3S-tert-butoxycarbonylamino-2R-cyclopentylmethyl-4-hydroxy)succinyl-piperidinamide (410 mg) with O-benzylhydroxylamine hydrochloride (205 mg), N-methylmorpholine (0.29 mL) and TBTU (410 mg) afforded (4-benzyloxyamino-3S-tert-butoxycarbonylamino-2R-cyclopentyl-methyl)succinyl-piperidinamide as a white solid (500 mg). H$^1$-NMR (400 MHz, CDCl$_3$) 1.0 and 1.8 (m, 17 H); 1.37 (s, 9 H); 3.4–3.6 (m, 5 H); 4.32 (dd, 1 H, J=3.4 and 8.5 Hz); 4.83 (s, 2 H); 6.73 (d, 1 H, J=8.5 Hz); 7.37 (m, 5 H); 9.16 (s, 1 H) ppm. ESI-MS 510 (MNa)$^+$, 488, 388, 309, 237 m/z.

Step D

In a manner analogous to that described in Example 2 (step B), reaction of the material from step C above (500 mg) with 10% Pd/C (100 mg) under a hydrogen atmosphere afforded the title compound was obtained as a pink solid (400 mg). $H^1$-NMR (200 MHz, $CDCl_3$) 1.0 and 1.9 (m, 17 H); 1.45 (s, 9 H); 3.3–3.7 (m, 5 H); 4.45 (dd, 1 H, J=3.2 and 8.3 Hz); 6.77 (d, 1 H, J=8.3 Hz); 6.80 (br signal, 1 H); 9.32 (br signal, 1 H) ppm. ESI-MS 420 $(MNa)^+$, 398 $(MH)^+$, 342, 309, 298, 237 m/z.

EXAMPLE 22

(3S-Amino-2R-cyclopentylmethyl-4-hydroxyamino) succinyl-piperidinamide

Step A

A solution of 4S-benzyloxycarbonyl-1-tert-butoxycarbonyl-3R-cyclopentylmethylazetidin-2-one (4.6 g; obtained as described in Preparation D) in acetonitrile (100 mL) was treated with piperidine (2 mL) and stirred at r.t. for 6 h. The mixture was concentrated under vacuum and the residue was poured into EtOAc/water. The organic layer was washed sequentially with 4% aqueous hydrochloric acid, brine, 4% aqueous hydrogen bicarbonate and brine, then dried over sodium sulfate and rotoevaporated. (4-Benzyloxy-3S-tert-butoxycarbonylamino-2R-cyclopentylmethyl)succinyl-piperidinamide (5.6 g) was obtained as a yellow oil. $H^1$-NMR (400 MHz, DMSO-$d_6$) 0.9–1.7 (m, 17 H); 1.32 (s, 9 H); 3.2–3.4 (m, 5 H); 4.30 (dd, 1 H, J=5.3 and 9.4 Hz); 5.07 and 5.13 (two d, 2 H, J=12.6 Hz); 6.68 (d, 1 H, J=9.4 Hz); 7.36 (m, 5 H) ppm. ESI-MS 495 $(MNa)^+$, 473 $(MH)^+$, 417, 373 m/z.

Step B

A mixture of the compound from Step A above (5.6 g) and 5% Pd/C (1.2 g ) in EtOH (200 mL) was exposed to a hydrogen atmosphere for 2 hours under stirring. After purging the mixture with nitrogen, the catalyst was removed by filtration over Celite, and the filtrate was concentrated to dryness under reduced pressure, giving (3S-tert-butoxycarbonylamino-2R-cyclopentylmethyl-4-hydroxy)succinyl-piperidinamide (4.5 g) as a colourless oil.

Step C

The compound from Step B above (4.5 g) in acetonitrile (150 mL) was treated sequentially with O-benzylhydroxylamine hydrochloride (2.07 g), N-methylmorpholine (2.86 mL) and TBTU (4.17 g). The reaction mixture was stirred at room temperature for 3 hr, then concentrated under vacuum to about one third of its initial volume and partitioned between EtOAc and water. The upper layer was separated and washed sequentially with 2% aqueous hydrochloric acid, water, 4% aqueous hydrogen bicarbonate and brine. After drying (sodium sulfate), removal of the solvent afforded (4-benzyloxyamino-3S-tert-butoxycarbonylamino-2R-cyclopentylmethyl)succinyl-piperidinamide as a colourless oil (5.65 g). $H^1$-NMR (400 MHz, $CDCl_3$) 1.0 and 1.8 (m, 17 H); 1.37 (s, 9 H); 3.4–3.6 (m, 5 H); 4.32 (dd, 1 Hz, J=3.4 and 8.5 Hz); 4.83 (s, 2 H); 6.73 (d, 1 H, J=8.5 Hz), 7.37 (m, 5 H); 9.16 (s, 1 H) ppm. ESI-MS 510 $(MNa)^+$, 488, 388, 309, 237 m/z.

Step D

A mixture of the compound from Step C above (5.65 g) and 5% Pd/C (0.56 g) in ethanol (300 mL) was exposed to a hydrogen atmosphere for 1 h under stirring. The reaction mixture was purged with nitrogen, then filtered over Celite and eventually rotoevaporated to give (3S-tert-butoxycarbonylamino-2R-cyclopentylmethyl-4-hydroxyamino)succinyl-piperidinamide as a whitish solid (4.6 g). $H^1$-NMR (200 MHz, $CDCl_3$) 1.0 and 1.9 (m, 17 H); 1.45 (s, 9 H); 3.3–3.7 (m, 5 H); 4.45 (dd, 1 H, J=3.2 and 8.3 Hz); 6.77 (d, 1 H, J=8.3 Hz); 6.80 (br signal, 1 H); 9.32 (br signal, 1 H) ppm. ESI-MS 420 $(MNa)^+$, 398 $(MH)^+$, 342, 309, 298, 237 m/z.

Step E

The compound from Step D above (4.6 g) was treated with 95% aqueous trifluoroacetic acid (40 mL) and let stand at r.t. for 45 minutes, after which time toluene (50 mL) was added, and the resulting mixture was concentrated to dryness under reduced pressure. The residue was purified by reverse-phase chromatography (LiChroprep RP C-18) eluting with acetonitrile-water mixtures (from 0:100 to 50:50) containing 1% TFA. Product containing fractions were collected and concentrated in vacuo. (3S-Amino-2R-cyclopentylmethyl-4-hydroxyamino)-succinyl-piperidinamide was thus obtained as a white powder (trifluoroacetate salt, 3.7 g; ca. 75% overall yield). In DMSO solution, the compound is present as a mixture of two rotamers (M, major; m, minor). $H^1$-NMR (400 MHz, DMSO-$d_6$) 0.9–1.8 (m, 17 H); 3.16 (m, 1 H); 3.40 (m, 4 H); 3.67 (m, 1 H); 7.95 (br signal, 3 H, m); 8.14 (br signal, 3 H, M); 9.33 (s, 1 H, M); 9.77 (s, 1 H, m); 10.69 (s, 1 H, m); 11.12 (s, 1 H, M) ppm. FAB-MS 298 $(MH)^+$, 237 $(M—HONHCO)^{30}$, 208, 112, 86, 84 m/z.

EXAMPLE 23

(2R-Cyclopentylmethyl-4-hydroxyamino-3S-(4-methoxyphenylsulfonyl)amino)succinyl-piperidinamide Step A In a manner analogous to that described in Example 6 (step A), reaction of (3S-amino-4-benzyloxy-2R-cyclopentylmethyl)succinyl-piperidinamide trifluoroacetate salt (630 mg) with. (4-methoxyphenylsulfonyl)chloride (400 mg) and triethylamine (0.78 mL) afforded (4-benzyloxy-2R-cyclopentylmethyl-3S-(4-methoxyphenylsulfonyl)amino) succinyl-piperidinamide as a white solid (200 mg).

Step B

In a manner analogous to that described in Example 6 (step B), reaction of the material from step A above (200 mg) with 10% Pd/C (60 mg) under a hydrogen atmosphere afforded (2R-cyclopentylmethyl-4-hydroxy-3S-(4-methoxyphenylsulfonyl)amino)succinyl-piperidinamide as a white solid (250 mg).

Step C

In a manner analogous to that described in Example 7 (step A), reaction of the material from step B above (250 mg) with O-benzylhydroxylamine hydrochloride (110 mg), N-methylmorpholine (0.15 mL) and TBTU (215 mg) afforded (4-benzyloxyamino-2R-cyclopentylmethyl-3S-(4-methoxyphenylsulfonyl)amino)succinyl-piperidinamide (265 mg) as a white solid. $H^1$-NMR (400 MHz, $CDCl_3$) 0.7–1.7 (m, 17 H); 3.4–3.6 (m, 5 H); 3.8 (dd, 1 H, J=2.9 and 6.4 Hz); 3.85 (s, 3 H); 4.80 and 4.84 (two d, 2 H, J=11.1 Hz); 6.95 (d, 2 H, J=9.1 Hz); 7.19 (d, 1 H, J=6.4 Hz); 7.39 (m, 5 H); 7.76 (d, 2 H, J=9.1 Hz); 9.69 (s, 1 H) ppm. ESI/CID-MS 580 $(MNa)^+$, 558 $(MH)^+$, 435, 407, 388, 237, 149, 112 m/z.

Step D

In a manner analogous to that described in Example 7 (step B), reaction of the material from step C above (260 mg) with 10% Pd/C (50 mg) under a hydrogen atmosphere afforded the title compound (125 mg) as a white solid. $H^1$-NMR (200 MHz, $CDCl_3$) 0.8–1.8 (m, 17 H); 3.2–3.8 (m, 5 H); 3.86 (s, 3 H), 3.90 (m, 1 H); 6.98 (d, 2 H, J=9.0 Hz); 7.02 (br signal, 1 H); 7.29 (s, 1 H); 7.83 (d, 2 H, J=9.0 Hz); 9.81 (br signal, 1 H) ppm. FAB-MS 468 $(MH)^+$, 435, 407, 298, 237, 208, 171, 112, 86, 84 m/z.

EXAMPLE 24

(3S-Amino-4-hydroxyamino-2R-isobutyl)succinyl-dicyclohexylmethylamide

Step A

Sodium azide (66 mg) and dicyclohexylamine (300 mg; see Preparation G) were added at room temperature to a solution of 4S-benzyloxycarbonyl-1-tert-butoxycarbonyl-3R-isobutylazetidin-2-one (360 mg; see Preparation A) in DMF (8 mL). The mixture was stirred overnight, then diluited with EtOAc and washed with $H_2O$, saturated aqueous $NaHCO_3$ and 2% Hcl. The organic layer was dried over $Na_2SO_4$, filtered and evaporated. The crude product was purified by flash cromatography on silica gel (n-hexane/EtOAc) to afford (4-benzyloxy-3S-tert-butoxycarbonylamino-2R-isobutyl)succinyl-dicyclohexylmethylamide (230 mg) as a white solid. ESI-MS 567 (MNa)$^+$, 545(MH)$^+$, 489, 445, 167 m/z.

Step B

In a manner analogous to that described in Example 1 (step B), reaction of the material from step A above (220 mg) with 10% Pd/C (50 mg) under a hydrogen atmosphere afforded (3S-tert-butoxycarbonylamino-4-hydroxy-2R-isobutyl)succinyl-dicyclohexylmethylamide as an oil (180 mg).

Step C

In a manner analogous to that described in Example 2 (step A), reaction of the material from step B above (180 mg) with O-benzylhydroxylamine hydrochloride (77 mg), N-methylmorpholine (0.1 mL) and TBTU (128 mg) afforded (4-benzyloxyamino-3S-tert-butoxycarbonylamino-2R-isobutyl)succinyl-dicyclohexylmethylamide (200 mg) as a white solid. $H^1$-NMR (400 MHz, $CDCl_3$) 0.80–1.8 (m, 25 H); 0.92 (d, 6 H, J=6.4 Hz); 1.39 (s, 9 H); 3.02 (m, 1 H); 3.56 (m, 1 H); 4.25 (d, 1 H, J=7.9 Hz); 4.85 (s, 2 H); 5.58 (d, 1 H, J=9.4 Hz); 6.41 (d, 1 H, J=7.9 Hz); 7.34 (m, 5 H); 9.31 (s, 1 H) ppm. ESI-MS 610 (MK)$^+$, 594 (MNa)$^+$, 572 (MH)$^+$, 516, 488, 472, 112 m/z.

Step D

In a manner analogous to that described in Example 2 (step B), reaction of the material from step C above (180 mg) with 10% Pd/C (50 mg) under a hydrogen atmosphere afforded (3S-tert-butoxycarbonylamino-4-hydroxyamino-2R-isobutyl)succinyl-dicyclohexylmethylamide (100 mg) as a white solid.

Step E

In a manner analogous to that described in Example 3, reaction of the material from step D above (100 mg) with 95% aqueous trifluoroacetic acid (5 mL) afforded the title compound, trifluoroacetate salt, as a white solid (85 mg). In DMSO solution, the compound is present as a mixture of two rotamers (M, major; m, minor). $H^1$-NMR (400 MHz, DMSO-d6) 0.86 and 0.88 (two d, 6 H, J=6.8 Hz); 0.9–1.7 (m, 25 H); 2.74 (m, 1 H, M); 3.10 (m, 1 H, m); 3.60 (m, 2 H); 7.76 (d, 1 H, J=9.8 Hz); 8.01 (br signal, 3 H, M); 8.10 (br signal, 3 H, m); 9.25 (br signal, 1 H, M); 9.57 (s, 1 H, m); 10.67 (s, 1 H, m); 11.00 (s, 1 H, M) ppm. FAB-MS 382 (MH)$^+$, 321 (M—HONHCO)$^+$, 194, 187, 112, 100, 89, 83 m/z.

EXAMPLE 25

(3S-Amino-4-hydroxyamino-2R-isobutyl)succinyl-diphenylmethylamide

Step A

In a manner analogous to that described in Example 28 (step A), reaction of 4S-benzyloxycarbonyl-1-tert-butoxycarbonyl-3R-isobutylazetidin-2-one (360 mg; see Preparation A) with diphenylmethylamine (0.34 ml) and $NaN_3$ (33 mg) afforded (4-benzyloxy-3S-tert-butoxycarbonylamino-2R-isobutyl)succinyl-diphenylmethylamide (150 mg) as a white solid.

$H^1$-NMR (400 MHz, $CDCl_3$) 0.89 and 0.91 (two d, 6 H, J=6.7 Hz); 1.2–1.7 (m, 3 H); 1.39 (s, 9 H); 2.97 (m, 1 H); 4.46 (dd, 1 H, J=3.8 and 9.7 Hz); 4.95 and 5.02 (two d, 2 H, J=12.6 Hz); 6.07 (d, 1 H, J=9.7 Hz); 6.09 and 6.14 (two d, 2 H, J=7.6 Hz); 7.1–7.4 (m, 15 H) ppm.

Step B

In a manner analogous to that described in Example 1 (step B), reaction of the material from step A above (150 mg) with 10% Pd/C (30 mg) under a hydrogen atmosphere afforded (3S-tert-butoxycarbonylamino-4-hydroxy-2R-isobutyl)succinyl-diphenylmethylamide as a white solid (100 mg).

Step C

In a manner analogous to that described in Example 2 (step A), reaction of the material from step B above (100 mg) with O-benzylhydroxylamine hydrochloride (42 mg), N-methylmorpholine (0.06 mL) and TBTU (85 mg) afforded (4-benzyloxyamino-3S-tert-butoxycarbonylamino-2R-isobutyl)succinyl-diphenylmethylamide (100 mg) as a white solid.

Step D

In a manner analogous to that described in Example 2 (step B), reaction of the material from step C above (100 mg) with 10% Pd/C (20 mg) under a hydrogen atmosphere afforded (3S-tert-butoxycarbonylamino-4-hydroxyamino-2R-isobutyl)succinyl-diphenylmethyl amide as a white solid (90 mg).

Step E

In a manner analogous to that described in Example 3, reaction of the material from step D above (90 mg) with 95% aqueous trifluoroacetic acid (5 mL) afforded the title compound as a white solid (85 mg; trifluoroacetate salt). In DMSO solution, the compound is present as mixture of two rotamers (M, major; m, minor). $H^1$-NMR (400 MHz, DMSO-d$_6$) 0.74 and 0.84 (two d, 6 H, J=6.8 Hz); 1.12 and 1.49 (two m, 2 H); 1.31 (m, 1 H), 2.85 (m, 1 H); 3.58 (m, 1 H); 6.09 (d, 1 H, J=7.7 Hz), 7.28 (m, 10 H); 8.20 (br signal, 3 H); 9.13 (d, 1 H, J=8.1 Hz, M); 9.25 (d, 1 H, J=8.1 Hz, m); 9.38 (br signal, 1 H, M); 9.60 (s, 1 H,m); 10.80 (s, 1 H, m); 11.10 (s, 1 H, M) ppm. FAB-MS 370 (MH)$^+$, 309 (M—HONHCO)$^+$, 204, 182, 167, 100 m/z.

EXAMPLE 26

(3S-tert-Butoxycarbonylamino-2R-cyclopentylmethyl-4-hydroxyamino)succinyl-(4-piperonyl)piperazinamide Step A In a manner analogous to that described in Example 1 (step A), reaction of 4S-benzyloxycarbonyl-1-tert-butoxycarbonyl-3R-cyclopentylmethylazetidin-2-one (500 mg; see Preparation D) with 1-piperonylpiperazine (545 mg) in acetonitrile afforded (4-benzyloxycarbonyl-3S-tert-butoxycarbonylamino-2R-cyclopentylmethyl)succinyl-(4-piperonyl)piperazinamide (800 mg) as an oil. $H^1$-NMR (200 MHz, $CDCl_3$) 1.0–1.9 (m, 11 H), 1.41 (s, 9 H); 2.30 (m, 4 H); 3.36 (s, 2 H); 3.36 (m, 1 H); 3.50 (m, 4 H); 4.51 (dd, 1 H, J=4.1 and 9.8 Hz); 5.06 and 5.18 (two d, 2 H, J=12.4 Hz); 5.94 (s, 2 H); 6.40 (d, 1 H, J=9.8 Hz); 6.6–6.9 (m, 3 H); 7.33 (m, 5 H) ppm. ESI/CID-MS 630 (MNa)$^+$, 608 (MH)$^+$, 508, 372, 221, 135 m/z.

Step B

In a manner analogous to that described in Example 1 (step B), reaction of the material from step A above (800 mg)

with 10% Pd/C (100 mg) under a hydrogen atmosphere afforded (3S-tert-butoxycarbonylamino-2R-cyclopentylmethyl-4-hydroxy)succinyl-(4-piperonyl)piperazinamide (600 mg) as a white solid.

Step C

In a manner analogous to that described in Example 2 (step A), reaction of the material from step B above (600 mg) with O-benzylhydroxylamine hydrochloride (160 mg), N-methylmorpholine (0.27 mL) and TBTU (385 mg) afforded (4-benzyloxyaminocarbonyl-3S-tert-butoxycarbonylamino-2R-cyclopentylmethyl)succinyl-(4-piperonyl)piperazinamide (280 mg) as a white solid. $H^1$-NMR (400 MHz, DMSO-$d_6$) 0.9–1.7 (m, 11 H); 1.37 (s, 9 H), 2.1–2.4 (m, 4 H); 3.18 (m, 1 H); 3.30–3.60 (m, 6 H); 4.01 (dd, 1 H, J=6.4 and 9.0 Hz); 4.74 (s, 2 H); 5.97 (s, 2 H); 6.66 (d, 1 H, J=9.0 Hz); 6.7–6.8 (m, 3 H) 7.34 (m, 5 H); 11.38 (s, 1 H) ppm. ESI-MS 645 (MNa)$^+$, 623 (MH)$^+$, 567, 523, 372, 283, 221 m/z.

Step D

In a manner analogous to that described in Example 2 (step B), reaction of the material from step C above (280 mg) with 10% Pd/C (50 mg) under a hydrogen atmosphere afforded the title compound (160 mg) as a white solid. $H^1$-NMR (400 MHz, DMSO-$d_6$) 0.9–1.7 (m; 11 H), 1.35 (s, 9 H); 2.1–2.4 (m, 4 H), 4.00 (dd, 1 H, J=6.8 and 9.0 Hz); 5.97 (s, 2 H); 6.57 (d, 1 H, J=9.0 Hz); 6.6–6.8 (m, 3 H); 8.80 (br signal, 1 H); 10.2 (br signal, 1 H) ppm. ESI-MS 555 (MNa)$^+$, 533 (MH)$^+$, 477, 444, 221 m/z.

EXAMPLE 27

(3S-Amino-2R-cyclopentylmethyl-4-hydroxyamino)succinyl-(4-piperonyl)piperazinamide In a manner analogous to that described in Example 3, reaction of the compound described in Example 26 (140 mg) with 95% aqueous trifluoroacetic acid (3 mL) afforded the title compound (bis-trifluoroacetate salt) as a white solid (100 mg). In DMSO solution, the compound is present as a mixture of two rotamers (M, major; m, minor). $H^1$-NMR (400 MHz, DMSO-$d_6$) 1.0–1.8 (m, 11 H); 2.8–4.6 (br m, 10 H); 3.20 (m, 1 H); 3.70 (m, 1 H); 6.07 (s, 2 H); 7.00 (m, 3 H); 8.08 (br signal, 3 H, m); 8.22 (br signal, 3 H, M); 9.43 (br signal, 1 H, M); 10.1 (br signal, 1 H, M); 10.8 (s, 1 H, m); 11.20 (s, 1 H, M) ppm. ESI-MS 459 (MNa)$^+$, 433 (MH)$^+$, 299, 238, 221, 135 m/z.

By minor variations of the procedures of the examples above, and starting from the appropriate intermediates, the following compounds were obtained:

EXAMPLE 28

(3S-Amino-4-hydroxyamino-2R-(4-methoxy)phenpropyl)succinyl-azetidinamide

Trifluoroacetate salt. $H^1$-NMR (400 MHz, DMSO-$d_6$): 1.44 (m, 4 H, C<u>H</u>$_2$C<u>H</u>$_2$—CH$_2$Ph), 2.14 (m, 2 H, azetidine 3-methylene), 2.47 (m, 2 H, CH$_2$CH$_2$—C<u>H</u>$_2$—Ph), 2.58 (m, 1 H, C<u>H</u>-phenpropyl), 3.57 (d, J=6.1 Hz, 1 H, C<u>H</u>—NH$_3^+$), 3.69 (s, 3 H, OMe), 3.86, 4.10 and 4.30 (each m; 4 H, azetidine 2-,4-methylene), 6.82 (d, J=8.2 Hz, 2 H, aromatic protons ortho to methoxy), 7.07 (d, J=8.2 Hz, 2 H, aromatic protons meta to methoxy), 8.00 (br s, 3 H, NH$_3^+$), 9.32 (s, 1 H, NH—O<u>H</u>), and 11.10 ppm (br s, 1 H, N<u>H</u>—OH).

EXAMPLE 29

(3S-Amino-4-hydroxyamino-2R-(4-methoxy)phenpropyl)succinyl-N-cyclohexylamide

Trifluoroacetate salt. $H^1$-NMR (400 MHz, DMSO-d6, 55° C.): 1.0–1.9 (m, 13 H, C<u>H</u>$_2$C<u>H</u>$_2$—CH$_2$Ph+cyclohexyl methylene protons), 2.50 (m, 3 H, C<u>H</u>—CH$_2$CH$_2$—C<u>H</u>$_2$—Ph), 3.45 (d, J=7.3 Hz, 1 H, C<u>H</u>—NH$_3^+$), 3.55 (m, 1 H, cyclohexyl methyne proton), 3.70 (s, 3 H, OMe), 6.81 (d, J=8.6 Hz, 2 H, aromatic protons ortho to methoxy), 7.04 (d, J=8.6 Hz, 2 H, aromatic protons meta to methoxy), 7.81 (d, J=7.7 Hz, 1 H, CON<u>H</u>-cyclohexyl), 8.00 (br s, 3 H, NH$_3^+$), 9.10 (br s, 1 H, NH—O<u>H</u>), and 10.0 ppm (br s, 1 H, N<u>H</u>—OH). At 55° C., the —NH$_3^+$ protons were not detectable (7–8 ppm at lower temperatures).

EXAMPLE 30

(2R-Cyclopentylmethyl-3S-N,N-dimethylamino-4-hydroxyamino)succinyl-piperidinamide $H^1$-NMR (400 MHz, DMSO-$d_6$): 0.9–1.9 (m, 17 H, cyclopentylmethyl+piperidine 3-,4-,5-methylene protons), 2.12 (s, 6 H, NMe$_2$), 3.00 (d, J=10.7 Hz, 1 H, C<u>H</u>—NMe$_2$), 3.27 (m, 1 H, C<u>H</u>-cyclopentylmethyl), 3.3–3.6 (m, 4 H, piperidine 2-,6-methylene), 8.83 (s, 1 H, NH—O<u>H</u>), and 10.51 ppm (br s, 1 H, N<u>H</u>—OH).

EXAMPLE 31

(4-Hydroxyamino-2R-(4-methoxy)phenpropyl-3S-phenylmethylsulfonylamino)succinyl-piperidinamide $H^1$-NMR (400 MHz, DMSO-$d_6$): 1.2–1.6. (m, 10 H, CH—C<u>H</u>$_2$C<u>H</u>$_2$—CH$_2$Ph+piperidine 3-,4-,5-methylene protons), 2.41 (m, 2 H, C<u>H</u>$_2$—Ph), 3.16 (m, 1 H, C<u>H</u>-phenpropyl), 3.44 (m, 4 H, piperidine 2-,6-methylene), 3.69 (s, 3 H, methoxy), 3.93 (m, 1 H, C<u>H</u>—NHSO$_2$), 4.08 and 4.19 (each d, J=13.7 Hz, NHSO$_2$—C<u>H</u>$_2$—Ph), 6.80 (d, J=8.6 Hz, 2 H, aromatic protons ortho to methoxy), 7.05 (d, J=8.6 Hz, 2 H, aromatic protons meta to methoxy), 7.33 (m, 5 H, Ph), 7.59 (br s, 1 H, N<u>H</u>—SO$_2$), 9.02 (br s, 1 H, NH—O<u>H</u>), and 10.90 ppm (br s, 1 H, N<u>H</u>—OH).

EXAMPLE 32

(3S-Amino-4-hydroxyamino-2R-(4-methoxy)phenpropyl)succinyl-(1R-cyclohexylethyl)amide Trifluoroacetate salt. $H^1$-NMR (400 MHz, DMSO-$d_6$): 0.93 (d, J=6.8 Hz, 3 H, C<u>H</u>$_3$—CH), 0.8–1.8 (m, 15 H, CH—C<u>H</u>$_2$C<u>H</u>$_2$—CH$_2$Ph+cyclohexyl protons), 2.43 (m, 2 H, C<u>H</u>$_2$—Ph), 2.62 (m, 1 H, C<u>H</u>-phenpropyl), 3.57 (m, 2 H, C<u>H</u>—CH$_3$+C<u>H</u>—NH$_3^+$), 3.69 (s, 3 H, methoxy), 6.81 (d, J=8.6 Hz, 2 H, aromatic protons ortho to methoxy), 7.05 (d, J=8.6 Hz, 2 H, aromatic protons meta to methoxy), 7.93 (d, J=8.6 Hz, 1 H, CO—N<u>H</u>—CH), 8.12 (br s, 3 H, NH$_3^+$), 9.33 (s, 1 H, NH—O<u>H</u>), and 11.05 ppm (s, 1 H, N<u>H</u>—OH).

EXAMPLE 33

(3S-Amino-4-hydroxyamino-2R-(4-methoxy)phenpropyl)succinyl-(1S-cyclohexylethyl)amide Trifluoroacetate salt. $H^1$-NMR (400 MHz, DMSO-$d_6$): 0.8–1.8 (m, 15 H, CH—C<u>H</u>$_2$C<u>H</u>$_2$—CH$_2$Ph+cyclohexyl protons), 0.97 (d, J=6.8 Hz, 3 H, C<u>H</u>$_3$—CH), 2.44 (m, 2 H, C<u>H</u>$_2$—Ph), 2.61 (m, 1 H, C<u>H</u>-phenpropyl), 3.62 (m, 2 H, C<u>H</u>—CH$_3$+C<u>H</u>—NH$_3^+$), 3.68 (s, 3 H, methoxy), 6.80 (d, J=8.5 Hz, 2 H, aromatic protons ortho to methoxy), 7.03 (d, J=8.5 Hz, 2 H, aromatic protons meta to methoxy), 7.92 (d, J=8.5 Hz, 1 H, CO—N<u>H</u>—CH), 8.10 (br s, 3 H, N<u>H</u>$_3^+$), 9.34 (s, 1 H, NH—O<u>H</u>), and 11.08 ppm (s, 1 H, N<u>H</u>—OH).

EXAMPLE 34

(3S-Amino-4-hydroxyamino-2R-(4-methoxy)phenpropyl)succinyl-(4-tert-butylaminocarbonyl)piperidinamide Trifluoroacetate salt. In DMSO, the compound is present as two conformers, ca. 1:1. whose $H^1$-NMR signals coalesce upon heating. H$^1$-NMR (400 MHz, DMSO-d$_6$): 1.21 and 1.22 (each s; 9 H, t-Bu of 2 conformers), 1.2–1.8 (m, 8 H, CH—C<u>H</u>$_2$C<u>H</u>$_2$—CH$_2$Ph+piperidine 3-,5-methylene), 2.30 (m, 1 H, piperidine 4-proton), 2.45 (m, 2 H, C<u>H</u>$_2$—Ph), 2.55 and 2.92 (each m, piperidine 2- and 6-axial protons), 3.20 (m, 1 H, C<u>H</u>-phenpropyl), 3.69 (s, 3 H, methoxy), 3.69 and 3.70 (each d, J=7.0 Hz; 1 H, C<u>H</u>—NH$_3$$^+$ of 2 conformers), 3.87 and 4.35 (each m; 2 H, piperidine 2- and 6-equatorial protons), 6.81 (d, J=8.4 Hz, 2 H, aromatic protons ortho to methoxy), 7.05 and 7.07 (each d, J=8.4 Hz, 2 H, aromatic protons meta to methoxy of 2 conformers), 7.35 (s, 1 H, CO—N<u>H</u>-tBu), 8.00 (br s, 3 H, N<u>H</u>$_3$$^+$), 9.34 and 9.37 (each s; 1 H, NH—O<u>H</u> of 2 conformers), and 11.10 ppm (br s, 1 H, N<u>H</u>—OH).

EXAMPLE 35

(2R-Cyclopentylmethyl-3S-N,N-dimethylamino-4-hydroxyamino)succinyl-(4-piperonyl)-piperazinamide H$^1$-NMR (400 MHz, CDCl$_3$): 1.0–1.8 (m, 11 H, cyclopentylmethyl), 2.28 (s, 6 H, NMe$_2$), 2.38 and 2.46 (each m; 4 H, piperazinamide 3-,5-methylene), 3.35 (m, 2 H, C<u>H</u>-dimethylamino+C<u>H</u>-cyclopentylmethyl), 3.42 (s, 2 H, N—C<u>H</u>$_2$—Ar), 3.6–3.8 (m, 4 H, piperazinamide 2-,6-methylene), 5.95 (s, 2 H, O—C<u>H</u>$_2$—O), 6.75 and 6.85 (each m; 3 H, Ar), 8.00 (br s, 1 H, NH—O<u>H</u>), and 10.00 ppm (br s, 1 H, N<u>H</u>—OH).

EXAMPLE 36

(3S-(N-Cyclohexylmethyl-N-methyl)amino-4-hydroxyamino-2R-(4-methoxy)phenpropyl)-succinyl-piperidinamide H$^1$-NMR (400 Mlz, DMSO-d$_6$): 0.6–1.8 (m, 21 H, CH—CH2C<u>H</u>$_2$—CH$_2$Ph+piperidine 3-,4-, -5-methylene+ cyclohexyl protons), 2.10 (m, 2 H, C<u>H</u>$_2$—Ph), 2.12 (s, 3 H, NMe), 2.40 (m, 2 H, N—C<u>H</u>$_2$-cyclohexyl), 3.06 (d, J=10.7 Hz, 1 H, CO—C<u>H</u>—N), 3.2–3.5 (m, 5 H, C<u>H</u>-phenpropyl+piperidine 2-,6-methylene), 3.69 (s, 3 H, methoxy), 6.80 (d, J=8.5 Hz, 2 H, aromatic protons ortho to methoxy), 7.02 (d, J=8.5 Hz, 2 H, aromatic protons meta to methoxy), and 9.00 ppm (br s, 1 H, NH—O<u>H</u>); N<u>H</u>—OH not detected.

EXAMPLE 37

(2R-Cyclopentylmethyl-4-hydroxyamino-3S-(4-methoxyphenyl)sulfonylamino)succinyl-(4-piperonyl)piperazinamide Trifluoroacetate salt. In DMSO, the compound is present as a mixture of two conformers (coalescence of NMR signals upon heating). H$^1$-NMR (400 MHz, DMSO-d$_6$): 0.8–1.6 (m, 11 H, cyclopentylmethyl), 2.5–3.5 (m, 7 H, C<u>H</u>-cyclopentylmethyl+piperazinamide 3-,5-methylene+ C<u>H</u>$_2$—Ar), 3.5–4.5 (m, 5 H, C<u>H</u>—NHSO$_2$+piperazinamide 2-,6-methylene), 6.07 (s, 2 H, O—C<u>H</u>$_2$—O), 6.9–7.1 (m, 5 H, piperonyl Ar protons+aromatic protons ortho to methoxy), 7.63 (d, J=8.6 Hz, 2 H, aromatic protons meta to methoxy), 7.73 and 7.86 (d, J=9.0 Hz, N<u>H</u>—SO$_2$), 8.89 (br s, 1 H, NH$^+$), 9.70 and 9.80 (br s, 1 H, NH—O<u>H</u>), and 10.77, 10.82 ppm (br s, 1 H, N<u>H</u>—OH).

EXAMPLE 38

2R-(4S-(2-Dimethyl-1-hydroxy-2-oxo-3H-imidazolidinyl)-cyclopentylpropionic acid (4-piperonyl)-piperazinamide Obtained as a white solid by stirring (3S-amino-2R-cyclopentylmethyl-4-hydroxyamino)succinyl-(4-piperonyl) piperazinamide (Example 27) in neat acetone, followed by removal of water and solvent by rotoevaporation with anhydrous ethanol. Trifluoroacetate salt. H$^1$-NMR (400 MHz, DMSO-d$_6$): 1.0–1.8 (m, 11 H, cyclopentylmethyl), 1.16 and 1.17 (each s, 3 H, Me), 2.9–4.4 (m, 10 H, C<u>H</u>-cyclopentylmethyl+piperazine methylene protons+ C<u>H</u>$_2$—Ar+C<u>H</u>—NH$_2$$^+$—), 6.05 (s, 2 H, O—C<u>H</u>$_2$—O), 6.9–7.1 (m, 3 H, piperonyl Ar protons), 9.64 (s, 1 H, N—O<u>H</u>), and 9.9 ppm (br s, 2 H, —NH$_2$$^+$—).

EXAMPLE 39

(4-Hydroxyamino-2R-(4-methoxy)phenpropyl-3S-(3-pyridyl)methylamino)succinyl-piperidinamide H$^1$-NMR (400 MHz, DMSO-d$_6$): 1.1–1.6 (m, 10 H, CH—C<u>H</u>$_2$C<u>H</u>$_2$—CH$_2$Ph+piperidine 3-,4-,5-methylene protons), 2.40 (m, 2 H, C<u>H</u>$_2$—Ph), 3.06 (m, 2 H, C<u>H</u>—NH+ C<u>H</u>-phenpropyl), 3.2–3.6 (m, 4 H, piperidine 2-,6-methylene), 3.37 and 3.70 (each d, J=16.2 Hz; 2 H, NH—C<u>H</u>$_2$-pyridine), 3.68 (s, 3 H, methoxy), 6.79 (d, J=7.6 Hz, 2 H, aromatic protons ortho to methoxy), 7.10 (d, J=7.6 Hz, 2 H, aromatic protons meta to methoxy), 7.26 (dd, J=4.7 and 7.7 Hz, 1 H, 5-pyridine proton), 7.60 (ddd, J=1.7, 2.1 and 7.7 Hz, 1 H, 4-pyridine proton), 8.38 (dd, J=1.7 and 4.7 Hz, 1 H, 6-pyridine proton), and 8.39 ppm (d, J=2.1 Hz, 1 H, 2-pyridine proton); NH—O<u>H</u> and N<u>H</u>—OH not detected.

EXAMPLE 40

N-((3S-Amino-4-hydroxyamino-2R-(4-methoxy) phenpropyl)succinyl)-L-proline-piperonylamide Trifluoroacetate salt. H$^1$-NMR (400 MHz, DMSO-d$_6$): 1.4–2.1 (m, 8 H, CH—C<u>H</u>$_2$C<u>H</u>$_2$—CH$_2$Ph+proline 3-,4-methylene), 2.45 (m, 2 H, C<u>H</u>$_2$—Ph), 2.95 (m, 1 H, C<u>H</u>-phenpropyl), 3.5–3.7 (m, 3 H, C<u>H</u>—NH$_3$$^+$+proline 5-methylene), 3.67 (s, 3 H, methoxy), 4.16 and 4.21 (each dd, J=5.6 and 13.7 Hz, 1 H, CONH—C<u>H</u>(H)—Ar), 4.34 (dd, J=4.3 and 8.1 Hz, proline N—C<u>H</u>—CO), 6.07 (s, 2 H, O—C<u>H</u>$_2$—O), 6.6–6.9 (m, 5 H, piperonyl Ar protons+aromatic protons ortho to methoxy), 7.06 (d, J=8.6 Hz, 2 H, aromatic protons meta to methoxy), 8.15 (br s, 3 H, NH$_3$$^+$), 8.31 (dd, J=5.6 Hz, 1 H, CO—N<u>H</u>—CH$_2$—Ar), 9.39 (s, 1 H, NH—O<u>H</u>), and 11.16 ppm (s, 1 H, N<u>H</u>—OH).

EXAMPLE 41

(3S-Amino-4-hydroxyamino-2R-(4-methoxy) phenpropyl)succinyl-N-isopropyl-N-methylamide, and (3R-Amino-4-hydroxyamino-2R-(4-methoxy) phenpropyl)succinyl-N-isopropyl-N-methylamide A solution of 4S-benzyloxycarbonyl-1-tert-butoxycarbonyl-3R-(4-methoxy)phenpropylazetidin-2-one (350 mg; see Preparation C) in DMF (6 mL) was allowed to react with sodium azide (10 mg) and N-isopropyl-N-methylamine (0.16 mL) for 30 hr at room temperature. Workup and flash chromatography over silica (n-hexane/ EtOAc) afforded, in this order, (4-benzyloxycarbonyl-3S-tert-butoxycarbonylamino-2R-(4-methoxy)phenpropyl) succinyl-N-isopropyl-N-methylamide (160 mg) and the product from base-assisted epimerization, (4-benzyloxycarbonyl-3R-tert-butoxycarbonylamino-2R-(4-methoxy)phenpropyl)succinyl-N-isopropyl-N-methylamide (80 mg). ESI-MS (both isomers) 527 (MH)$^+$.

Separate elaboration of the two diastereoisomers above, in a manner analogous to that described in Examples 1–3, afforded the title compounds (both trifluoroacetate salts). In DMSO, bot compounds exist as a 2:1 mixture (M, major; m, minor; H$^1$-NMR) of rotamers at the tertiary amide.

3S-Isomer: H$^1$-NMR (600 MHz, DMSO-d$_6$): 0.97 and 1.02 (each d, J=7.0 Hz, 6 H, CHMe$_2$ of M), 1.01 and 1.11 (each d, J=7.0 Hz; 6 H, CHMe$_2$ of m), 1.47 (m, 4 H, CH—CH$_2$CH$_2$—CH$_2$Ph), 2.44 (m, 2 H, CH$_2$—Ph), 2.65 (s, 3 H, NMe of m), 2.77 (s, 3 H, NMe of M), 3.11 (m, 1 H, CH-phenpropyl of M), 3.18 (m, 1 H, CH-phenpropyl of m), 3.69 (s, 3 H, methoxy), 3.71 (m, 1 H, CH—NH$_3^+$ of M), 3.76 (m, 1 H, CH—NH$_3^+$ of m), 4.03 (m, 1 H, CH—Me$_2$ of m), 4.69 (m, 1 H, CH—Me$_2$ of M), 6.82 (d, J=8.6 Hz, 2 H, aromatic protons ortho to methoxy), 7.05 (d, J=8.6 Hz, 2 H, aromatic protons meta to methoxy), 7.98 (br s, 3 H, NH$_3^+$ of m), 8.13 (br s, 3 H, NH$_3^+$ of M), 9.36 (s, 1 H, NH—OH of M), 9.37 (s, 1 H, NH—OH of m), 11.12 (s, 1 H, NH—OH of M), and 11.15 ppm (s, 1 H, NH—OH of m).

3R-Isomer: H$^1$-NMR (600 MHz, DMSO-d$_6$): 0.98 and 1.00 (each d, J=6.5 Hz; 6 H, CHMe$_2$ of M), 1.04 and 1.11 (each d, J=6.5 Hz; 6 H, CHMe of m), 1.3–1.8 (m, 4 H, CH—CH$_2$CH$_2$—CH$_2$Ph), 2.46 (m, 2 H, CH—Ph), 2.64 (s, 3 H, N Me of m), 2.80 (s, 3 H, NMe of M), 3.17 (m, 1 H, CH-phenpropyl, 3.59 (m, 1 H, CH—NH$_3^+$), 3.69 (s, 3 H, methoxy of M), 3.70 (s, 3 H, methoxy of m), 4.12 (m, 1 H, CH—Me$_2$ of m), 4.67 (m, 1 H, CH—Me$_2$ of M), 6.81 (d, J=8.5 Hz, 2 H, aromatic protons ortho to methoxy of M), 6.83 (d, J=8.5 Hz, 2 H, aromatic protons ortho to methoxy of m), 7.05 (d, J=8.5 Hz, 2 H, aromatic protons meta to methoxy of M), 7.09 (d, J=8.5 Hz, 2 H, aromatic protons meta to methoxy of m), 8.21 (br s, 3 H, NH$_3^+$), 9.20 (br s, 1 H, NH—OH of m), 9.22 (br s, 1 H, NH—OH of M), and 10.99 ppm (br s, 1 H, NH—OH).

EXAMPLE 42

(3S-Amino-4-hydroxyamino-2R-(4-methoxy) phenpropyl)succinyl-4-(2-pyridyl)piperazinamide Trifluoroacetate salt. H$^1$-NMR (400 MHz, DMSO-d$_6$): 1.48 (m, 4 H, CH—CH$_2$CH$_2$—CH$_2$Ph), 2.44 (m, 2 H, CH$_2$—Ph), 3.22 (m, 1 H, CH-phenpropyl), 3.3–3.8 (m, 9 H, CH—NH$_3^+$ and piperidine methylene protons), 3.68 (s, 3 H, methoxy), 6.70 (dd, J=5.1 and 6.8 Hz, 5-pyridine proton), 6.78 (d, J=8.6 Hz, 2 H, aromatic protons ortho to methoxy), 6.88 (d, J=8.6 Hz, 1 H, 3-pyridine proton), 7.05 (d, J=8.6 Hz, 2 H, aromatic protons meta to methoxy), 7.60 (ddd, J=1.7, 6.8 and 8.6 Hz, 1 H, 4-pyridine proton), 8.10 (dd, J=1.7 and 5.1 Hz, 1 H, 6-pyridine proton), 8.20 (br s, 3 H, NH$_3^+$), 9.40 (br s, 1 H, NH—OH), and 11.19 ppm (s, 1 H, NH—OH).

EXAMPLE 43

(3S-Amino-4-hydroxyamino-2R-(4-methoxy) phenpropyl)succinyl-(4-(2,3-methylenedioxy) phenylaminocarbonyl)piperidinamide Trifluoroacetate salt. H$^1$-NMR (400 MHz, DMSO-d$_6$): In DMSO, the compound is present as two conformers, ca. 1:1, whose H$^1$-NMR signals coalesce upon heating. H$^1$-NMR (400 MHz, DMSO-d$_6$): 1.2–1.9 (m, 8 H, CH—CH$_2$CH$_2$—CH$_2$Ph+piperidine 3-,5-methylene), 2.45 (m, 2 H, CH$_2$—Ph), 2.50 (m, 1 H, piperidine 4-proton), 2.70 and 3.00 (each m; piperidine 2- and 6-axial protons), 3.20 (m, 1 H, CH-phenpropyl), 3.66 and 3.70 (each s, 3 H, methoxy of 2 conformers), 3.70 (m, 1 H, CH—NH$_3^+$), 3.90 and 4.40 (each m; 2 H, piperidine 2- and 6-equatorial protons), 5.95 (s, 2 H, O—CH$_2$—O), 6.8–7.3 (m, 7 H, aromatic protons), 8.00 (br s, 3 H, NH$_3^+$), 9.38 and 9.39 (each s; 1 H, NH—OH of 2 conformers), 9.82 and 9.83 (each s; 1 H, CO—NH—Ar), and 11.15 ppm (br s, 1 H, NH—OH).

In a manner analogous to that described in the previous Examples, there were prepared the following compounds:

EXAMPLE 44

(3S-Amino-4-hydroxyamino-2R-isobutyl)succinyl-N-methyl-N-(1S-methylaminocarbonyl-2-phenyl) ethylamide, trifluoroacetate salt H$^1$-NMR (600 MHz, DMSO-d$_6$): 0.73, 0.80 (two d, J=6.3 Hz, 6H), 1.1–1.5 (m, 3H), 2.55 (d, J=4.4 Hz, 3H), 2.83 (s, 3H), 3.05, 3.30 (two m, 2H), 3.10 (m, 1H), 3.60 (m, 1H), 4.70 (m, 1H), 7.0–7.3 (m, 5H), 7.81 (q, J=4.4 Hz, 1H), 8.28 (broad signal, 3H), 9.40 (broad signal, 1H), 11.13 (s, 1H).

EXAMPLE 45

(3S-Amino-4-hydroxyamino-2R-(4-methoxy) phenpropyl)succinyl-(4-piperonyl)piperazinamide

EXAMPLE 46

(3S-Amino-4-hydroxyamino-2R-(4-methoxy) phenpropyl)succinyl-4-(4-fluoropentylsulfonyl) piperazinamide

EXAMPLE 47

(2R-Cyclopentylmethyl-4-hydroxyamino-3S-(methylsulfonyl)amino)succinyl-(4-piperonyl) piperazinamide

EXAMPLE 48

(3S-Amino-4-hydroxyamino-2R-(4-methoxy) phenpropyl)succinyl-4-(4-acetylphenyl) piperazinamide

EXAMPLE 49

(3S-Amino-4-hydroxyamino-2R-(4-methoxy) phenpropyl)succinyl-4-(1-piperidyl)piperidinamide

EXAMPLE 50

(3S-Amino-2R-cyclopentylmethyl-4-hydroxyamino) succinyl-(1R-cyclohexylethyl)amide, trifluoroacetate salt H$^1$-NMR (400 MHz, DMSO-d$_6$): 0.9–1.9 (m, 22H); 0.95 (d, J=6.8 Hz, 3H), 2.60 (m, 1H), 3.55 (m, 2H), 7.87 (d, J=7.1 Hz, 1H), 8.0 (broad signal, 3H) 9.27 (s, 1H), 11.01 (broad signal, 1H).

EXAMPLE 51

(4-Hydroxyamino-3S-(4-methoxyphenylsulfonyl) amino-2R-(4-methoxy)phenpropyl)succinyl-piperidinamide

EXAMPLE 52

(3S-(4-Fluorophenylsulfonyl)amino-4-hydroxyamino-2R-(4-methoxy)phenpropyl)succinyl-piperidinamide

EXAMPLE 53

(3S-Amino-4-hydroxyamino-2R-(4-methoxy) phenpropyl)succinyl-cyclohexylamide

EXAMPLE 54

(3S-Amino-2R-cyclopentylmethyl-4-hydroxyamino) succinyl-piperazinamide

EXAMPLE 55

(3S-Amino-4-hydroxyamino-2R-(4-methoxy) phenpropyl)succinyl-cyclopentylamide

EXAMPLE 56

(3S-Amino-4-hydroxyamino-2R-(4-methoxy) phenpropyl)succinyl-(2R,S-methyl)piperidinamide

EXAMPLE 57

(3S-Amino-4-hydroxyamino-2R-(4-methoxy) phenpropyl)succinyl-2-(1-morpholino)ethylamide

EXAMPLE 58

(3S-Amino-2R-cyclopentylmethyl-4-hydroxyamino) succinyl-2-(N-methyl-N-piperonyl)aminoethylamide

EXAMPLE 59

(3S-Amino-4-hydroxyamino-2R-(4-methoxy) phenpropyl)succinyl-4-(1,1-di(4-fluoro) phenylmethyl)piperazinamide

EXAMPLE 60

(3S-Amino-2R-cyclopentylmethyl-4-hydroxyamino) succinyl-N-methyl-N-(2-(N-methyl-N-piperonyl) aminoethylamide

EXAMPLE 61

(2R-Cyclopentylmethyl-3S-(4-fluorophenylsulfonyl) amino-4-hydroxyamino)succinylpiperidinamide

EXAMPLE 62

(3S-Amino-4-hydroxyamino-2R-(4-methoxy) phenpropyl)succinyl-4-(4-piperidinecarbonyl) piperazinamide

EXAMPLE 63

(3S-Amino-2R-cyclopentylmethyl-4-hydroxyamino) succinyl-(3,5-dimethyl)piperazinamide

EXAMPLE 64

(3S-Amino-2R-biphenpropyl-4-hydroxyamino) succinyl-(4-piperonyl)piperazinamide, trifluoroacetate salt $H^1$-NMR (500 MHz, DMSO-$d_6$): 1.60 (m, 4H), 2.60, 2.70 (two m, 2H), 3.0–4.0 (broad signal, 10H), 3.30 (m, 1H), 4.02 (d, J=7.2 Hz, 1H), 5.93 (s, 2H), 6.6–6.8 (m, 3H), 7.30–7.70 (m, 9H).

EXAMPLE 65

(3S-Amino-2R-cyclopentylmethyl-4-hydroxyamino) succinyl-(1R-cyclohexyl-2-hydroxy)ethylamide

EXAMPLE 66

(3S-Amino-4-hydroxyamino-2R-(4-methoxy) phenpropyl)succinyl-4-(2-hydroxyethyl) piperazinamide

EXAMPLE 67

N-((3S-Amino-2R-cyclopentylmethyl-4-hydroxyamino)succinyl)-L-proline-N-(2,3-methylenedioxyphenyl)-carboxamide

EXAMPLE 68

N-((3S-Amino-2R-cyclopentylmethyl-4-hydroxyamino)succinyl)-D-proline--N-(2,3-methylenedioxyphenyl)-carboxamide

EXAMPLE 69

(2R-Cyclopentylmethyl-4-hydroxyamino-3S-(toluenesulfonyl)amino)succinyl-(1R-cyclohexylethyl)amide

EXAMPLE 70

(3S-Amino-2R-cyclopentylmethyl-4-hydroxyamino) succinyl-(2S-methyl-4-piperonyl)piperazinamide

EXAMPLE 71

(2R-Cyclopentylmethyl-4-hydroxyamino-3S-(8-(1,2,3,4-tetrahydroquinoline)sulfonyl)amino)succinyl-(1R-cyclohexylethyl)amide $H^1$-NMR (400 MHz, DMSO-$d_6$): 0.89 (d, J=6.8 Hz, 3H), 0.9–1.9 (m, 22H), 2.43 (m, 1H), 2.67 (m, 2H), 3.30 (m, 2H), 3.50 (m, 2H), 5.94 (s, 1H), 6.45 (dd J=7.3, 7.8 Hz, 1H), 7.03 (d, J=7.3 Hz, 1H), 7.30 (d, J=7.8 Hz, 1H), 7.3, 7.6 (two broad signals, 2H), 8.72 (broad signal, 1H) 10.50 (broad signal, 1 H).

EXAMPLE 72

(3S-Amino-2R-cyclopentylmethyl-4-hydroxyamino) succinyl-(1S-cyclohexyl-1-dimethylaminocarbonyl)-methylamide $H^1$-NMR (400 MHz, DMSO-$d_6$): 0.9–1.9 (m,22H), 2.68 (m, 1H), 2.79,3.06 (two singlets, 6H), 3.47 (m, 1H), 4.50 (dd, J=7.3, 8.8 Hz, 1H), 7.80 (broad signal, 3H), 8.16 (d, J=7.3 1H), 9.21 (broad signal, 1H), 11.00 (broad signal, 1H).

EXAMPLE 73

(3S-Amino-2R-biphenpropyl-4-hydroxyamino) succinyl-(1R-cyclohexylethyl)amide, trifluoroacetate salt $H_1$-NMR (400 MHz, DMSO-$d_6$): 0.90–1.9 (m, 15H), 0.94 (d, J=6.8 Hz, 3H), 2.57 (m, 2H), 2.62 (m, 1H), 3.57 (m, 1H), 3.67 (m, 1H), 7.25, 7.55 (two doublets, J=8.3 Hz, 4H), 7.30 (m, 1H), 7.42 (m, 2H), 7.60 (m,2H), 8.02 (d, J=8.8 Hz, 1H), 8.18 (broad signal, 3H), 9.32 (s, 1H), 11.20 (s, 1H).

Preparation A

4S-Benzyloxycarbonyl-1-tert-butoxycarbonyl-3R-isobutylazetin-2-one

Step A

A solution of 1-tert-butyldimethylsilyl-4S-carboxyazetidin-2-one (6.2 g) in dry THF (100 mL) was teated dropwise at 0–5° C. with a 2M solution of LDA (28.4 ml) in the same solvent, to ontain an orange solution of the di-anion. After 15 min, isobutyl iodide (6.8 mL) was added at 0° C. under stirring, and the resulting yellow-green solution was left at the same temperature overnight. Quenching with 1M aqueous KHSO4 (300 mL), followed by extraction with EtOAc, afforded crude 1-tert butyldimethylsilyl-4S-carboxy-3R-isobutylazetidin-2-one as an orange syrup (7 g).

The above material was dissolved in dry DMF (20 mL) and treated dropwise, in this order, with triethylamine (5.85 mL) and benzyl bromide (4.8 mL). After 4 hours at room temperature, the mixture was partitioned between water and EtOAc. The organic layer was washed with brine, dried and evaporated to give crude 4S-benzyloxycarbonyl-1-tert-butyldimethylsilyl-3R-isobutylazetidin-2-one as an orange oil. This material was dissolved in THF (10 mL) and left overnight in the presence of tetrabutylammonium fluoride (2.6 g) and acetic acid (1.7 mL). The mixture was partioned between saturated aqueous NaHCO$_3$ and EtOAc, and the organic phase was dried and evaporated. Flash cromatography over silica gel (n-hexane/EtOAc) afforded 4S-benzyloxycarbonyl-3R-isobutylazetidin-2-one (4.7 g) as white needles. FT-IR (KBr) 3229 (N), 1744–1750 br (CO) cm$^{-1}$. $H^1$-NMR (200 MHz, CDCl$_3$) 0.87 (d, 3 H, J=6.5 Hz); 0.94 (d, 3 H, J=6.5 Hz); 1.57–1.82 (m, 3 H); 3.32 (m, 1 H); 3.90 (d, 1 H, J=2.4 Hz); 5.22 (ABq, 2 H); 5.96 (br s, 1 H); 7.36 (m, 5 H) ppm.

Step B

A solution of the material from step A above (1 g) in CH$_3$CN (15 mL) was treated with DMAP (4-dimethylaminopyridine; 46 mg) and Boc$_2$O (di-tert-butyldicarbonate; 1.67 g) at 40° C. for 30 min and then at room temperature overnight. After removal of the solvent in vacuo, the residue was dissolved in EtOAc and sequentially washed with aqueous 1M KHSO$_4$, aqueous saturated NaHCO$_3$ and brine. Drying over Na$_2$SO$_4$ and evaporation left the title compound as a yellow oil. FT-IR (CHCl$_3$) 1820 (azetidinone CO), 1750 (ester CO), 1728 (carbamate CO) cm$^{-1}$.

Preparation B

3R-Isobutyl-4S-(4-nitro)benzyloxycarbonyl-1-(4-toluenesulfonyl)azetidin-2-one

Step A

In a manner analogous to that described in Preparation A, reaction of 1-tert-butyldimethylsilyl-4S-carboxyazetidin-2-one (4.1 g) with a 2M solution of LDA in THF (18.8 mL) and isobutyl iodide (4.53 mL), followed by reaction with p-nitrobenzyl bromide (4.25 g) and triethylamine (3.7 mL), and finally by reaction with acetic acid (1 mL) and tetrabutylammonium fluoride (1.1 g), afforded 3R-isobutyl-4S-(4-nitro)benzyloxycarbonylazetidin-2-one (3.6 g) as a yellow solid.

Step B

A solution of the material from Step A above (630 mg) in CH$_2$Cl$_2$ (10 mL) was treated with triethylamine (0.65 ml) and p-toluenesulfonyl chloride (783 mg) at room temperature overnight under a nitrogen atmosphere. After quenching with saturated aqueous NaHCO$_3$, the organic layer was collected, washed with aqueous saturated NH$_4$Cl, brine and dried over Na$_2$SO$_4$. Evaporation and purification by flash cromatography on silica gel (n-hexane/EtOAc) afforded the title compound (320 mg) as an oil. FT-IR (CHCl$_3$) 1802 (azetidinone CO), 1752 (ester CO) cm$^{-1}$. H$^1$-NMR (400 MHz, CDCl$_3$) 0.79 (d, 3 H, J=6.4 Hz); 0.88 (d, 3 H, J=6.4 Hz); 1.54–1.72 (m, 3 H); 2.44 (s, 3 H); 3.20 (m, I H), 4.32 (d, I H, J=3.2 Hz); 5.19 (s, 2 H); 7.31 (d, 2 H, J=8.5 Hz); 7.33 (m, 5 H), 7.87 (d, 2 H, J=8.5) ppm.

Preparation C

4S-Benzyloxycarbonyl-1-tert-butoxycarbonyl-3R-(4-methoxy)phenpropylazetidin-2-one Step A In a manner analogous to that described in Preparation A, reaction of 1-tert-butyldimethylsilyl-4S-carboxyazetidin-2-one (21 g) with a 2M solution of LDA in THF (93.8 mL) and (4-methoxy)phenpropyl iodide (45.9 g; see Preparation F). followed by reaction with benzyl bromide (32.6 mL) and triethylamine (15.3 mL), afforded crude 4S-benzyloxycarbonyl-1-tert-butyldimethylsilyl-3R-(4-methoxy)phenpropylazetidin-2-one (90.4 g).

This material, dissolved in CH$_3$CN and aqueous 2N HCl, was let stirring at room temperature overnight. The solvent was evaporated and the aqueous phase was extracted with EtOAc several times. The organic layer was dried over Na$_2$SO$_4$ and evaporated. The residue was purified by flash cromatography on silica gel (n-hexane/EtOAc) to afford 4S-benzyloxycarbonyl-3R-(4-methoxy)phenpropylazetidin-2-one (8.6 g) as a white solid.

Step B

In a manner analogous to that described in Preparation A (step B), reaction of the material from step A above (8.6 g) with DMAP (300 mg) and Boc$_2$O (7.93 g) afforded the title compound as a yellow oil (9.1 g). H$^1$-NMR (200 MHz, CDCl$_3$) 1.44 (s, 9 H); 1.6–1.9 (m, 4 H); 2.55 (m, 2 H); 3.15 (m, 1 H); 3.79 (s, 3 H); 4.09 (d, I H, J =3.2 Hz); 5.19 and 5.25 (two d, 2 H, J=12.2 Hz); 6.81 (d, 2 H, J=8.7 Hz); 7.02 (d, 2 H, J=8.7 Hz), 7.34 (m, 5 H) ppm.

Preparation D

4S-Benzyloxycarbonyl-1-tert-butoxycarbonyl-3R-cyclopentylmethylazetidin-2-one

Step A

In a manner analogous to that described in Preparation A, reaction of 1-tert-butyldimethylsilyl-4S-carboxyazetidin-2-one (1 g) with a 2M solution of LDA in THF (4.6 ml) and cyclopentymethyl iodide (2 g; see Preparation E), followed by treatment with benzyl bromide (0.93 mL) and triethylamine (1 ml), afforded crude 4S-benzyloxycarbonyl-1-tert-butyldimethylsilyl-3R-cyclopentylmethylazetidin-2-one (6 g).

Step B

This material, dissolved in CH$_3$CN and aqueous 2N HCl, was let stirring at room temperature overnight. The solvent was evaporated and the aqueous phase was extracted with EtOAc several times. The organic layer was dried over Na$_2$SO$_4$ and evaporated. The residue was purified by flash cromatography on silica gel (n-hexane/EtOAc) to afford 4S-benzyloxycarbonyl)-3R-cyclopentylmethylazetidin-2-one (1.3 g) as a yellow solid.

Step C

In a manner analogous to that described in Preparation A (step B), reaction of the material from step B above (1.3 g) with DMAP (21 mg) and Boc$_2$O (566 mg) afforded the title compound as a colourless oil (530 mg). H$^1$-NMR (200 MHz, CDCl$_3$) 0.9–2.0 (m, 11 H); 1.45 (s, 9 H), 3.15 (m, 1 H); 4.12 (d, 1 H, J=3.0 Hz); 5.17 and 5.30 (two d, 2 H, J=12.0 Hz); 7.35 (m, 5 H) ppm. FAB-MS 388 (MH)$^+$, 332, 288, 252, 135, 91, 57 m/z.

Preparation E

Cyclopentylmethyl Iodide

Methanesulfonyl chloride (25.5 mL) was added dropwise to a solution of cyclopentanemethanol (32.4 mL) and triethylamine (46 mL) in dichloromethane (500 ml) at 0° C. After stirring overnight at room temperature, the mixture was sequentially washed with water, 2% hydrochloric acid, 4% aqueous sodium bicarbonate and water again. Following drying over sodium sulfate, the solvent was removed under vacuum, affording crude cyclopentylmethyl methanesulfonate (ca. 50 g) as a colourless oil. A mixture of this product and sodium iodide in acetone (600 ml) was heated at reflux in the dark for 16 hours. After cooling to room temperature, the reaction mixture was poured into petrol ether/water 2:1 (1.5 L) under stirring. The organic layer was washed twice with water, dried (Na$_2$SO$_4$) and carefully concentrated under reduced pressure (50 mm; temperature of the bath <30° C.). The residue was distilled in vacuo. The title product was obtained as a light yellow oil (39 g), by collecting the fraction boiling at 101–102°/70 mm.

Preparation F 3-(4-Methoxyphenyl)-propyl iodide

Methanesulfonyl chloride (31 mL) was added dropwise to a solution of 3-(4-methoxyphenyl)-1-propanol (50 g) and triethylamine (56 mL) in dichloromethane (800 mL) at 0° C. The resulting mixture was stirred overnight at room temperature. After washing with water, 2% hydrochloric acid and 4% aqueous sodium bicarbonate, the organic solution was dried over sodium sulfate and rotoevaporated to yield crude 3-(4-methoxyphenyl)-1-propyl methanesulfonate as a colourless solid (ca. 83 g). This product and sodium iodide (75 g) in acetone (800 mL) were heated at reflux in the dark for 20 hours. After cooling to room temperature, the reaction mixture was poured into n-hexane/EtOAc/water 1:1:1 (1.5 L) under stirring. The organic layer was washed with water, diluted aqueous sodium metabisulfite and 4% aqueous sodium bicarbonate, then dried (Na$_2$SO$_4$) and concentrated under reduced pressure. The residue was purified by passing it through a short pad of silica gel (eluting with n-hexane/EtOAc 95:5). The title compound was obtained as a pale yellow solid (75 g).

Preparation G

Dicyclohexylmethyl Amine

A solution of dicyclohexylacetic acid (4.5 g) in dichloromethane (50 mL) was treated with oxalyl chloride (2.5 mL). Addition of a catalytic amount of N,N-dimethylformamide (1 drop) caused immediate gas evolution to take place. The reaction mixture was stirred for 2 hr, then concentrated to dryness. The residue, consisting of crude dicyclohexylacetyl chloride, was dissolved in acetone (45 mL) and treated at 0° C. with a solution of sodium azide (2.6 g) in water (45 mL). After stirring for 1 hr at 0° C., toluene (100 mL) was added. The organic layer (mainly containing dicyclohexylacetyl azide as shown by IR absorption band at 2128 cm$^{-1}$) was separated, washed twice with brine, dried (Na$_2$SO$_4$), then heated at reflux for 2 hr. Following evaporation of the solvent, a waxy solid was obtained which mainly consisted of dicyclohexylmethyl isocyanate (IR absorption band at 2275 cm$^{-1}$). This crude isocyanate was suspended in 20% hydrochloric acid (100 mL) and heated at reflux for 8 h. The insoluble material was filtered off and the filtrate was concentrated in vacuo. The solid residue was taken up in diethyl ether/1N aqueous NaOH and the aqeous layer was re-extracted with ethyl ether. The organic phases were joined and washed with brine, then dried (Na$_2$SO$_4$) and rotoevaporated. The title product was thus obtained as a colourless oil (1.8 g). H$^1$-NMR (200 MHz, DMSO-d$_6$) 0.8–1.8 (m, 22 H); 2.01 (t, 1 H, J=5.4 Hz) ppm.

Preparation H

N-(tert-Butoxycarbonyl)-3R-isobutyl-L-aspartic acid 4-piperidinamide ("Aspartic Route")

Step A

A solution of N-(tert-butoxycarbonyl)-L-aspartic acid 1-benzyl ester (1 g) and piperidine (0.32 mL) in acetonitrile (15 mL) was allowed to react with N-methylmorpholine (0.42 mL) and TBTU (1.2 g) for 6 hr at room temperature. The solvent was removed and the residue, dissolved in EtOAc, was sequentially washed with 2% aqueous hydrochloric acid, saturated aq. NaHCO$_3$ and brine. After drying (Na$_2$SO$_4$) and rotoevaporation, the resulting yellowish oil was purified by flash chromatography over silica to obtain N-(tert-butoxycarbonyl)-L-aspartic acid 1-benzyl ester-4-piperidinamide (900 mg) as a colorless oil.

Step B

A solution of the compound from step A above (700 mg) in ethanol (30 mL) was exposed to a hydrogen atmosphere in the presence of 10% Pd-C (70 mg) for 4 hr at room temperature. After filtration (Celite filter aid) and rotoevaporation, N-(tert-butoxycarbonyl)-L-aspartic acid 4-piperidinamide (500 mg) was obtained as a yellowish foam.

Step C

The material from step B above (200 mg) in dry THF (5 mL) was treated at −40° C. under a nitrogen atmosphere with a 2 M solution of LDA in heptane/THF/benzene (Aldrich; 1.07 mL). Isobutyl iodide (0.09 mL) was then added, and the mixture left rise to room temperature. After 4 hr; the reaction mixture was quenched with saturated aqueous NH$_4$Cl and extracted with EtOAc. Washing with saturated aqueous NaHCO$_3$, drying over sodium sulfate and rotoevaporation afforded a mixture of the unreacted starting material and N-(tert-butoxycarbonyl)-3R-isobutyl-L-aspartic acid 4-piperidinamide.

Step D

The crude material from step C above in DMF (10 mL) was allowed to react with benzyl bromide (0.16 mL) and triethyl amine (0.24 mL) for 1 day at room temperature. After workup, the title compound was isolated by flash chromatography (gradient n-hexana/EtOAc mixtures) to obtain the title compound as a yellowish oil, which is the same as (4-benzyloxy-3S-tert-butoxycarbonylamino-2R-isobutyl)succinyl-piperidinamide obtained from the "azetidinone route" and described in Example 1 above. FT-IR (CHCl$_3$) 3433 br (NH), 1753 (ester CO), 1714 (carbamate CO), 1626 (amide CO) cm$^{-1}$. H$^1$-NMR (200 MHz, CDCl$_3$) 0.89 and 0.91 (two d, 6 H, J=6.6 Hz); 1.42 (s, 9 H); 1.2–1.8 (m, 9 H); 3.1–3.5 (m, 5 H); 4.48 (dd, 1 H, J=4.1 and 10.0 Hz); 5.06 and 5.19 (two d, 2 H, J=12.4 Hz); 6.45 (d, 1 H, J=10.0 Hz); 7.32(m, 5 H) ppm.

EXAMPLE 74

Tablets containing the following ingredients may be produced in a conventional manner:

| Ingredient | Per Tablet |
| --- | --- |
| Amine derivative | 25.0 mg |
| Lactose | 125.0 mg |
| Maize starch | 75.0 mg |
| Talc | 4.0 mg |
| Magnesium stearate | 1.0 mg |
| Total weight | 230.0 mg |

EXAMPLE 75

Capsules containing the following ingredients may be produced in a conventional manner:

| Ingredient | Per capsule |
| --- | --- |
| Amine derivative | 50.0 mg |
| Lactose | 165.0 mg |
| Maize starch | 20.0 mg |
| Talc | 5.0 mg |
| Capsule fill weight | 240.0 mg |

What is claimed is:

1. A compound that is an amine derivative of formula (I):

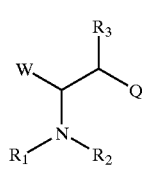

wherein:

W is —CONHOH;

wherein:

R$_1$ and R$_2$, which are the same or different, are each independently hydrogen;

a group G, that is methyl, C$_2$–C$_{10}$ alkyl, C$_2$–C$_{10}$ alkenyl, C$_3$–C$_7$ cycloalkyl, cycloalkyl-C$_1$–C$_{10}$-alkyl, aryl, aryl-$C_1$–$C_{10}$-alkyl, aryl-$C_2$–$C_{10}$-alkenyl, said methyl, alkyl, alkenyl, cycloalkyl, and aryl groups being unsubstituted or substituted by one to three substituents;

$SO_2$—G, wherein G is as defined above;
SO—G, wherein G is as defined above;
$SO_2$—$NH_2$;
$SO_2$—NHG; or
$SO_2$—NGG', wherein G is as defined above and G', which is the same or different, is as defined above for G;

wherein:

$R_3$ is $C_1$–$C_{15}$ alkyl, either unsubstituted or substituted by a $C_3$–$C_7$ cycloalkyl group, the alkyl and/or the cycloalkyl group being either unsubstituted, or substituted by one to three substituents selected from methyl, ethyl, $C_3$–$C_4$ linear or branched alkyl, fluoro, chloro, $C_1$–$C_4$ alkoxy, nitro, amino, dimethylamino, carboxy and carboxymethyl; or $R_3$ is a group —R—X—$R^1$, wherein:
R is a chemical bond, —$CH_2$—, —$(CH_2)_m$— wherein m is an integer from 2 to 5, —CH=CH—, —$CH_2$CH=CH—, phenylene (i.e., —$C_6H_4$—), —$CH_2$CH=CH—$C_6H_4$—, —$CH_2CH_2$CH=CH—, —$CH_2$—CC—, —$CH_2CH_2$—CC—, —$CH_2CH_2$CH=CH—$C_6H_4$—, —$CH_2$—CC—$C_6H_4$—, or —$CH_2CH_2$—CC—$C_6H_4$—;
X is a direct bond, an oxygen atom, a sulfur atom, or a sulfinyl —S(O)—, sulfonyl —$S(O)_2$ or carbamoyl group —CONH— or —NHCO—; and
$R^1$ is $C_1$–$C_6$ alkyl, $C_2$–$C_6$ alkenyl, phenyl, phenyl-($C_1$–$C_6$)-alkyl, phenyl-($C_2$–$C_6$)-alkenyl, either unsubstituted or substituted by a group selected from F, Cl, Br, $C_1$–$C_4$ alkyl, $C_1$–$C_4$ alkoxy, alkylthio, arylthio, alkylsulfonyl, and arylsulfonyl;

wherein:

Q, is a secondary or tertiary carboxyamide, and is:
a group —CONHG or —CONGG', wherein G and G' are as defined above;
a group —CONH—CHGG', wherein G and G' are as defined above;
a group —CONG"—CHGG', wherein G", being the same or different, is defined as G above;
a group —CONH—$CH_2$—CHGG',
a group —CONG"—$CH_2$—CHGG', wherein G, G' and G" are as defined above; or
a group —CO-azaheterocyclyl, wherein said carboxy group is bound to a ring nitrogen in said azaheterocyclyl group, that is either unsubstituted or substituted at any carbon or additional nitrogen atom, with the proviso that when Q is —CONHG and G is methyl, alkyl-methyl, cyclo-alkyl-methyl, aryl-methyl or heterocyclyl-methyl, then such methyl or substituted methyl cannot be further substituted by a group —$(CH_2)_t$—$CO_2H$, wherein t is 0, or esters and amides thereof;

or a pharmaceutically acceptable salt, physiologically hydrolyzable derivative, solvate or hydrate thereof.

2. The compound of claim 1, wherein the amine derivative has the formula (I'):

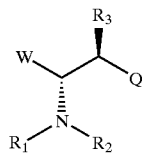

(I')

wherein:
W is —CONHOH;
$R_1$ and $R_2$ are:
both hydrogen; or
both $C_1$–$C_4$ alkyl, or
$R_1$ is hydrogen or methyl, and $R_2$ is a group G which is:
$C_1$–$C_{10}$ alkyl or $C_2$–$C_{10}$ alkenyl, either unsubstituted or substituted by $C_3$–$C_7$ cycloalkyl, or by one to three substituents selected from chloro, fluoro, hydroxy, $C_1$–$C_4$ alkoxy, $C_1$–$C_4$ alkyl, amino, methylamino, dimethylamino, —$CONH_2$, —$CONHCH_3$ or —$CONHC(CH_3)_3$, $C_1$–$C_4$ alkylthio, $C_1$–$C_4$ alkylsulfonyl, phenoxy, phenylthio and phenylsulfonyl, wherein the phenyl group may in turn be substituted by chloro, fluoro, methoxy or methyl; or
$C_3$–$C_7$ cycloalkyl; or
an aryl group which is optionally substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, phenyl, benzyl, phenethyl, phenpropyl, naphthyl and pyridyl, and wherein any phenyl, naphthyl and pyridyl ring may in turn be substituted by one to three substituents selected from chloro, fluoro, methyl, hydroxy, methoxy, amino, methylamino and dimethylamino; or
$C_1$–$C_{10}$ alkyl, substituted by any of the aryl group as defined above, and the derivatives thereof substituted by one to three substituents selected from chloro, fluoro, hydroxy, $C_1$–$C_4$ alkoxy, amino, methylamino, dimethylamino, $C_1$–$C_4$ alkyl, $C_3$–$C_7$ cycloalkyl, $C_1$–$C_4$ alkylthio, $C_1$–$C_4$ alkylsulfonyl, phenoxy, phenylthio and phenylsulfonyl, wherein the phenyl ring may be substituted by chloro, fluoro, methoxy or methyl; or
$R_1$ is hydrogen or methyl, and $R_2$ is —$SO_2$—G, wherein G is as defined above; or
$R_1$ is hydrogen or methyl, and $R_2$ is —$SO_2$—$NH_2$, —$SO_2$—NHG or —$SO_2$—NGG', wherein G is as defined above and G', which is the same or different, is as defined above for G; or
$R_1$ is hydrogen or methyl, and $R_2$ is —SO—NH—G, wherein G is as defined above; or
$R_3$ is —$CH_2$-alkyl, —$(CH_2)_n$-cycloalkyl, —$(CH_2)_n$—O-alkyl, —$(CH_2)_n$—O—$(CH_2)_m$ cycloalkyl, —$(CH_2)_n$—O—$(CH_2)_m$-aryl, [—$(CH_2)_n$—O—$(CH_2)_m$-heterocyclyl,] —$(CH_2)$,—S—alkyl, —$(CH_2)_n$—S—$(CH_2)_m$-cycloalkyl, —$(CH_2)_n$—S—$(CH_2)_m$-aryl, [—$(CH_2)_n$—S—$(CH_2)_m$-heterocyclyl,] —$(CH_2)_n$—SO-alkyl, —$(CH_2)_n$—SO—$(CH_2)_m$-cycloalkyl, —$(CH_2)_n$—SO—$(CH_2)_m$-aryl, [—$(CH_2)_n$—SO—$(CH_2)_m$-heterocyclyl,] —$(CH_2)_n$—$SO_2$-alkyl, —$(CH_2)_n$—$SO_2$—$(CH_2)_m$-cycloalkyl, —$(CH_2)_n$—$SO_2$—$(CH_2)_m$-aryl, [—$(CH_2)_n SO_2(CH_2)_m$- heterocyclyl,] —(CH$_2$)$_n$—CO-alkyl, —(CH$_2$)$_n$—CO—(CH$_2$)$_m$-cycloalkyl, or —(CH$_2$)$_n$—CO—(CH$_2$)$_m$-aryl [or —(CH$_2$)$_n$—CO—(CH$_2$)$_m$-heterocyclyl,] wherein alkyl, cycloalkyl, and aryl are as defined above, and n and m, being the same or different, are zero or an integer of 1 to 5, and wherein the alkyl, cycloalkyl, and aryl groups are optionally substituted by one to three substituents selected from chloro, fluoro, cyano, cyanomethyl, hydroxy, C$_1$–C$_4$ alkoxy, C$_1$–C$_4$ alkyl, C$_1$–C$_4$ alkylthio, C$_1$–C$_4$ alkylsulfonyl, phenyl, tolyl, 4-chlorophenyl, 4-fluorophenyl, 4-methoxyphenyl, 4-phenoxyphenyl, 4-(4-pyridyl)oxyphenyl, pyridyl; or R$_3$ is selected from isobutyl, n-hexyl, n-heptyl, n-octyl, n-nonyl, and cyclopentylmethyl; or R$_3$ is selected from 2-phenylethyl, 3-phenylpropyl, 4-phenylbutyl, 5-phenylpentyl, wherein the phenyl group is either unsubstituted or substituted by chloro, fluoro, cyano, cyanomethyl, methyl, ethyl, propyl, butyl, mesyl, methoxy, ethoxy, propoxy, butoxy, phenoxy, 4-chlorophenoxy, 4-fluorophenoxy, benzyloxy, phenyl, 4-fluorophenyl, 4-chlorophenyl, 4-methoxyphenyl, 4-cyanophenyl, 4-cyanomethylphenyl, 4-pyridyl, 4-pyridyloxy; or R$_3$ is selected from phenylsulfonylmethyl or phenylsulphonylethyl, wherein the phenyl group is either unsubstituted or substituted by chloro, fluoro, cyano, cyanomethyl, methyl, ethyl, propyl, butyl, methoxy, ethoxy, propoxy, butoxy, phenoxy, 4-chlorophenoxy, 4-fluorophenoxy, benzyloxy, phenyl, 4-fluorophenyl, 4-chlorophenyl, 4-methoxyphenyl, 4-cyanophenyl, 4-cyanomethylphenyl, 4-pyridyl, 4-pyridyloxy;

Q is:

a group —CONHG, —CONGG', —CONH—CHGG', CON(CH$_3$)—CHGG', —CONH—CH$_2$-CHGG', or —CON(CH$_3$)—CH$_2$-CHGG', wherein G and G', being as defined above, are selected from C$_1$–C$_6$ straight or branched alkyl, C$_5$–C$_6$ cycloalkyl, phenyl, tolyl, methylenedioxyphenyl, piperonyl and pyridyl, either unsubstituted or substituted by one to three substituents selected from chloro, fluoro, hydroxy, hydroxymethyl, C$_1$–C$_4$ alkoxy, amino, methylamino, dimethylamino, C$_1$–C$_4$ alkyl, C$_3$–C$_7$ cycloalkyl, —CONH$_2$, —CONHCH$_3$, —CONHC(CH$_3$)$_3$, —CONH(4-fluorophenyl), —CONH-pyridyl, —CONH-(methylenedioxy)phenyl, —CONH-piperonyl, carbomethoxy, carbethoxy, or a keto group —CO—R$^H$, wherein R$^H$, being as defined above, is selected from C$_1$–C$_4$ alkyl, phenyl, fluorophenyl, chlorophenyl, methylenedioxyphenyl, naphthyl, piperonyl, or a sulfone —(CH$_2$)$_n$—SO$_2$—R$^H$, wherein n and R$^H$ are as defined above, or a sulfonamide —(CH$_2$)$_n$—SO$_2$—NH$_2$, —(CH$_2$)$_n$—SO$_2$—NHR$^H$, —(CH$_2$)$_n$—SO$_2$NR$^H$R$^{III}$, wherein n, R$^H$ and R$^{III}$ are as defined above, including the special case wherein R$^H$ and R$^{III}$, taken together with the nitrogen atom to which they are attached, constitute an azaheterocyclyl ring, as defined above; or a group —CO-azaheterocyclyl, wherein azaheterocyclyl, being as defined above, is either unsubstituted or substituted by one to three substituents selected from hydroxy, hydroxymethyl, C$_1$–C$_4$ alkoxy, carbamoyl, carbomethoxy, carbethoxy, mesyl, C$_1$–C$_6$ linear or branched alkyl, trifluoromethyl, C$_3$–C$_7$ cycloalkyl, aryl, heterocyclyl and aryl-(C$_1$–C$_3$)alkyl or heterocyclyl-(C$_1$–C$_3$)alkyl; or said azaheterocyclyl group is substituted by a group —CONH—R$^H$, wherein R$^H$, being as defined above, is selected from methyl, isopropyl, tert-butyl, cyclopropyl, cyclopentyl, cyclohexyl, phenyl, 4-fluorophenyl, 4-chlorophenyl, 4-methoxyphenyl, 3,4-difluorophenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, methylenedioxyphenyl, piperonyl, 2-benzimidazolyl and 5-tetrazolyl; or said azaheterocyclyl group is substituted by a keto group —CO—R$^H$, or by a carbinol group of formula —CH(OH)R$^H$, wherein R$^H$, being as defined above, is selected from C$_1$–C$_4$ alkyl, phenyl, fluorophenyl, chlorophenyl, methylenedioxyphenyl, naphthyl, piperonyl, or by a sulfone —(CH$_2$)$_n$—SO$_2$—R$^H$, wherein n and R$^H$ are as defined above, or by a sulfonamide —(CH$_2$)$_n$—SO$_2$—NH$_2$, —(CH$_2$)$_n$—SO$_2$NHR$^H$, —(CH$_2$)$_n$—SO$_2$—NR$^H$R$^{III}$, wherein n, R$^H$ and R$^{III}$ are as defined above, including the special case wherein R$^H$ and R$^{III}$, taken together with the nitrogen atom to which they are attached, constitute an azaheterocyclyl ring, as defined above;

and the salts and solvates thereof.

3. A compound of formula (II'), which is a cyclic prodrug of a compound of formula (I') as claimed in claim 2:

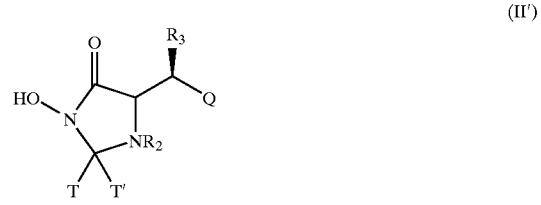

(II')

wherein R$_2$, R$_3$ and Q are as defined in claim 2, T is methyl or a hydrogen atom, and T' is methyl, C$_2$–C$_4$ lower alkyl, phenyl, benzyl, optionally substituted by one to three substituents selected from by C$_1$–C$_4$ alkyl, hydroxy, C$_1$–C$_4$ alkoxy, amino, methylamino, dimethylamino, chloro and fluoro.

4. The compound of claim 2, wherein R$_3$ is selected from isobutyl, n-hexyl, n-heptyl, n-octyl, n-nonyl, cyclopentylmethyl; or is selected from 3-phenylpropyl, 4-phenylbutyl, 5-phenylpentyl, 3-(p-diphenyl)propyl, 3-(4-pyridyl-4-phenyl)propyl, phenoxymethyl, 2-phenoxyethyl, 2-(phenylmethoxy)ethyl, 3-phenoxypropyl, 4-(phenylmethoxy)butyl, phenylsulfonylmethyl, 2-(phenylsulfonyl)ethyl, 3-(4-benzoylphenyl)propyl, including derivatives thereof substituted at any phenyl carbon atom by one to three substituents selected from chloro, fluoro, hydroxy, C$_1$–C$_4$ alkyl and C$_1$–C$_4$ alkoxy.

5. A process for producing a compound as defined in claim 1, comprising:

(a) reacting a beta-lactam compound of formula (III):

(III)

wherein R$_2$ and R$_3$ are as defined in claim 1 and W' is CONHOH, or a protected derivative thereof, with a primary or secondary acyclic amine of formula G—NH$_2$, GG'NH, GG'CH—NH$_2$, GG'CH—NHCH$_3$, GG'CH—CH$_2$—NH$_2$, or GG'CH—CH$_2$—NHCH$_3$, wherein G and G' are as defined in claim 1, or
with an amine of formula G—NH$_2$, GG'NH, GG'CH—NH$_2$ or GG'CH—CH$_2$—NH$_2$,
wherein G and G' are as defined in claim 1,
to obtain a compound of formula (IV):

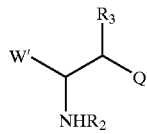
(IV)

wherein W', R$_2$ and R$_3$ are as defined above and Q is defined as in claim 1; and (b) converting said compound of formula (IV) into a compound of formula (I):

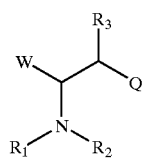
(I)

wherein W, R$_1$, R$_2$, R$_3$ and Q are as defined in claim 1; and (c) optionally removing the protecting groups and/or optionally converting any of the groups W, R, R$_1$, R$_2$, R$_3$ and Q into different groups W, R, R$_1$, R$_2$, R$_3$ and Q at the end of, or at any stage of the process.

6. A process for producing a compound of claim 2, comprising:

(a) reacting a beta-lactam compound of general formula (III'):

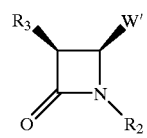
(III')

wherein R$_2$ and R$_3$ are as defined in claim 2, and W' is CONHOH, or a protected derivative thereof
with a primary or secondary acyclic amine of formula G—NH$_2$, GG'NH, GG'CH—NH$_2$, GG'CH—NHCH$_3$, GG'CH—CH$_2$—NH$_2$, GG'CH—CH$_2$—NHCH$_3$, or with an amine of formula G—NH$_2$, GG'NH, GG'CH—NH$_2$ or GG'CH—CH$_2$—NH$_2$,
wherein G and G' are as defined in claim 2;
to obtain a compound of formula (IV'):

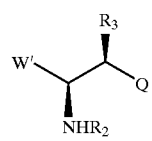
(IV')

wherein W', R$_2$, R$_3$ and Q are as defined in claim 2; and
(b) converting the compound of formula (IV') into a compound of formula (I'):

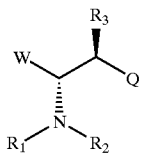
(I')

wherein W, R$_1$, R$_2$, R$_3$ and Q are as defined in claim 2; and (c) optionally removing the protecting groups and/or, optionally converting any of the groups W, R, R$_1$, R$_2$, R$_3$ and Q into different groups W, R, R$_1$, R$_2$, R$_3$ and Q at the end of, or at any stage of the process.

7. A process for producing the compound of claim 1, comprising:

(a) reacting an aspartic acid derivative of formula (V):

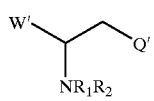
(V)

wherein W' is either carboxy or a protected derivative thereof, Q' is either Q as defined in claim 1, or carboxy or protected carboxy, and R$_1$, R$_2$ are as defined in claim 1,
with a reagent of formula R$_3$—X,
wherein R$_3$ is as defined in claim 1, and X is chloro, bromo or iodo, or sulfonyloxy, including triflate or mesylate, to obtain a compound of formula (VI):

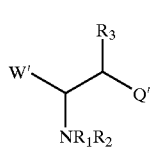
(VI)

wherein W', R$_1$, R$_2$, R$_3$ and Q' are as described above; and
(b) converting the compound of formula (VI) into a compound of formula (I):

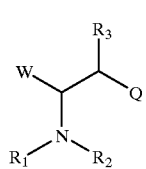
(I)

wherein W, R$_1$, R$_2$, R$_3$ and Q are as defined in claim 1; and (c) optionally removing the protecting groups and/or, optionally converting any of the groups W, R, R$_1$, R$_2$, R$_3$ and Q into different groups W, R, R$_1$, R$_2$, R$_3$ and Q at the end of, or at any stage of the process.

8. A pharmaceutical composition comprising:
a pharmaceutically acceptable diluent or carrier and the compound of claim 1.

9. A method for modulating a matrix metalloproteinase comprising administering an amount of the compound of claim 1 effective to modulate a matrix metalloproteinase to a subject.

10. The method of claim 9, wherein said compound is an inhibitor of said matrix metalloproteinase.

11. The method of claim 9 wherein said compound inhibits the release of TNF-α from a cell.

12. The method of claim 9, wherein said subject has a tumor or an inflammatory disease.

13. A method for inhibiting angiogenesis comprising administering the compound of claim 1 in a dosage and under conditions suitable for inhibiting angiogenesis.

14. A method for inhibiting tumor metastasis comprising administering the compound of claim 1 in a dosage and under conditions suitable for inhibiting tumor metastasis.

15. A method for reducing the degradation of the extracellular matrix comprising administering the compound of claim 1 in a dosage and under conditions suitable for inhibiting degradation of the extracellular matrix.

16. The compound (3S-Amino-4-hydroxyamino-2R-isobutyl)succinyl-dicyclohexylmethylamide.

17. The compound (3S-Amino-2R-cyclopentylmethyl-4-hydroxyamino)succinyl-(4-piperonylpiperazinamide.

18. The compound (2R-cyclopentylmethyl-4-hydroxyamino-3S-(4-methoxyphenyl)sulfonylamino)succinyl-(4-piperonyl)-piperazinamide.

* * * * *